(12) United States Patent
Schnidar et al.

(10) Patent No.: US 10,130,297 B2
(45) Date of Patent: Nov. 20, 2018

(54) METHODS FOR ASSESSING ERYTHEMA

(71) Applicant: Harald Schnidar, Vienna (AT)

(72) Inventors: Harald Schnidar, Vienna (AT);
Andreas Neubauer, Ulrichskirchen (AT)

(*) Notice: Subject to any disclaimer, the term of this patent is extended or adjusted under 35 U.S.C. 154(b) by 202 days.

(21) Appl. No.: 14/778,468

(22) PCT Filed: Mar. 19, 2014

(86) PCT No.: PCT/EP2014/055549
§ 371 (c)(1),
(2) Date: Sep. 18, 2015

(87) PCT Pub. No.: WO2014/147149
PCT Pub. Date: Sep. 25, 2014

(65) Prior Publication Data
US 2017/0000406 A1    Jan. 5, 2017

(30) Foreign Application Priority Data
Mar. 19, 2013 (EP) .................................. 13160048

(51) Int. Cl.
*A61B 5/00* (2006.01)
*A61B 5/103* (2006.01)
(Continued)

(52) U.S. Cl.
CPC ............ *A61B 5/445* (2013.01); *A61B 1/04* (2013.01); *A61B 5/0022* (2013.01);
(Continued)

(58) Field of Classification Search
CPC ..... A61B 5/445; A61B 5/0022; A61B 5/0077; A61B 5/7225; A61B 5/6898; A61B 5/441;
(Continued)

(56) References Cited

U.S. PATENT DOCUMENTS

| 5,241,468 A | 8/1993 | Kenet | |
|---|---|---|---|
| 8,303,984 B2 * | 11/2012 | Dorogi | A61K 8/19 424/450 |

(Continued)

FOREIGN PATENT DOCUMENTS

| EP | 0434279 | 6/1991 |
|---|---|---|
| JP | 2002-508509 | 3/2002 |

(Continued)

OTHER PUBLICATIONS

Chardon, A. et al. "Skin Colour Typology and Sustaining Pathways", International Journal of Cosmetic Science, vol. 13, No. 4, (1991), pp. 191-208.

(Continued)

*Primary Examiner* — Jacqueline Cheng
*Assistant Examiner* — Tho Tran
(74) *Attorney, Agent, or Firm* — Norton Rose Fulbright US LLP

(57) ABSTRACT

The present invention relates to methods for an objective and quantitative erythema documentation and analysis. In particular, the invention relates to a method for assessing erythema of a subject comprising the steps of measuring the light reflectance of a skin or mucosal area of the subject, obtaining the L* value and the a* value of said measurement according to the L*a*b* color space, and calculating the erythema value according to the formula $(L^*_{max} - L^*) \times a^*$.

14 Claims, 37 Drawing Sheets
(30 of 37 Drawing Sheet(s) Filed in Color)

The L*a*b* color space

A

B

(51) Int. Cl.
  *G06T 7/00* (2017.01)
  *A61B 1/04* (2006.01)
  *G06T 7/90* (2017.01)
  *G06F 19/00* (2018.01)
  *A61B 1/00* (2006.01)

(52) U.S. Cl.
  CPC .......... *A61B 5/0077* (2013.01); *A61B 5/1032* (2013.01); *A61B 5/441* (2013.01); *A61B 5/4842* (2013.01); *A61B 5/4848* (2013.01); *A61B 5/7225* (2013.01); *A61B 5/7275* (2013.01); *G06F 19/00* (2013.01); *G06T 7/0012* (2013.01); *G06T 7/0016* (2013.01); *G06T 7/90* (2017.01); *A61B 1/00009* (2013.01); *A61B 2576/00* (2013.01); *A61B 2576/02* (2013.01); *G06T 2207/30088* (2013.01)

(58) Field of Classification Search
  CPC ....... A61B 1/04; A61B 5/4848; A61B 5/4842; A61B 5/1032; A61B 5/7275; A61B 2576/02; G06T 7/0016; G06T 7/90; G06T 7/0012; G06T 2207/30088
  See application file for complete search history.

(56) References Cited

U.S. PATENT DOCUMENTS

| | | | |
|---|---|---|---|
| 2005/0030372 A1 | 2/2005 | Jung et al. | |
| 2010/0249731 A1 | 9/2010 | Stamatas | |
| 2015/0023897 A1* | 1/2015 | Oblong | A61K 8/368 424/60 |

FOREIGN PATENT DOCUMENTS

| | | |
|---|---|---|
| JP | 2010-524533 | 7/2010 |
| JP | 2010-227571 | 10/2010 |
| JP | 2010-537672 | 12/2010 |
| WO | WO1993/016635 | 9/1993 |
| WO | WO2006/106509 | 10/2006 |
| WO | WO2011/106792 | 9/2011 |

OTHER PUBLICATIONS

Nischik, M. et al.: "Analysis of Skin Erythema Using True-Color Images", IEEE Transactions on Medical Imaging, vol. 16, (Dec. 1997), p. 711-716.

Takiwaki, H.: "Measurement of Skin Color: Practical Application and Theoretical Considerations", The Journal of Medical Investigation, vol. 44, (Feb. 1, 1998), pp. 121-126.

Fernando et al., "Factors Affecting Acute Skin Toxicity in Patients Having Breast Irradiation After Conservative Surgery: A Prospective Study of Treatment Practice at the Royal Marsden Hospital", *Clinical Oncology*, 8: 226-233, 1996.

Pinnix et al., "Topical Hyaluronic acid vs. Standard of Care for the Prevention of Radiation Dermatitis after Adjuvant Radiotherapy for Breast Cancer: Single-Blind Randomized Phase III Clinical Trial", *Int J Radiat Oncol Biol Phys.*, 83(4): 1089-1094, 2012.

Takiwaki, "Measurement of skin color: practical application and theoretical considerations", *The Journal of Medical Investigation*, 44: 121-126, 1998.

Office Action issued in Japanese Application No. 2016-503656, dated Dec. 19, 2017.

* cited by examiner

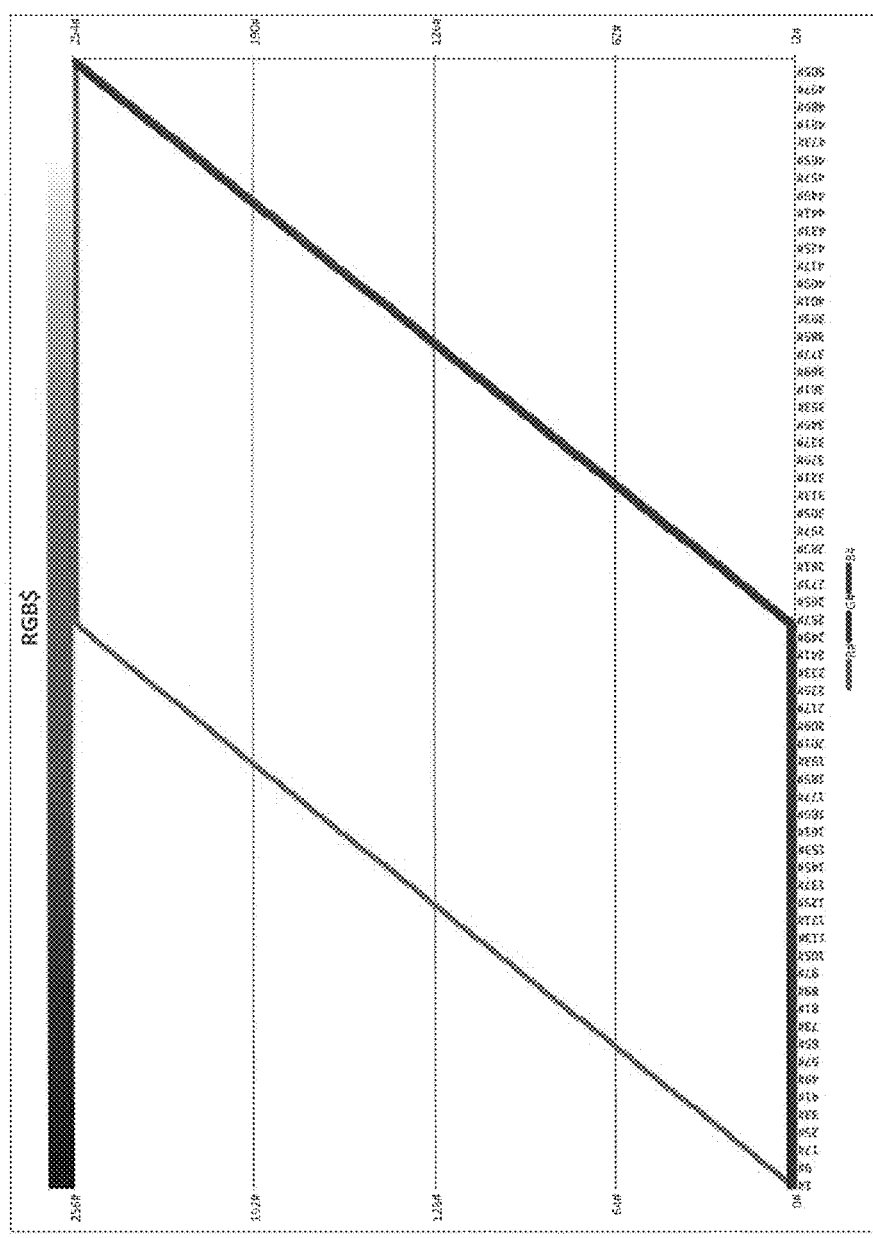

| R | G | B | | L | A | B | (255-L)*A |
|---|---|---|---|---|---|---|---|
| 0 | 0 | 0 | | 0 | 128 | 128 | 128 |
| 1 | 0 | 0 | | 0 | 128 | 128 | 128 |
| 2 | 0 | 0 | | 0 | 128 | 128 | 128 |
| 3 | 0 | 0 | | 0 | 128 | 128 | 128 |
| 4 | 0 | 0 | | 1 | 129 | 128 | 128,494118 |
| 5 | 0 | 0 | | 1 | 129 | 128 | 128,494118 |
| 6 | 0 | 0 | | 1 | 129 | 128 | 128,494118 |
| 7 | 0 | 0 | | 1 | 129 | 128 | 128,494118 |
| 8 | 0 | 0 | | 1 | 130 | 128 | 129,490196 |
| 9 | 0 | 0 | | 1 | 130 | 128 | 129,490196 |
| 10 | 0 | 0 | | 1 | 130 | 128 | 129,490196 |
| 11 | 0 | 0 | | 2 | 130 | 129 | 128,980392 |
| 12 | 0 | 0 | | 2 | 131 | 129 | 129,972549 |
| 13 | 0 | 0 | | 2 | 131 | 129 | 129,972549 |
| 14 | 0 | 0 | | 2 | 131 | 129 | 129,972549 |
| 15 | 0 | 0 | | 2 | 132 | 129 | 130,964706 |
| 16 | 0 | 0 | | 3 | 132 | 129 | 130,447059 |
| 17 | 0 | 0 | | 3 | 132 | 129 | 130,447059 |
| 18 | 0 | 0 | | 3 | 133 | 129 | 131,435294 |
| 19 | 0 | 0 | | 3 | 133 | 129 | 131,435294 |
| 20 | 0 | 0 | | 3 | 134 | 130 | 132,423529 |
| 21 | 0 | 0 | | 4 | 134 | 130 | 131,898039 |
| 22 | 0 | 0 | | 4 | 134 | 130 | 131,898039 |
| 23 | 0 | 0 | | 4 | 135 | 130 | 132,882353 |
| 24 | 0 | 0 | | 4 | 135 | 130 | 132,882353 |
| 25 | 0 | 0 | | 5 | 136 | 130 | 133,333333 |
| 26 | 0 | 0 | | 5 | 136 | 131 | 133,333333 |
| 27 | 0 | 0 | | 5 | 137 | 131 | 134,313725 |
| 28 | 0 | 0 | | 6 | 138 | 131 | 134,752941 |
| 29 | 0 | 0 | | 6 | 138 | 131 | 134,752941 |
| 30 | 0 | 0 | | 6 | 139 | 131 | 135,729412 |
| 31 | 0 | 0 | | 7 | 139 | 132 | 135,184314 |
| 32 | 0 | 0 | | 7 | 140 | 132 | 136,156863 |
| 33 | 0 | 0 | | 7 | 141 | 132 | 137,129412 |
| 34 | 0 | 0 | | 8 | 141 | 132 | 136,576471 |
| 35 | 0 | 0 | | 8 | 142 | 133 | 137,545098 |
| 36 | 0 | 0 | | 9 | 143 | 133 | 137,952941 |
| 37 | 0 | 0 | | 9 | 143 | 133 | 137,952941 |
| 38 | 0 | 0 | | 9 | 144 | 133 | 138,917647 |
| 39 | 0 | 0 | | 10 | 145 | 134 | 139,313725 |
| 40 | 0 | 0 | | 10 | 146 | 134 | 140,27451 |
| 41 | 0 | 0 | | 11 | 147 | 134 | 140,658824 |
| 42 | 0 | 0 | | 11 | 147 | 135 | 140,658824 |
| 43 | 0 | 0 | | 12 | 148 | 135 | 141,035294 |
| 44 | 0 | 0 | | 12 | 149 | 135 | 141,988235 |

Figure 7

| | | | | | | |
|---|---|---|---|---|---|---|
| 45 | 0 | 0 | 13 | 149 | 135 | 141,403922 |
| 46 | 0 | 0 | 13 | 150 | 136 | 142,352941 |
| 47 | 0 | 0 | 14 | 151 | 136 | 142,709804 |
| 48 | 0 | 0 | 14 | 151 | 136 | 142,709804 |
| 49 | 0 | 0 | 15 | 152 | 137 | 143,058824 |
| 50 | 0 | 0 | 16 | 152 | 137 | 142,462745 |
| 51 | 0 | 0 | 16 | 153 | 138 | 143,4 |
| 52 | 0 | 0 | 17 | 153 | 138 | 142,8 |
| 53 | 0 | 0 | 17 | 154 | 138 | 143,733333 |
| 54 | 0 | 0 | 18 | 154 | 139 | 143,129412 |
| 55 | 0 | 0 | 19 | 154 | 139 | 142,52549 |
| 56 | 0 | 0 | 19 | 155 | 140 | 143,45098 |
| 57 | 0 | 0 | 20 | 155 | 140 | 142,843137 |
| 58 | 0 | 0 | 21 | 155 | 140 | 142,235294 |
| 59 | 0 | 0 | 21 | 156 | 141 | 143,152941 |
| 60 | 0 | 0 | 22 | 156 | 141 | 142,541176 |
| 61 | 0 | 0 | 23 | 156 | 142 | 141,929412 |
| 62 | 0 | 0 | 23 | 157 | 142 | 142,839216 |
| 63 | 0 | 0 | 24 | 157 | 142 | 142,223529 |
| 64 | 0 | 0 | 25 | 157 | 143 | 141,607843 |
| 65 | 0 | 0 | 25 | 158 | 143 | 142,509804 |
| 66 | 0 | 0 | 26 | 158 | 144 | 141,890196 |
| 67 | 0 | 0 | 27 | 158 | 144 | 141,270588 |
| 68 | 0 | 0 | 27 | 158 | 144 | 141,270588 |
| 69 | 0 | 0 | 28 | 159 | 145 | 141,541176 |
| 70 | 0 | 0 | 29 | 159 | 145 | 140,917647 |
| 71 | 0 | 0 | 29 | 159 | 146 | 140,917647 |
| 72 | 0 | 0 | 30 | 160 | 146 | 141,176471 |
| 73 | 0 | 0 | 31 | 160 | 146 | 140,54902 |
| 74 | 0 | 0 | 31 | 160 | 147 | 140,54902 |
| 75 | 0 | 0 | 32 | 161 | 147 | 140,796078 |
| 76 | 0 | 0 | 33 | 161 | 148 | 140,164706 |
| 77 | 0 | 0 | 33 | 161 | 148 | 140,164706 |
| 78 | 0 | 0 | 34 | 161 | 148 | 139,533333 |
| 79 | 0 | 0 | 35 | 162 | 149 | 139,764706 |
| 80 | 0 | 0 | 35 | 162 | 149 | 139,764706 |
| 81 | 0 | 0 | 36 | 162 | 150 | 139,129412 |
| 82 | 0 | 0 | 37 | 163 | 150 | 139,34902 |
| 83 | 0 | 0 | 37 | 163 | 150 | 139,34902 |
| 84 | 0 | 0 | 38 | 163 | 151 | 138,709804 |
| 85 | 0 | 0 | 39 | 164 | 151 | 138,917647 |
| 86 | 0 | 0 | 39 | 164 | 151 | 138,917647 |
| 87 | 0 | 0 | 40 | 164 | 152 | 138,27451 |
| 88 | 0 | 0 | 40 | 164 | 152 | 138,27451 |
| 89 | 0 | 0 | 41 | 165 | 153 | 138,470588 |
| 90 | 0 | 0 | 42 | 165 | 153 | 137,823529 |

Figure 7 (continued)

| | | | | | | |
|---|---|---|---|---|---|---|
| 91 | 0 | 0 | | 42 | 165 | 153 | 137,823529 |
| 92 | 0 | 0 | | 43 | 166 | 154 | 138,007843 |
| 93 | 0 | 0 | | 44 | 166 | 154 | 137,356863 |
| 94 | 0 | 0 | | 44 | 166 | 154 | 137,356863 |
| 95 | 0 | 0 | | 45 | 166 | 155 | 136,705882 |
| 96 | 0 | 0 | | 46 | 167 | 155 | 136,87451 |
| 97 | 0 | 0 | | 46 | 167 | 155 | 136,87451 |
| 98 | 0 | 0 | | 47 | 167 | 156 | 136,219608 |
| 99 | 0 | 0 | | 47 | 168 | 156 | 137,035294 |
| 100 | 0 | 0 | | 48 | 168 | 156 | 136,376471 |
| 101 | 0 | 0 | | 49 | 168 | 157 | 135,717647 |
| 102 | 0 | 0 | | 49 | 168 | 157 | 135,717647 |
| 103 | 0 | 0 | | 50 | 169 | 157 | 135,862745 |
| 104 | 0 | 0 | | 51 | 169 | 158 | 135,2 |
| 105 | 0 | 0 | | 51 | 169 | 158 | 135,2 |
| 106 | 0 | 0 | | 52 | 170 | 159 | 135,333333 |
| 107 | 0 | 0 | | 52 | 170 | 159 | 135,333333 |
| 108 | 0 | 0 | | 53 | 170 | 159 | 134,666667 |
| 109 | 0 | 0 | | 54 | 170 | 160 | 134 |
| 110 | 0 | 0 | | 54 | 171 | 160 | 134,788235 |
| 111 | 0 | 0 | | 55 | 171 | 160 | 134,117647 |
| 112 | 0 | 0 | | 55 | 171 | 161 | 134,117647 |
| 113 | 0 | 0 | | 56 | 171 | 161 | 133,447059 |
| 114 | 0 | 0 | | 57 | 172 | 161 | 133,552941 |
| 115 | 0 | 0 | | 57 | 172 | 161 | 133,552941 |
| 116 | 0 | 0 | | 58 | 172 | 162 | 132,878431 |
| 117 | 0 | 0 | | 58 | 173 | 162 | 133,65098 |
| 118 | 0 | 0 | | 59 | 173 | 162 | 132,972549 |
| 119 | 0 | 0 | | 60 | 173 | 163 | 132,294118 |
| 120 | 0 | 0 | | 60 | 173 | 163 | 132,294118 |
| 121 | 0 | 0 | | 61 | 174 | 163 | 132,376471 |
| 122 | 0 | 0 | | 62 | 174 | 164 | 131,694118 |
| 123 | 0 | 0 | | 62 | 174 | 164 | 131,694118 |
| 124 | 0 | 0 | | 63 | 174 | 164 | 131,011765 |
| 125 | 0 | 0 | | 63 | 175 | 165 | 131,764706 |
| 126 | 0 | 0 | | 64 | 175 | 165 | 131,078431 |
| 127 | 0 | 0 | | 65 | 175 | 165 | 130,392157 |
| 128 | 0 | 0 | | 65 | 176 | 166 | 131,137255 |
| 129 | 0 | 0 | | 66 | 176 | 166 | 130,447059 |
| 130 | 0 | 0 | | 66 | 176 | 166 | 130,447059 |
| 131 | 0 | 0 | | 67 | 176 | 166 | 129,756863 |
| 132 | 0 | 0 | | 67 | 177 | 167 | 130,494118 |
| 133 | 0 | 0 | | 68 | 177 | 167 | 129,8 |
| 134 | 0 | 0 | | 69 | 177 | 167 | 129,105882 |
| 135 | 0 | 0 | | 69 | 177 | 168 | 129,105882 |
| 136 | 0 | 0 | | 70 | 178 | 168 | 129,137255 |

Figure 7 (continued)

| | | | | | | |
|---|---|---|---|---|---|---|
| 137 | 0 | 0 | | 70 | 178 | 168 | 129,137255 |
| 138 | 0 | 0 | | 71 | 178 | 169 | 128,439216 |
| 139 | 0 | 0 | | 72 | 179 | 169 | 128,458824 |
| 140 | 0 | 0 | | 72 | 179 | 169 | 128,458824 |
| 141 | 0 | 0 | | 73 | 179 | 169 | 127,756863 |
| 142 | 0 | 0 | | 73 | 179 | 170 | 127,756863 |
| 143 | 0 | 0 | | 74 | 180 | 170 | 127,764706 |
| 144 | 0 | 0 | | 75 | 180 | 170 | 127,058824 |
| 145 | 0 | 0 | | 75 | 180 | 170 | 127,058824 |
| 146 | 0 | 0 | | 76 | 180 | 171 | 126,352941 |
| 147 | 0 | 0 | | 76 | 181 | 171 | 127,054902 |
| 148 | 0 | 0 | | 77 | 181 | 171 | 126,345098 |
| 149 | 0 | 0 | | 77 | 181 | 172 | 126,345098 |
| 150 | 0 | 0 | | 78 | 181 | 172 | 125,635294 |
| 151 | 0 | 0 | | 79 | 182 | 172 | 125,615686 |
| 152 | 0 | 0 | | 79 | 182 | 172 | 125,615686 |
| 153 | 0 | 0 | | 80 | 182 | 173 | 124,901961 |
| 154 | 0 | 0 | | 80 | 182 | 173 | 124,901961 |
| 155 | 0 | 0 | | 81 | 183 | 173 | 124,870588 |
| 156 | 0 | 0 | | 81 | 183 | 173 | 124,870588 |
| 157 | 0 | 0 | | 82 | 183 | 174 | 124,152941 |
| 158 | 0 | 0 | | 83 | 184 | 174 | 124,109804 |
| 159 | 0 | 0 | | 83 | 184 | 174 | 124,109804 |
| 160 | 0 | 0 | | 84 | 184 | 174 | 123,388235 |
| 161 | 0 | 0 | | 84 | 184 | 175 | 123,388235 |
| 162 | 0 | 0 | | 85 | 185 | 175 | 123,333333 |
| 163 | 0 | 0 | | 86 | 185 | 175 | 122,607843 |
| 164 | 0 | 0 | | 86 | 185 | 175 | 122,607843 |
| 165 | 0 | 0 | | 87 | 185 | 176 | 121,882353 |
| 166 | 0 | 0 | | 87 | 186 | 176 | 122,541176 |
| 167 | 0 | 0 | | 88 | 186 | 176 | 121,811765 |
| 168 | 0 | 0 | | 88 | 186 | 176 | 121,811765 |
| 169 | 0 | 0 | | 89 | 186 | 177 | 121,082353 |
| 170 | 0 | 0 | | 89 | 187 | 177 | 121,733333 |
| 171 | 0 | 0 | | 90 | 187 | 177 | 121 |
| 172 | 0 | 0 | | 91 | 187 | 177 | 120,266667 |
| 173 | 0 | 0 | | 91 | 187 | 178 | 120,266667 |
| 174 | 0 | 0 | | 92 | 188 | 178 | 120,172549 |
| 175 | 0 | 0 | | 92 | 188 | 178 | 120,172549 |
| 176 | 0 | 0 | | 93 | 188 | 178 | 119,435294 |
| 177 | 0 | 0 | | 93 | 188 | 179 | 119,435294 |
| 178 | 0 | 0 | | 94 | 189 | 179 | 119,329412 |
| 179 | 0 | 0 | | 95 | 189 | 179 | 118,588235 |
| 180 | 0 | 0 | | 95 | 189 | 179 | 118,588235 |
| 181 | 0 | 0 | | 96 | 189 | 179 | 117,847059 |
| 182 | 0 | 0 | | 96 | 190 | 180 | 118,470588 |

Figure 7 (continued)

| | | | | | | |
|---|---|---|---|---|---|---|
| 183 | 0 | 0 | | 97 | 190 | 180 | 117,72549 |
| 184 | 0 | 0 | | 97 | 190 | 180 | 117,72549 |
| 185 | 0 | 0 | | 98 | 190 | 180 | 116,980392 |
| 186 | 0 | 0 | | 98 | 191 | 181 | 117,596078 |
| 187 | 0 | 0 | | 99 | 191 | 181 | 116,847059 |
| 188 | 0 | 0 | | 100 | 191 | 181 | 116,098039 |
| 189 | 0 | 0 | | 100 | 191 | 181 | 116,098039 |
| 190 | 0 | 0 | | 101 | 192 | 181 | 115,952941 |
| 191 | 0 | 0 | | 101 | 192 | 182 | 115,952941 |
| 192 | 0 | 0 | | 102 | 192 | 182 | 115,2 |
| 193 | 0 | 0 | | 102 | 192 | 182 | 115,2 |
| 194 | 0 | 0 | | 103 | 193 | 182 | 115,043137 |
| 195 | 0 | 0 | | 103 | 193 | 182 | 115,043137 |
| 196 | 0 | 0 | | 104 | 193 | 183 | 114,286275 |
| 197 | 0 | 0 | | 105 | 193 | 183 | 113,529412 |
| 198 | 0 | 0 | | 105 | 194 | 183 | 114,117647 |
| 199 | 0 | 0 | | 106 | 194 | 183 | 113,356863 |
| 200 | 0 | 0 | | 106 | 194 | 183 | 113,356863 |
| 201 | 0 | 0 | | 107 | 194 | 184 | 112,596078 |
| 202 | 0 | 0 | | 107 | 195 | 184 | 113,176471 |
| 203 | 0 | 0 | | 108 | 195 | 184 | 112,411765 |
| 204 | 0 | 0 | | 108 | 195 | 184 | 112,411765 |
| 205 | 0 | 0 | | 109 | 195 | 185 | 111,647059 |
| 206 | 0 | 0 | | 110 | 196 | 185 | 111,45098 |
| 207 | 0 | 0 | | 110 | 196 | 185 | 111,45098 |
| 208 | 0 | 0 | | 111 | 196 | 185 | 110,682353 |
| 209 | 0 | 0 | | 111 | 196 | 185 | 110,682353 |
| 210 | 0 | 0 | | 112 | 197 | 186 | 110,47451 |
| 211 | 0 | 0 | | 112 | 197 | 186 | 110,47451 |
| 212 | 0 | 0 | | 113 | 197 | 186 | 109,701961 |
| 213 | 0 | 0 | | 113 | 197 | 186 | 109,701961 |
| 214 | 0 | 0 | | 114 | 198 | 186 | 109,482353 |
| 215 | 0 | 0 | | 114 | 198 | 187 | 109,482353 |
| 216 | 0 | 0 | | 115 | 198 | 187 | 108,705882 |
| 217 | 0 | 0 | | 115 | 198 | 187 | 108,705882 |
| 218 | 0 | 0 | | 116 | 199 | 187 | 108,47451 |
| 219 | 0 | 0 | | 117 | 199 | 187 | 107,694118 |
| 220 | 0 | 0 | | 117 | 199 | 188 | 107,694118 |
| 221 | 0 | 0 | | 118 | 199 | 188 | 106,913725 |
| 222 | 0 | 0 | | 118 | 200 | 188 | 107,45098 |
| 223 | 0 | 0 | | 119 | 200 | 188 | 106,666667 |
| 224 | 0 | 0 | | 119 | 200 | 188 | 106,666667 |
| 225 | 0 | 0 | | 120 | 200 | 189 | 105,882353 |
| 226 | 0 | 0 | | 120 | 201 | 189 | 106,411765 |
| 227 | 0 | 0 | | 121 | 201 | 189 | 105,623529 |
| 228 | 0 | 0 | | 121 | 201 | 189 | 105,623529 |

Figure 7 (continued)

| | | | | | | |
|---|---|---|---|---|---|---|
| 229 | 0 | 0 | 122 | 201 | 189 | 104,835294 |
| 230 | 0 | 0 | 122 | 202 | 190 | 105,356863 |
| 231 | 0 | 0 | 123 | 202 | 190 | 104,564706 |
| 232 | 0 | 0 | 124 | 202 | 190 | 103,772549 |
| 233 | 0 | 0 | 124 | 202 | 190 | 103,772549 |
| 234 | 0 | 0 | 125 | 203 | 190 | 103,490196 |
| 235 | 0 | 0 | 125 | 203 | 191 | 103,490196 |
| 236 | 0 | 0 | 126 | 203 | 191 | 102,694118 |
| 237 | 0 | 0 | 126 | 203 | 191 | 102,694118 |
| 238 | 0 | 0 | 127 | 204 | 191 | 102,4 |
| 239 | 0 | 0 | 127 | 204 | 192 | 102,4 |
| 240 | 0 | 0 | 128 | 204 | 192 | 101,6 |
| 241 | 0 | 0 | 128 | 204 | 192 | 101,6 |
| 242 | 0 | 0 | 129 | 205 | 192 | 101,294118 |
| 243 | 0 | 0 | 129 | 205 | 192 | 101,294118 |
| 244 | 0 | 0 | 130 | 205 | 193 | 100,490196 |
| 245 | 0 | 0 | 130 | 205 | 193 | 100,490196 |
| 246 | 0 | 0 | 131 | 205 | 193 | 99,6862745 |
| 247 | 0 | 0 | 132 | 206 | 193 | 99,3647059 |
| 248 | 0 | 0 | 132 | 206 | 193 | 99,3647059 |
| 249 | 0 | 0 | 133 | 206 | 194 | 98,5568627 |
| 250 | 0 | 0 | 133 | 206 | 194 | 98,5568627 |
| 251 | 0 | 0 | 134 | 207 | 194 | 98,2235294 |
| 252 | 0 | 0 | 134 | 207 | 194 | 98,2235294 |
| 253 | 0 | 0 | 135 | 207 | 194 | 97,4117647 |
| 254 | 0 | 0 | 135 | 207 | 195 | 97,4117647 |
| 255 | 0 | 0 | 136 | 208 | 195 | 97,0666667 |
| 255 | 1 | 1 | 136 | 208 | 194 | 97,0666667 |
| 255 | 2 | 2 | 136 | 207 | 194 | 96,6 |
| 255 | 3 | 3 | 136 | 207 | 194 | 96,6 |
| 255 | 4 | 4 | 136 | 207 | 194 | 96,6 |
| 255 | 5 | 5 | 136 | 207 | 194 | 96,6 |
| 255 | 6 | 6 | 136 | 207 | 193 | 96,6 |
| 255 | 7 | 7 | 136 | 207 | 193 | 96,6 |
| 255 | 8 | 8 | 136 | 207 | 193 | 96,6 |
| 255 | 9 | 9 | 136 | 207 | 193 | 96,6 |
| 255 | 10 | 10 | 136 | 207 | 192 | 96,6 |
| 255 | 11 | 11 | 136 | 207 | 192 | 96,6 |
| 255 | 12 | 12 | 137 | 207 | 192 | 95,7882353 |
| 255 | 13 | 13 | 137 | 207 | 192 | 95,7882353 |
| 255 | 14 | 14 | 137 | 207 | 191 | 95,7882353 |
| 255 | 15 | 15 | 137 | 207 | 191 | 95,7882353 |
| 255 | 16 | 16 | 137 | 207 | 191 | 95,7882353 |
| 255 | 17 | 17 | 137 | 206 | 191 | 95,3254902 |
| 255 | 18 | 18 | 137 | 206 | 190 | 95,3254902 |
| 255 | 19 | 19 | 137 | 206 | 190 | 95,3254902 |

Figure 7 (continued)

| | | | | | | |
|---|---|---|---|---|---|---|
| 255 | 20 | 20 | | 137 | 206 | 190 | 95,3254902 |
| 255 | 21 | 21 | | 137 | 206 | 189 | 95,3254902 |
| 255 | 22 | 22 | | 137 | 206 | 189 | 95,3254902 |
| 255 | 23 | 23 | | 138 | 206 | 189 | 94,5176471 |
| 255 | 24 | 24 | | 138 | 206 | 188 | 94,5176471 |
| 255 | 25 | 25 | | 138 | 206 | 188 | 94,5176471 |
| 255 | 26 | 26 | | 138 | 206 | 188 | 94,5176471 |
| 255 | 27 | 27 | | 138 | 205 | 187 | 94,0588235 |
| 255 | 28 | 28 | | 138 | 205 | 187 | 94,0588235 |
| 255 | 29 | 29 | | 138 | 205 | 187 | 94,0588235 |
| 255 | 30 | 30 | | 139 | 205 | 186 | 93,254902 |
| 255 | 31 | 31 | | 139 | 205 | 186 | 93,254902 |
| 255 | 32 | 32 | | 139 | 205 | 186 | 93,254902 |
| 255 | 33 | 33 | | 139 | 205 | 185 | 93,254902 |
| 255 | 34 | 34 | | 139 | 204 | 185 | 92,8 |
| 255 | 35 | 35 | | 139 | 204 | 184 | 92,8 |
| 255 | 36 | 36 | | 140 | 204 | 184 | 92 |
| 255 | 37 | 37 | | 140 | 204 | 184 | 92 |
| 255 | 38 | 38 | | 140 | 204 | 183 | 92 |
| 255 | 39 | 39 | | 140 | 204 | 183 | 92 |
| 255 | 40 | 40 | | 140 | 203 | 182 | 91,5490196 |
| 255 | 41 | 41 | | 140 | 203 | 182 | 91,5490196 |
| 255 | 42 | 42 | | 141 | 203 | 182 | 90,7529412 |
| 255 | 43 | 43 | | 141 | 203 | 181 | 90,7529412 |
| 255 | 44 | 44 | | 141 | 203 | 181 | 90,7529412 |
| 255 | 45 | 45 | | 141 | 203 | 180 | 90,7529412 |
| 255 | 46 | 46 | | 142 | 202 | 180 | 89,5137255 |
| 255 | 47 | 47 | | 142 | 202 | 179 | 89,5137255 |
| 255 | 48 | 48 | | 142 | 202 | 179 | 89,5137255 |
| 255 | 49 | 49 | | 142 | 202 | 179 | 89,5137255 |
| 255 | 50 | 50 | | 142 | 201 | 178 | 89,0705882 |
| 255 | 51 | 51 | | 143 | 201 | 178 | 88,2823529 |
| 255 | 52 | 52 | | 143 | 201 | 177 | 88,2823529 |
| 255 | 53 | 53 | | 143 | 201 | 177 | 88,2823529 |
| 255 | 54 | 54 | | 143 | 201 | 176 | 88,2823529 |
| 255 | 55 | 55 | | 144 | 200 | 176 | 87,0588235 |
| 255 | 56 | 56 | | 144 | 200 | 176 | 87,0588235 |
| 255 | 57 | 57 | | 144 | 200 | 175 | 87,0588235 |
| 255 | 58 | 58 | | 145 | 200 | 175 | 86,2745098 |
| 255 | 59 | 59 | | 145 | 199 | 174 | 85,8431373 |
| 255 | 60 | 60 | | 145 | 199 | 174 | 85,8431373 |
| 255 | 61 | 61 | | 145 | 199 | 174 | 85,8431373 |
| 255 | 62 | 62 | | 146 | 199 | 173 | 85,0627451 |
| 255 | 63 | 63 | | 146 | 198 | 173 | 84,6352941 |
| 255 | 64 | 64 | | 146 | 198 | 172 | 84,6352941 |
| 255 | 65 | 65 | | 147 | 198 | 172 | 83,8588235 |

Figure 7 (continued)

| | | | | | | |
|---|---|---|---|---|---|---|
| 255 | 66 | 66 | | 147 | 198 | 171 | 83,8588235 |
| 255 | 67 | 67 | | 147 | 197 | 171 | 83,4352941 |
| 255 | 68 | 68 | | 148 | 197 | 171 | 82,6627451 |
| 255 | 69 | 69 | | 148 | 197 | 170 | 82,6627451 |
| 255 | 70 | 70 | | 148 | 196 | 170 | 82,2431373 |
| 255 | 71 | 71 | | 149 | 196 | 169 | 81,4745098 |
| 255 | 72 | 72 | | 149 | 196 | 169 | 81,4745098 |
| 255 | 73 | 73 | | 149 | 196 | 169 | 81,4745098 |
| 255 | 74 | 74 | | 150 | 195 | 168 | 80,2941176 |
| 255 | 75 | 75 | | 150 | 195 | 168 | 80,2941176 |
| 255 | 76 | 76 | | 150 | 195 | 167 | 80,2941176 |
| 255 | 77 | 77 | | 151 | 194 | 167 | 79,1215686 |
| 255 | 78 | 78 | | 151 | 194 | 167 | 79,1215686 |
| 255 | 79 | 79 | | 151 | 194 | 166 | 79,1215686 |
| 255 | 80 | 80 | | 152 | 193 | 166 | 77,9568627 |
| 255 | 81 | 81 | | 152 | 193 | 166 | 77,9568627 |
| 255 | 82 | 82 | | 152 | 193 | 165 | 77,9568627 |
| 255 | 83 | 83 | | 153 | 192 | 165 | 76,8 |
| 255 | 84 | 84 | | 153 | 192 | 164 | 76,8 |
| 255 | 85 | 85 | | 154 | 192 | 164 | 76,0470588 |
| 255 | 86 | 86 | | 154 | 191 | 164 | 75,6509804 |
| 255 | 87 | 87 | | 154 | 191 | 163 | 75,6509804 |
| 255 | 88 | 88 | | 155 | 191 | 163 | 74,9019608 |
| 255 | 89 | 89 | | 155 | 190 | 163 | 74,5098039 |
| 255 | 90 | 90 | | 156 | 190 | 162 | 73,7647059 |
| 255 | 91 | 91 | | 156 | 190 | 162 | 73,7647059 |
| 255 | 92 | 92 | | 157 | 189 | 161 | 72,6352941 |
| 255 | 93 | 93 | | 157 | 189 | 161 | 72,6352941 |
| 255 | 94 | 94 | | 157 | 189 | 161 | 72,6352941 |
| 255 | 95 | 95 | | 158 | 188 | 160 | 71,5137255 |
| 255 | 96 | 96 | | 158 | 188 | 160 | 71,5137255 |
| 255 | 97 | 97 | | 159 | 188 | 160 | 70,7764706 |
| 255 | 98 | 98 | | 159 | 187 | 159 | 70,4 |
| 255 | 99 | 99 | | 160 | 187 | 159 | 69,6666667 |
| 255 | 100 | 100 | | 160 | 186 | 159 | 69,2941176 |
| 255 | 101 | 101 | | 160 | 186 | 158 | 69,2941176 |
| 255 | 102 | 102 | | 161 | 186 | 158 | 68,5647059 |
| 255 | 103 | 103 | | 161 | 185 | 158 | 68,1960784 |
| 255 | 104 | 104 | | 162 | 185 | 157 | 67,4705882 |
| 255 | 105 | 105 | | 162 | 185 | 157 | 67,4705882 |
| 255 | 106 | 106 | | 163 | 184 | 157 | 66,3843137 |
| 255 | 107 | 107 | | 163 | 184 | 156 | 66,3843137 |
| 255 | 108 | 108 | | 164 | 184 | 156 | 65,6627451 |
| 255 | 109 | 109 | | 164 | 183 | 156 | 65,3058824 |
| 255 | 110 | 110 | | 165 | 183 | 155 | 64,5882353 |
| 255 | 111 | 111 | | 165 | 182 | 155 | 64,2352941 |

Figure 7 (continued)

| | | | | | | |
|---|---|---|---|---|---|---|
| 255 | 112 | 112 | | 166 | 182 | 155 | 63,5215686 |
| 255 | 113 | 113 | | 166 | 182 | 155 | 63,5215686 |
| 255 | 114 | 114 | | 167 | 181 | 154 | 62,4627451 |
| 255 | 115 | 115 | | 167 | 181 | 154 | 62,4627451 |
| 255 | 116 | 116 | | 168 | 180 | 154 | 61,4117647 |
| 255 | 117 | 117 | | 168 | 180 | 153 | 61,4117647 |
| 255 | 118 | 118 | | 169 | 180 | 153 | 60,7058824 |
| 255 | 119 | 119 | | 169 | 179 | 153 | 60,3686275 |
| 255 | 120 | 120 | | 170 | 179 | 152 | 59,6666667 |
| 255 | 121 | 121 | | 170 | 178 | 152 | 59,3333333 |
| 255 | 122 | 122 | | 171 | 178 | 152 | 58,6352941 |
| 255 | 123 | 123 | | 171 | 178 | 152 | 58,6352941 |
| 255 | 124 | 124 | | 172 | 177 | 151 | 57,6117647 |
| 255 | 125 | 125 | | 172 | 177 | 151 | 57,6117647 |
| 255 | 126 | 126 | | 173 | 176 | 151 | 56,5960784 |
| 255 | 127 | 127 | | 173 | 176 | 150 | 56,5960784 |
| 255 | 128 | 128 | | 174 | 176 | 150 | 55,9058824 |
| 255 | 129 | 129 | | 174 | 175 | 150 | 55,5882353 |
| 255 | 130 | 130 | | 175 | 175 | 150 | 54,9019608 |
| 255 | 131 | 131 | | 176 | 175 | 149 | 54,2156863 |
| 255 | 132 | 132 | | 176 | 174 | 149 | 53,9058824 |
| 255 | 133 | 133 | | 177 | 174 | 149 | 53,2235294 |
| 255 | 134 | 134 | | 177 | 173 | 149 | 52,9176471 |
| 255 | 135 | 135 | | 178 | 173 | 148 | 52,2392157 |
| 255 | 136 | 136 | | 178 | 172 | 148 | 51,9372549 |
| 255 | 137 | 137 | | 179 | 172 | 148 | 51,2627451 |
| 255 | 138 | 138 | | 179 | 172 | 148 | 51,2627451 |
| 255 | 139 | 139 | | 180 | 171 | 147 | 50,2941176 |
| 255 | 140 | 140 | | 181 | 171 | 147 | 49,6235294 |
| 255 | 141 | 141 | | 181 | 170 | 147 | 49,3333333 |
| 255 | 142 | 142 | | 182 | 170 | 147 | 48,6666667 |
| 255 | 143 | 143 | | 182 | 170 | 146 | 48,6666667 |
| 255 | 144 | 144 | | 183 | 169 | 146 | 47,7176471 |
| 255 | 145 | 145 | | 183 | 169 | 146 | 47,7176471 |
| 255 | 146 | 146 | | 184 | 168 | 146 | 46,7764706 |
| 255 | 147 | 147 | | 185 | 168 | 145 | 46,1176471 |
| 255 | 148 | 148 | | 185 | 168 | 145 | 46,1176471 |
| 255 | 149 | 149 | | 186 | 167 | 145 | 45,1882353 |
| 255 | 150 | 150 | | 186 | 167 | 145 | 45,1882353 |
| 255 | 151 | 151 | | 187 | 166 | 144 | 44,2666667 |
| 255 | 152 | 152 | | 188 | 166 | 144 | 43,6156863 |
| 255 | 153 | 153 | | 188 | 166 | 144 | 43,6156863 |
| 255 | 154 | 154 | | 189 | 165 | 144 | 42,7058824 |
| 255 | 155 | 155 | | 189 | 165 | 144 | 42,7058824 |
| 255 | 156 | 156 | | 190 | 164 | 143 | 41,8039216 |
| 255 | 157 | 157 | | 190 | 164 | 143 | 41,8039216 |

Figure 7 (continued)

| | | | | | | |
|---|---|---|---|---|---|---|
| 255 | 158 | 158 | | 191 | 164 | 143 | 41,1607843 |
| 255 | 159 | 159 | | 192 | 163 | 143 | 40,2705882 |
| 255 | 160 | 160 | | 192 | 163 | 142 | 40,2705882 |
| 255 | 161 | 161 | | 193 | 162 | 142 | 39,3882353 |
| 255 | 162 | 162 | | 194 | 162 | 142 | 38,7529412 |
| 255 | 163 | 163 | | 194 | 162 | 142 | 38,7529412 |
| 255 | 164 | 164 | | 195 | 161 | 142 | 37,8823529 |
| 255 | 165 | 165 | | 195 | 161 | 141 | 37,8823529 |
| 255 | 166 | 166 | | 196 | 160 | 141 | 37,0196078 |
| 255 | 167 | 167 | | 197 | 160 | 141 | 36,3921569 |
| 255 | 168 | 168 | | 197 | 160 | 141 | 36,3921569 |
| 255 | 169 | 169 | | 198 | 159 | 141 | 35,5411765 |
| 255 | 170 | 170 | | 198 | 159 | 140 | 35,5411765 |
| 255 | 171 | 171 | | 199 | 158 | 140 | 34,6980392 |
| 255 | 172 | 172 | | 200 | 158 | 140 | 34,0784314 |
| 255 | 173 | 173 | | 200 | 158 | 140 | 34,0784314 |
| 255 | 174 | 174 | | 201 | 157 | 140 | 33,2470588 |
| 255 | 175 | 175 | | 202 | 157 | 139 | 32,6313725 |
| 255 | 176 | 176 | | 202 | 156 | 139 | 32,4235294 |
| 255 | 177 | 177 | | 203 | 156 | 139 | 31,8117647 |
| 255 | 178 | 178 | | 203 | 156 | 139 | 31,8117647 |
| 255 | 179 | 179 | | 204 | 155 | 139 | 31 |
| 255 | 180 | 180 | | 205 | 155 | 138 | 30,3921569 |
| 255 | 181 | 181 | | 205 | 154 | 138 | 30,1960784 |
| 255 | 182 | 182 | | 206 | 154 | 138 | 29,5921569 |
| 255 | 183 | 183 | | 207 | 154 | 138 | 28,9882353 |
| 255 | 184 | 184 | | 207 | 153 | 138 | 28,8 |
| 255 | 185 | 185 | | 208 | 153 | 138 | 28,2 |
| 255 | 186 | 186 | | 209 | 152 | 137 | 27,4196078 |
| 255 | 187 | 187 | | 209 | 152 | 137 | 27,4196078 |
| 255 | 188 | 188 | | 210 | 152 | 137 | 26,8235294 |
| 255 | 189 | 189 | | 211 | 151 | 137 | 26,054902 |
| 255 | 190 | 190 | | 211 | 151 | 137 | 26,054902 |
| 255 | 191 | 191 | | 212 | 150 | 136 | 25,2941176 |
| 255 | 192 | 192 | | 212 | 150 | 136 | 25,2941176 |
| 255 | 193 | 193 | | 213 | 150 | 136 | 24,7058824 |
| 255 | 194 | 194 | | 214 | 149 | 136 | 23,9568627 |
| 255 | 195 | 195 | | 214 | 149 | 136 | 23,9568627 |
| 255 | 196 | 196 | | 215 | 149 | 136 | 23,372549 |
| 255 | 197 | 197 | | 216 | 148 | 135 | 22,6352941 |
| 255 | 198 | 198 | | 216 | 148 | 135 | 22,6352941 |
| 255 | 199 | 199 | | 217 | 147 | 135 | 21,9058824 |
| 255 | 200 | 200 | | 218 | 147 | 135 | 21,3294118 |
| 255 | 201 | 201 | | 218 | 147 | 135 | 21,3294118 |
| 255 | 202 | 202 | | 219 | 146 | 135 | 20,6117647 |
| 255 | 203 | 203 | | 220 | 146 | 135 | 20,0392157 |

Figure 7 (continued)

| | | | | | | |
|---|---|---|---|---|---|---|
| 255 | 204 | 204 | | 220 | 146 | 134 | 20,0392157 |
| 255 | 205 | 205 | | 221 | 145 | 134 | 19,3333333 |
| 255 | 206 | 206 | | 222 | 145 | 134 | 18,7647059 |
| 255 | 207 | 207 | | 222 | 144 | 134 | 18,6352941 |
| 255 | 208 | 208 | | 223 | 144 | 134 | 18,0705882 |
| 255 | 209 | 209 | | 224 | 144 | 134 | 17,5058824 |
| 255 | 210 | 210 | | 224 | 143 | 133 | 17,3843137 |
| 255 | 211 | 211 | | 225 | 143 | 133 | 16,8235294 |
| 255 | 212 | 212 | | 226 | 143 | 133 | 16,2627451 |
| 255 | 213 | 213 | | 226 | 142 | 133 | 16,1490196 |
| 255 | 214 | 214 | | 227 | 142 | 133 | 15,5921569 |
| 255 | 215 | 215 | | 228 | 141 | 133 | 14,9294118 |
| 255 | 216 | 216 | | 228 | 141 | 133 | 14,9294118 |
| 255 | 217 | 217 | | 229 | 141 | 132 | 14,3764706 |
| 255 | 218 | 218 | | 230 | 140 | 132 | 13,7254902 |
| 255 | 219 | 219 | | 230 | 140 | 132 | 13,7254902 |
| 255 | 220 | 220 | | 231 | 140 | 132 | 13,1764706 |
| 255 | 221 | 221 | | 232 | 139 | 132 | 12,5372549 |
| 255 | 222 | 222 | | 232 | 139 | 132 | 12,5372549 |
| 255 | 223 | 223 | | 233 | 139 | 132 | 11,9921569 |
| 255 | 224 | 224 | | 234 | 138 | 131 | 11,3647059 |
| 255 | 225 | 225 | | 234 | 138 | 131 | 11,3647059 |
| 255 | 226 | 226 | | 235 | 137 | 131 | 10,745098 |
| 255 | 227 | 227 | | 236 | 137 | 131 | 10,2078431 |
| 255 | 228 | 228 | | 236 | 137 | 131 | 10,2078431 |
| 255 | 229 | 229 | | 237 | 136 | 131 | 9,6 |
| 255 | 230 | 230 | | 238 | 136 | 131 | 9,06666667 |
| 255 | 231 | 231 | | 238 | 136 | 130 | 9,06666667 |
| 255 | 232 | 232 | | 239 | 135 | 130 | 8,47058824 |
| 255 | 233 | 233 | | 240 | 135 | 130 | 7,94117647 |
| 255 | 234 | 234 | | 241 | 135 | 130 | 7,41176471 |
| 255 | 235 | 235 | | 241 | 134 | 130 | 7,35686275 |
| 255 | 236 | 236 | | 242 | 134 | 130 | 6,83137255 |
| 255 | 237 | 237 | | 243 | 134 | 130 | 6,30588235 |
| 255 | 238 | 238 | | 243 | 133 | 130 | 6,25882353 |
| 255 | 239 | 239 | | 244 | 133 | 129 | 5,7372549 |
| 255 | 240 | 240 | | 245 | 133 | 129 | 5,21568627 |
| 255 | 241 | 241 | | 245 | 132 | 129 | 5,17647059 |
| 255 | 242 | 242 | | 246 | 132 | 129 | 4,65882353 |
| 255 | 243 | 243 | | 247 | 132 | 129 | 4,14117647 |
| 255 | 244 | 244 | | 247 | 131 | 129 | 4,10980392 |
| 255 | 245 | 245 | | 248 | 131 | 129 | 3,59607843 |
| 255 | 246 | 246 | | 249 | 131 | 129 | 3,08235294 |
| 255 | 247 | 247 | | 249 | 130 | 128 | 3,05882353 |
| 255 | 248 | 248 | | 250 | 130 | 128 | 2,54901961 |
| 255 | 249 | 249 | | 251 | 129 | 128 | 2,02352941 |

| R | G | B | | L | A | B | (255-L)*b |
|---|---|---|---|---|---|---|---|
| 0 | 0 | 0 | | 0 | 0 | 0 | 0 |
| 1 | 1 | 0 | | 8 | 0 | 5 | 4,843137255 |
| 2 | 1 | 0 | | 10 | 2 | 6 | 5,764705882 |
| 3 | 2 | 0 | | 19 | 0 | 11 | 10,18039216 |
| 4 | 2 | 0 | | 21 | 3 | 12 | 11,01176471 |
| 5 | 3 | 0 | | 28 | 1 | 16 | 14,24313725 |
| 6 | 3 | 0 | | 29 | 3 | 17 | 15,06666667 |
| 7 | 4 | 0 | | 35 | 2 | 20 | 17,25490196 |
| 8 | 4 | 0 | | 37 | 4 | 21 | 17,95294118 |
| 9 | 5 | 0 | | 41 | 2 | 24 | 20,14117647 |
| 10 | 5 | 0 | | 43 | 4 | 24 | 19,95294118 |
| 11 | 6 | 0 | | 47 | 3 | 26 | 21,20784314 |
| 12 | 6 | 0 | | 48 | 4 | 27 | 21,91764706 |
| 13 | 6 | 0 | | 49 | 6 | 27 | 21,81176471 |
| 14 | 7 | 0 | | 52 | 5 | 29 | 23,08627451 |
| 15 | 7 | 0 | | 53 | 6 | 30 | 23,76470588 |
| 16 | 8 | 0 | | 57 | 5 | 31 | 24,07058824 |
| 17 | 8 | 0 | | 57 | 6 | 32 | 24,84705882 |
| 18 | 9 | 0 | | 61 | 5 | 33 | 25,10588235 |
| 19 | 9 | 0 | | 61 | 6 | 33 | 25,10588235 |
| 20 | 10 | 0 | | 64 | 5 | 35 | 26,21568627 |
| 21 | 11 | 0 | | 67 | 4 | 36 | 26,54117647 |
| 22 | 11 | 0 | | 68 | 5 | 36 | 26,4 |
| 23 | 12 | 0 | | 70 | 5 | 37 | 26,84313725 |
| 24 | 12 | 0 | | 71 | 6 | 37 | 26,69803922 |
| 25 | 13 | 0 | | 73 | 5 | 38 | 27,12156863 |
| 26 | 13 | 0 | | 74 | 6 | 38 | 26,97254902 |
| 27 | 14 | 0 | | 76 | 5 | 39 | 27,37647059 |
| 28 | 14 | 0 | | 77 | 6 | 39 | 27,22352941 |
| 29 | 15 | 0 | | 79 | 5 | 40 | 27,60784314 |
| 30 | 15 | 0 | | 79 | 6 | 40 | 27,60784314 |
| 31 | 16 | 0 | | 82 | 5 | 41 | 27,81568627 |
| 32 | 16 | 0 | | 82 | 6 | 41 | 27,81568627 |
| 33 | 17 | 0 | | 84 | 6 | 42 | 28,16470588 |
| 34 | 17 | 0 | | 85 | 6 | 42 | 28 |
| 35 | 18 | 0 | | 86 | 6 | 43 | 28,49803922 |
| 36 | 18 | 0 | | 87 | 6 | 43 | 28,32941176 |
| 37 | 19 | 0 | | 89 | 6 | 44 | 28,64313725 |
| 38 | 19 | 0 | | 89 | 6 | 44 | 28,64313725 |
| 39 | 20 | 0 | | 91 | 6 | 44 | 28,29803922 |
| 40 | 20 | 0 | | 91 | 7 | 44 | 28,29803922 |
| 41 | 21 | 0 | | 93 | 6 | 45 | 28,58823529 |
| 42 | 21 | 0 | | 94 | 7 | 45 | 28,41176471 |
| 43 | 22 | 0 | | 95 | 6 | 46 | 28,8627451 |
| 44 | 22 | 0 | | 96 | 7 | 46 | 28,68235294 |
| 45 | 23 | 0 | | 97 | 6 | 46 | 28,50196078 |
| 46 | 23 | 0 | | 98 | 7 | 47 | 28,9372549 |
| 47 | 24 | 0 | | 99 | 6 | 47 | 28,75294118 |
| 48 | 24 | 0 | | 100 | 7 | 47 | 28,56862745 |
| 49 | 25 | 0 | | 101 | 7 | 48 | 28,98823529 |

Figure 9

| | | | | | | |
|---|---|---|---|---|---|---|
| 50 | 25 | 0 | 102 | 7 | 48 | 28,8 |
| 51 | 26 | 0 | 103 | 7 | 48 | 28,61176471 |
| 52 | 26 | 0 | 104 | 7 | 49 | 29,01568627 |
| 53 | 27 | 0 | 105 | 7 | 49 | 28,82352941 |
| 54 | 27 | 0 | 105 | 7 | 49 | 28,82352941 |
| 55 | 28 | 0 | 107 | 7 | 50 | 29,01960784 |
| 56 | 28 | 0 | 107 | 7 | 50 | 29,01960784 |
| 57 | 29 | 0 | 109 | 7 | 50 | 28,62745098 |
| 58 | 29 | 0 | 109 | 7 | 50 | 28,62745098 |
| 59 | 30 | 0 | 110 | 7 | 51 | 29 |
| 60 | 30 | 0 | 111 | 8 | 51 | 28,8 |
| 61 | 31 | 0 | 112 | 7 | 51 | 28,6 |
| 62 | 31 | 0 | 112 | 8 | 51 | 28,6 |
| 63 | 32 | 0 | 114 | 7 | 52 | 28,75294118 |
| 64 | 32 | 0 | 114 | 8 | 52 | 28,75294118 |
| 65 | 33 | 0 | 115 | 7 | 52 | 28,54901961 |
| 66 | 33 | 0 | 116 | 8 | 53 | 28,89019608 |
| 67 | 34 | 0 | 117 | 7 | 53 | 28,68235294 |
| 68 | 34 | 0 | 117 | 8 | 53 | 28,68235294 |
| 69 | 35 | 0 | 118 | 7 | 53 | 28,4745098 |
| 70 | 35 | 0 | 119 | 8 | 54 | 28,8 |
| 71 | 36 | 0 | 120 | 8 | 54 | 28,58823529 |
| 72 | 36 | 0 | 120 | 8 | 54 | 28,58823529 |
| 73 | 37 | 0 | 121 | 8 | 54 | 28,37647059 |
| 74 | 37 | 0 | 122 | 8 | 55 | 28,68627451 |
| 75 | 37 | 0 | 122 | 9 | 55 | 28,68627451 |
| 76 | 38 | 0 | 123 | 8 | 55 | 28,47058824 |
| 77 | 38 | 0 | 123 | 9 | 55 | 28,47058824 |
| 78 | 39 | 0 | 124 | 8 | 56 | 28,76862745 |
| 79 | 39 | 0 | 125 | 9 | 56 | 28,54901961 |
| 80 | 40 | 0 | 126 | 8 | 56 | 28,32941176 |
| 81 | 40 | 0 | 126 | 9 | 56 | 28,32941176 |
| 82 | 41 | 0 | 127 | 8 | 56 | 28,10980392 |
| 83 | 41 | 0 | 127 | 9 | 57 | 28,61176471 |
| 84 | 42 | 0 | 129 | 8 | 57 | 28,16470588 |
| 85 | 42 | 0 | 129 | 9 | 57 | 28,16470588 |
| 86 | 43 | 0 | 130 | 8 | 57 | 27,94117647 |
| 87 | 43 | 0 | 130 | 9 | 58 | 28,43137255 |
| 88 | 44 | 0 | 131 | 9 | 58 | 28,20392157 |
| 89 | 44 | 0 | 131 | 9 | 58 | 28,20392157 |
| 90 | 45 | 0 | 133 | 9 | 58 | 27,74901961 |
| 91 | 45 | 0 | 133 | 9 | 58 | 27,74901961 |
| 92 | 46 | 0 | 134 | 9 | 59 | 27,99607843 |
| 93 | 46 | 0 | 134 | 9 | 59 | 27,99607843 |
| 94 | 47 | 0 | 135 | 9 | 59 | 27,76470588 |
| 95 | 47 | 0 | 135 | 9 | 59 | 27,76470588 |
| 96 | 48 | 0 | 136 | 9 | 60 | 28 |
| 97 | 48 | 0 | 137 | 9 | 60 | 27,76470588 |
| 98 | 49 | 0 | 138 | 9 | 60 | 27,52941176 |
| 99 | 49 | 0 | 138 | 9 | 60 | 27,52941176 |
| 100 | 50 | 0 | 139 | 9 | 60 | 27,29411765 |

Figure 9 (continued)

| | | | | | |
|---|---|---|---|---|---|
| 101 | 50 | 0 | 139 | 9 | 60 27,29411765 |
| 102 | 51 | 0 | 140 | 9 | 61 27,50980392 |
| 103 | 51 | 0 | 140 | 9 | 61 27,50980392 |
| 104 | 52 | 0 | 141 | 9 | 61 27,27058824 |
| 105 | 52 | 0 | 141 | 9 | 61 27,27058824 |
| 106 | 53 | 0 | 142 | 9 | 62 27,4745098 |
| 107 | 53 | 0 | 142 | 9 | 62 27,4745098 |
| 108 | 54 | 0 | 143 | 9 | 62 27,23137255 |
| 109 | 54 | 0 | 144 | 9 | 62 26,98823529 |
| 110 | 55 | 0 | 145 | 9 | 62 26,74509804 |
| 111 | 55 | 0 | 145 | 10 | 62 26,74509804 |
| 112 | 56 | 0 | 146 | 9 | 63 26,92941176 |
| 113 | 56 | 0 | 146 | 10 | 63 26,92941176 |
| 114 | 57 | 0 | 147 | 9 | 63 26,68235294 |
| 115 | 57 | 0 | 147 | 10 | 63 26,68235294 |
| 116 | 58 | 0 | 148 | 9 | 63 26,43529412 |
| 117 | 58 | 0 | 148 | 10 | 64 26,85490196 |
| 118 | 59 | 0 | 149 | 9 | 64 26,60392157 |
| 119 | 59 | 0 | 149 | 10 | 64 26,60392157 |
| 120 | 60 | 0 | 150 | 9 | 64 26,35294118 |
| 121 | 60 | 0 | 150 | 10 | 64 26,35294118 |
| 122 | 61 | 0 | 151 | 10 | 64 26,10196078 |
| 123 | 61 | 0 | 151 | 10 | 65 26,50980392 |
| 124 | 62 | 0 | 152 | 10 | 65 26,25490196 |
| 125 | 62 | 0 | 152 | 10 | 65 26,25490196 |
| 126 | 63 | 0 | 153 | 10 | 65 26 |
| 127 | 63 | 0 | 153 | 10 | 65 26 |
| 128 | 64 | 0 | 154 | 10 | 66 26,14117647 |
| 129 | 64 | 0 | 154 | 10 | 66 26,14117647 |
| 130 | 65 | 0 | 155 | 10 | 66 25,88235294 |
| 131 | 65 | 0 | 155 | 10 | 66 25,88235294 |
| 132 | 66 | 0 | 156 | 10 | 66 25,62352941 |
| 133 | 66 | 0 | 156 | 10 | 66 25,62352941 |
| 134 | 67 | 0 | 157 | 10 | 67 25,74901961 |
| 135 | 67 | 0 | 157 | 10 | 67 25,74901961 |
| 136 | 68 | 0 | 158 | 10 | 67 25,48627451 |
| 137 | 68 | 0 | 158 | 10 | 67 25,48627451 |
| 138 | 69 | 0 | 159 | 10 | 67 25,22352941 |
| 139 | 69 | 0 | 159 | 10 | 67 25,22352941 |
| 140 | 70 | 0 | 160 | 10 | 68 25,33333333 |
| 141 | 70 | 0 | 160 | 10 | 68 25,33333333 |
| 142 | 71 | 0 | 161 | 10 | 68 25,06666667 |
| 143 | 71 | 0 | 161 | 10 | 68 25,06666667 |
| 144 | 72 | 0 | 162 | 10 | 68 24,8 |
| 145 | 72 | 0 | 162 | 10 | 68 24,8 |
| 146 | 73 | 0 | 163 | 10 | 68 24,53333333 |
| 147 | 73 | 0 | 163 | 10 | 69 24,89411765 |
| 148 | 74 | 0 | 164 | 10 | 69 24,62352941 |
| 149 | 74 | 0 | 164 | 10 | 69 24,62352941 |
| 150 | 75 | 0 | 165 | 10 | 69 24,35294118 |
| 151 | 75 | 0 | 165 | 10 | 69 24,35294118 |

Figure 9 (continued)

| | | | | | | |
|---|---|---|---|---|---|---|
| 152 | 76 | 0 | | 166 | 10 | 69 | 24,08235294 |
| 153 | 76 | 0 | | 166 | 11 | 69 | 24,08235294 |
| 154 | 77 | 0 | | 167 | 10 | 70 | 24,15686275 |
| 155 | 77 | 0 | | 167 | 11 | 70 | 24,15686275 |
| 156 | 78 | 0 | | 167 | 10 | 70 | 24,15686275 |
| 157 | 78 | 0 | | 168 | 11 | 70 | 23,88235294 |
| 158 | 79 | 0 | | 168 | 10 | 70 | 23,88235294 |
| 159 | 79 | 0 | | 168 | 11 | 70 | 23,88235294 |
| 160 | 80 | 0 | | 169 | 10 | 71 | 23,94509804 |
| 161 | 80 | 0 | | 169 | 11 | 71 | 23,94509804 |
| 162 | 81 | 0 | | 170 | 10 | 71 | 23,66666667 |
| 163 | 81 | 0 | | 170 | 11 | 71 | 23,66666667 |
| 164 | 82 | 0 | | 171 | 11 | 71 | 23,38823529 |
| 165 | 82 | 0 | | 171 | 11 | 71 | 23,38823529 |
| 166 | 83 | 0 | | 172 | 11 | 71 | 23,10980392 |
| 167 | 83 | 0 | | 172 | 11 | 72 | 23,43529412 |
| 168 | 84 | 0 | | 173 | 11 | 72 | 23,15294118 |
| 169 | 84 | 0 | | 173 | 11 | 72 | 23,15294118 |
| 170 | 85 | 0 | | 173 | 11 | 72 | 23,15294118 |
| 171 | 85 | 0 | | 174 | 11 | 72 | 22,87058824 |
| 172 | 86 | 0 | | 174 | 11 | 72 | 22,87058824 |
| 173 | 86 | 0 | | 174 | 11 | 72 | 22,87058824 |
| 174 | 87 | 0 | | 175 | 11 | 73 | 22,90196078 |
| 175 | 87 | 0 | | 175 | 11 | 73 | 22,90196078 |
| 176 | 88 | 0 | | 176 | 11 | 73 | 22,61568627 |
| 177 | 88 | 0 | | 176 | 11 | 73 | 22,61568627 |
| 178 | 89 | 0 | | 177 | 11 | 73 | 22,32941176 |
| 179 | 89 | 0 | | 177 | 11 | 73 | 22,32941176 |
| 180 | 90 | 0 | | 178 | 11 | 73 | 22,04313725 |
| 181 | 90 | 0 | | 178 | 11 | 73 | 22,04313725 |
| 182 | 91 | 0 | | 178 | 11 | 74 | 22,34509804 |
| 183 | 91 | 0 | | 179 | 11 | 74 | 22,05490196 |
| 184 | 92 | 0 | | 179 | 11 | 74 | 22,05490196 |
| 185 | 92 | 0 | | 179 | 11 | 74 | 22,05490196 |
| 186 | 93 | 0 | | 180 | 11 | 74 | 21,76470588 |
| 187 | 93 | 0 | | 180 | 11 | 74 | 21,76470588 |
| 188 | 94 | 0 | | 181 | 11 | 74 | 21,4745098 |
| 189 | 94 | 0 | | 181 | 11 | 75 | 21,76470588 |
| 190 | 95 | 0 | | 182 | 11 | 75 | 21,47058824 |
| 191 | 95 | 0 | | 182 | 11 | 75 | 21,47058824 |
| 192 | 96 | 0 | | 182 | 11 | 75 | 21,47058824 |
| 193 | 96 | 0 | | 182 | 11 | 75 | 21,47058824 |
| 194 | 97 | 0 | | 183 | 11 | 75 | 21,17647059 |
| 195 | 97 | 0 | | 183 | 11 | 75 | 21,17647059 |
| 196 | 98 | 0 | | 184 | 11 | 76 | 21,16078431 |
| 197 | 98 | 0 | | 184 | 11 | 76 | 21,16078431 |
| 198 | 99 | 0 | | 185 | 11 | 76 | 20,8627451 |
| 199 | 99 | 0 | | 185 | 11 | 76 | 20,8627451 |
| 200 | 100 | 0 | | 185 | 11 | 76 | 20,8627451 |
| 201 | 100 | 0 | | 186 | 11 | 76 | 20,56470588 |
| 202 | 101 | 0 | | 186 | 11 | 76 | 20,56470588 |

Figure 9 (continued)

| | | | | | | |
|---|---|---|---|---|---|---|
| 203 | 101 | 0 | 186 | 12 | 76 | 20,56470588 |
| 204 | 102 | 0 | 187 | 11 | 77 | 20,53333333 |
| 205 | 102 | 0 | 187 | 12 | 77 | 20,53333333 |
| 206 | 103 | 0 | 188 | 11 | 77 | 20,23137255 |
| 207 | 103 | 0 | 188 | 12 | 77 | 20,23137255 |
| 208 | 104 | 0 | 188 | 11 | 77 | 20,23137255 |
| 209 | 104 | 0 | 189 | 12 | 77 | 19,92941176 |
| 210 | 105 | 0 | 189 | 11 | 77 | 19,92941176 |
| 211 | 105 | 0 | 189 | 12 | 77 | 19,92941176 |
| 212 | 106 | 0 | 190 | 11 | 78 | 19,88235294 |
| 213 | 106 | 0 | 190 | 12 | 78 | 19,88235294 |
| 214 | 107 | 0 | 191 | 12 | 78 | 19,57647059 |
| 215 | 107 | 0 | 191 | 12 | 78 | 19,57647059 |
| 216 | 108 | 0 | 191 | 12 | 78 | 19,57647059 |
| 217 | 108 | 0 | 191 | 12 | 78 | 19,57647059 |
| 218 | 109 | 0 | 192 | 12 | 78 | 19,27058824 |
| 219 | 109 | 0 | 192 | 12 | 78 | 19,27058824 |
| 220 | 110 | 0 | 193 | 12 | 79 | 19,20784314 |
| 221 | 110 | 0 | 193 | 12 | 79 | 19,20784314 |
| 222 | 111 | 0 | 193 | 12 | 79 | 19,20784314 |
| 223 | 111 | 0 | 194 | 12 | 79 | 18,89803922 |
| 224 | 112 | 0 | 194 | 12 | 79 | 18,89803922 |
| 225 | 112 | 0 | 194 | 12 | 79 | 18,89803922 |
| 226 | 113 | 0 | 195 | 12 | 79 | 18,58823529 |
| 227 | 113 | 0 | 195 | 12 | 79 | 18,58823529 |
| 228 | 114 | 0 | 196 | 12 | 79 | 18,27843137 |
| 229 | 114 | 0 | 196 | 12 | 80 | 18,50980392 |
| 230 | 115 | 0 | 196 | 12 | 80 | 18,50980392 |
| 231 | 115 | 0 | 196 | 12 | 80 | 18,50980392 |
| 232 | 116 | 0 | 197 | 12 | 80 | 18,19607843 |
| 233 | 116 | 0 | 197 | 12 | 80 | 18,19607843 |
| 234 | 117 | 0 | 198 | 12 | 80 | 17,88235294 |
| 235 | 117 | 0 | 198 | 12 | 80 | 17,88235294 |
| 236 | 118 | 0 | 198 | 12 | 80 | 17,88235294 |
| 237 | 118 | 0 | 198 | 12 | 80 | 17,88235294 |
| 238 | 119 | 0 | 199 | 12 | 81 | 17,78823529 |
| 239 | 119 | 0 | 199 | 12 | 81 | 17,78823529 |
| 240 | 120 | 0 | 200 | 12 | 81 | 17,47058824 |
| 241 | 120 | 0 | 200 | 12 | 81 | 17,47058824 |
| 242 | 121 | 0 | 200 | 12 | 81 | 17,47058824 |
| 243 | 121 | 0 | 200 | 12 | 81 | 17,47058824 |
| 244 | 122 | 0 | 201 | 12 | 81 | 17,15294118 |
| 245 | 122 | 0 | 201 | 12 | 81 | 17,15294118 |
| 246 | 123 | 0 | 202 | 12 | 81 | 16,83529412 |
| 247 | 123 | 0 | 202 | 12 | 82 | 17,04313725 |
| 248 | 124 | 0 | 202 | 12 | 82 | 17,04313725 |
| 249 | 124 | 0 | 202 | 12 | 82 | 17,04313725 |
| 250 | 125 | 0 | 203 | 12 | 82 | 16,72156863 |
| 251 | 125 | 0 | 203 | 12 | 82 | 16,72156863 |
| 252 | 126 | 0 | 204 | 12 | 82 | 16,4 |
| 253 | 126 | 0 | 204 | 12 | 82 | 16,4 |

Figure 9 (continued)

| | | | | | | |
|---|---|---|---|---|---|---|
| 254 | 127 | 0 | | 204 | 12 | 82 | 16,4 |
| 255 | 127 | 0 | | 204 | 12 | 82 | 16,4 |
| 255 | 128 | 0 | | 205 | 12 | 83 | 16,2745098 |
| 255 | 128 | 1 | | 205 | 12 | 81 | 15,88235294 |
| 255 | 129 | 2 | | 205 | 12 | 80 | 15,68627451 |
| 255 | 129 | 3 | | 205 | 12 | 79 | 15,49019608 |
| 255 | 130 | 4 | | 206 | 12 | 78 | 14,98823529 |
| 255 | 130 | 5 | | 206 | 12 | 77 | 14,79607843 |
| 255 | 131 | 6 | | 206 | 12 | 76 | 14,60392157 |
| 255 | 131 | 7 | | 206 | 12 | 75 | 14,41176471 |
| 255 | 132 | 8 | | 207 | 11 | 74 | 13,92941176 |
| 255 | 132 | 9 | | 207 | 12 | 73 | 13,74117647 |
| 255 | 133 | 10 | | 207 | 11 | 72 | 13,55294118 |
| 255 | 133 | 11 | | 207 | 11 | 71 | 13,36470588 |
| 255 | 134 | 12 | | 208 | 11 | 70 | 12,90196078 |
| 255 | 134 | 13 | | 208 | 11 | 69 | 12,71764706 |
| 255 | 135 | 14 | | 208 | 11 | 69 | 12,71764706 |
| 255 | 135 | 15 | | 208 | 11 | 68 | 12,53333333 |
| 255 | 136 | 16 | | 208 | 11 | 67 | 12,34901961 |
| 255 | 136 | 17 | | 209 | 11 | 66 | 11,90588235 |
| 255 | 137 | 18 | | 209 | 11 | 65 | 11,7254902 |
| 255 | 137 | 19 | | 209 | 11 | 65 | 11,7254902 |
| 255 | 138 | 20 | | 209 | 11 | 64 | 11,54509804 |
| 255 | 138 | 21 | | 209 | 11 | 63 | 11,36470588 |
| 255 | 139 | 22 | | 210 | 11 | 63 | 11,11764706 |
| 255 | 139 | 23 | | 210 | 11 | 62 | 10,94117647 |
| 255 | 140 | 24 | | 210 | 10 | 61 | 10,76470588 |
| 255 | 140 | 25 | | 210 | 11 | 60 | 10,58823529 |
| 255 | 141 | 26 | | 211 | 10 | 60 | 10,35294118 |
| 255 | 141 | 27 | | 211 | 10 | 59 | 10,18039216 |
| 255 | 142 | 28 | | 211 | 10 | 59 | 10,18039216 |
| 255 | 142 | 29 | | 211 | 10 | 58 | 10,00784314 |
| 255 | 143 | 30 | | 212 | 10 | 57 | 9,611764706 |
| 255 | 143 | 31 | | 212 | 10 | 57 | 9,611764706 |
| 255 | 144 | 32 | | 212 | 10 | 56 | 9,443137255 |
| 255 | 144 | 33 | | 212 | 10 | 56 | 9,443137255 |
| 255 | 145 | 34 | | 213 | 10 | 55 | 9,058823529 |
| 255 | 145 | 35 | | 213 | 10 | 54 | 8,894117647 |
| 255 | 146 | 36 | | 213 | 10 | 54 | 8,894117647 |
| 255 | 146 | 37 | | 213 | 10 | 53 | 8,729411765 |
| 255 | 147 | 38 | | 214 | 10 | 53 | 8,521568627 |
| 255 | 147 | 39 | | 214 | 10 | 52 | 8,360784314 |
| 255 | 148 | 40 | | 214 | 9 | 52 | 8,360784314 |
| 255 | 148 | 41 | | 214 | 10 | 51 | 8,2 |
| 255 | 149 | 42 | | 214 | 9 | 51 | 8,2 |
| 255 | 149 | 43 | | 214 | 9 | 50 | 8,039215686 |
| 255 | 150 | 44 | | 215 | 9 | 50 | 7,843137255 |
| 255 | 150 | 45 | | 215 | 9 | 49 | 7,68627451 |
| 255 | 151 | 46 | | 215 | 9 | 49 | 7,68627451 |
| 255 | 151 | 47 | | 215 | 9 | 48 | 7,529411765 |
| 255 | 152 | 48 | | 216 | 9 | 48 | 7,341176471 |

Figure 9 (continued)

| | | | | | | |
|---|---|---|---|---|---|---|
| 255 | 152 | 49 | | 216 | 9 | 47 | 7,188235294 |
| 255 | 153 | 50 | | 216 | 9 | 47 | 7,188235294 |
| 255 | 153 | 51 | | 216 | 9 | 46 | 7,035294118 |
| 255 | 154 | 52 | | 217 | 9 | 46 | 6,854901961 |
| 255 | 154 | 53 | | 217 | 9 | 46 | 6,854901961 |
| 255 | 155 | 54 | | 217 | 9 | 45 | 6,705882353 |
| 255 | 155 | 55 | | 217 | 9 | 45 | 6,705882353 |
| 255 | 156 | 56 | | 218 | 9 | 44 | 6,384313725 |
| 255 | 156 | 57 | | 218 | 9 | 44 | 6,384313725 |
| 255 | 157 | 58 | | 218 | 8 | 44 | 6,384313725 |
| 255 | 157 | 59 | | 218 | 9 | 43 | 6,239215686 |
| 255 | 158 | 60 | | 218 | 8 | 43 | 6,239215686 |
| 255 | 158 | 61 | | 218 | 8 | 42 | 6,094117647 |
| 255 | 159 | 62 | | 219 | 8 | 42 | 5,929411765 |
| 255 | 159 | 63 | | 219 | 8 | 41 | 5,788235294 |
| 255 | 160 | 64 | | 219 | 8 | 41 | 5,788235294 |
| 255 | 160 | 65 | | 219 | 8 | 41 | 5,788235294 |
| 255 | 161 | 66 | | 220 | 8 | 40 | 5,490196078 |
| 255 | 161 | 67 | | 220 | 8 | 40 | 5,490196078 |
| 255 | 162 | 68 | | 220 | 8 | 40 | 5,490196078 |
| 255 | 162 | 69 | | 220 | 8 | 39 | 5,352941176 |
| 255 | 163 | 70 | | 221 | 8 | 39 | 5,2 |
| 255 | 163 | 71 | | 221 | 8 | 38 | 5,066666667 |
| 255 | 164 | 72 | | 221 | 8 | 38 | 5,066666667 |
| 255 | 164 | 73 | | 221 | 8 | 38 | 5,066666667 |
| 255 | 165 | 74 | | 221 | 8 | 37 | 4,933333333 |
| 255 | 165 | 75 | | 221 | 8 | 37 | 4,933333333 |
| 255 | 166 | 76 | | 222 | 7 | 37 | 4,788235294 |
| 255 | 166 | 77 | | 222 | 8 | 36 | 4,658823529 |
| 255 | 167 | 78 | | 222 | 7 | 36 | 4,658823529 |
| 255 | 167 | 79 | | 222 | 7 | 36 | 4,658823529 |
| 255 | 168 | 80 | | 223 | 7 | 35 | 4,392156863 |
| 255 | 168 | 81 | | 223 | 7 | 35 | 4,392156863 |
| 255 | 169 | 82 | | 223 | 7 | 35 | 4,392156863 |
| 255 | 169 | 83 | | 223 | 7 | 34 | 4,266666667 |
| 255 | 170 | 84 | | 223 | 7 | 34 | 4,266666667 |
| 255 | 170 | 85 | | 224 | 7 | 34 | 4,133333333 |
| 255 | 171 | 86 | | 224 | 7 | 33 | 4,011764706 |
| 255 | 171 | 87 | | 224 | 7 | 33 | 4,011764706 |
| 255 | 172 | 88 | | 224 | 7 | 33 | 4,011764706 |
| 255 | 172 | 89 | | 224 | 7 | 32 | 3,890196078 |
| 255 | 173 | 90 | | 225 | 7 | 32 | 3,764705882 |
| 255 | 173 | 91 | | 225 | 7 | 32 | 3,764705882 |
| 255 | 174 | 92 | | 225 | 7 | 32 | 3,764705882 |
| 255 | 174 | 93 | | 225 | 7 | 31 | 3,647058824 |
| 255 | 175 | 94 | | 226 | 6 | 31 | 3,525490196 |
| 255 | 175 | 95 | | 226 | 7 | 31 | 3,525490196 |
| 255 | 175 | 96 | | 226 | 7 | 30 | 3,411764706 |
| 255 | 176 | 97 | | 226 | 6 | 30 | 3,411764706 |
| 255 | 176 | 98 | | 226 | 7 | 30 | 3,411764706 |
| 255 | 177 | 99 | | 226 | 6 | 29 | 3,298039216 |

Figure 9 (continued)

| | | | | | | |
|---|---|---|---|---|---|---|
| 255 | 177 | 100 | | 226 | 6 | 29 | 3,298039216 |
| 255 | 178 | 101 | | 227 | 6 | 29 | 3,184313725 |
| 255 | 178 | 102 | | 227 | 6 | 28 | 3,074509804 |
| 255 | 179 | 103 | | 227 | 6 | 28 | 3,074509804 |
| 255 | 179 | 104 | | 227 | 6 | 28 | 3,074509804 |
| 255 | 180 | 105 | | 228 | 6 | 28 | 2,964705882 |
| 255 | 180 | 106 | | 228 | 6 | 27 | 2,858823529 |
| 255 | 181 | 107 | | 228 | 6 | 27 | 2,858823529 |
| 255 | 181 | 108 | | 228 | 6 | 27 | 2,858823529 |
| 255 | 182 | 109 | | 228 | 6 | 27 | 2,858823529 |
| 255 | 182 | 110 | | 228 | 6 | 26 | 2,752941176 |
| 255 | 183 | 111 | | 229 | 6 | 26 | 2,650980392 |
| 255 | 183 | 112 | | 229 | 6 | 26 | 2,650980392 |
| 255 | 184 | 113 | | 229 | 6 | 26 | 2,650980392 |
| 255 | 184 | 114 | | 229 | 6 | 25 | 2,549019608 |
| 255 | 185 | 115 | | 230 | 6 | 25 | 2,450980392 |
| 255 | 185 | 116 | | 230 | 6 | 25 | 2,450980392 |
| 255 | 186 | 117 | | 230 | 6 | 25 | 2,450980392 |
| 255 | 186 | 118 | | 230 | 6 | 24 | 2,352941176 |
| 255 | 187 | 119 | | 230 | 5 | 24 | 2,352941176 |
| 255 | 187 | 120 | | 230 | 6 | 24 | 2,352941176 |
| 255 | 188 | 121 | | 231 | 5 | 24 | 2,258823529 |
| 255 | 188 | 122 | | 231 | 5 | 23 | 2,164705882 |
| 255 | 189 | 123 | | 231 | 5 | 23 | 2,164705882 |
| 255 | 189 | 124 | | 231 | 5 | 23 | 2,164705882 |
| 255 | 190 | 125 | | 232 | 5 | 23 | 2,074509804 |
| 255 | 190 | 126 | | 232 | 5 | 22 | 1,984313725 |
| 255 | 191 | 127 | | 232 | 5 | 22 | 1,984313725 |
| 255 | 191 | 128 | | 232 | 5 | 22 | 1,984313725 |
| 255 | 192 | 129 | | 232 | 5 | 22 | 1,984313725 |
| 255 | 192 | 130 | | 232 | 5 | 21 | 1,894117647 |
| 255 | 193 | 131 | | 233 | 5 | 21 | 1,811764706 |
| 255 | 193 | 132 | | 233 | 5 | 21 | 1,811764706 |
| 255 | 194 | 133 | | 233 | 5 | 21 | 1,811764706 |
| 255 | 194 | 134 | | 233 | 5 | 20 | 1,725490196 |
| 255 | 195 | 135 | | 234 | 5 | 20 | 1,647058824 |
| 255 | 195 | 136 | | 234 | 5 | 20 | 1,647058824 |
| 255 | 196 | 137 | | 234 | 5 | 20 | 1,647058824 |
| 255 | 196 | 138 | | 234 | 5 | 20 | 1,647058824 |
| 255 | 197 | 139 | | 234 | 5 | 19 | 1,564705882 |
| 255 | 197 | 140 | | 234 | 5 | 19 | 1,564705882 |
| 255 | 198 | 141 | | 235 | 4 | 19 | 1,490196078 |
| 255 | 198 | 142 | | 235 | 5 | 19 | 1,490196078 |
| 255 | 199 | 143 | | 235 | 4 | 19 | 1,490196078 |
| 255 | 199 | 144 | | 235 | 4 | 18 | 1,411764706 |
| 255 | 200 | 145 | | 235 | 4 | 18 | 1,411764706 |
| 255 | 200 | 146 | | 235 | 4 | 18 | 1,411764706 |
| 255 | 201 | 147 | | 236 | 4 | 18 | 1,341176471 |
| 255 | 201 | 148 | | 236 | 4 | 17 | 1,266666667 |
| 255 | 202 | 149 | | 236 | 4 | 17 | 1,266666667 |
| 255 | 202 | 150 | | 236 | 4 | 17 | 1,266666667 |

Figure 9 (continued)

| | | | | | | |
|---|---|---|---|---|---|---|
| 255 | 203 | 151 | | 237 | 4 | 17 | 1,2 |
| 255 | 203 | 152 | | 237 | 4 | 17 | 1,2 |
| 255 | 204 | 153 | | 237 | 4 | 16 | 1,129411765 |
| 255 | 204 | 154 | | 237 | 4 | 16 | 1,129411765 |
| 255 | 205 | 155 | | 237 | 4 | 16 | 1,129411765 |
| 255 | 205 | 156 | | 237 | 4 | 16 | 1,129411765 |
| 255 | 206 | 157 | | 238 | 4 | 16 | 1,066666667 |
| 255 | 206 | 158 | | 238 | 4 | 15 | 1 |
| 255 | 207 | 159 | | 238 | 4 | 15 | 1 |
| 255 | 207 | 160 | | 238 | 4 | 15 | 1 |
| 255 | 208 | 161 | | 238 | 4 | 15 | 1 |
| 255 | 208 | 162 | | 238 | 4 | 15 | 1 |
| 255 | 209 | 163 | | 239 | 3 | 14 | 0,878431373 |
| 255 | 209 | 164 | | 239 | 4 | 14 | 0,878431373 |
| 255 | 210 | 165 | | 239 | 3 | 14 | 0,878431373 |
| 255 | 210 | 166 | | 239 | 3 | 14 | 0,878431373 |
| 255 | 211 | 167 | | 240 | 3 | 14 | 0,823529412 |
| 255 | 211 | 168 | | 240 | 3 | 13 | 0,764705882 |
| 255 | 212 | 169 | | 240 | 3 | 13 | 0,764705882 |
| 255 | 212 | 170 | | 240 | 3 | 13 | 0,764705882 |
| 255 | 213 | 171 | | 240 | 3 | 13 | 0,764705882 |
| 255 | 213 | 172 | | 240 | 3 | 13 | 0,764705882 |
| 255 | 214 | 173 | | 241 | 3 | 13 | 0,71372549 |
| 255 | 214 | 174 | | 241 | 3 | 12 | 0,658823529 |
| 255 | 215 | 175 | | 241 | 3 | 12 | 0,658823529 |
| 255 | 215 | 176 | | 241 | 3 | 12 | 0,658823529 |
| 255 | 216 | 177 | | 241 | 3 | 12 | 0,658823529 |
| 255 | 216 | 178 | | 241 | 3 | 12 | 0,658823529 |
| 255 | 217 | 179 | | 242 | 3 | 12 | 0,611764706 |
| 255 | 217 | 180 | | 242 | 3 | 11 | 0,560784314 |
| 255 | 218 | 181 | | 242 | 3 | 11 | 0,560784314 |
| 255 | 218 | 182 | | 242 | 3 | 11 | 0,560784314 |
| 255 | 219 | 183 | | 243 | 3 | 11 | 0,517647059 |
| 255 | 219 | 184 | | 243 | 3 | 11 | 0,517647059 |
| 255 | 220 | 185 | | 243 | 3 | 10 | 0,470588235 |
| 255 | 220 | 186 | | 243 | 3 | 10 | 0,470588235 |
| 255 | 221 | 187 | | 243 | 2 | 10 | 0,470588235 |
| 255 | 221 | 188 | | 243 | 3 | 10 | 0,470588235 |
| 255 | 222 | 189 | | 244 | 2 | 10 | 0,431372549 |
| 255 | 222 | 190 | | 244 | 2 | 10 | 0,431372549 |
| 255 | 223 | 191 | | 244 | 2 | 9 | 0,388235294 |
| 255 | 223 | 192 | | 244 | 2 | 9 | 0,388235294 |
| 255 | 224 | 193 | | 244 | 2 | 9 | 0,388235294 |
| 255 | 224 | 194 | | 244 | 2 | 9 | 0,388235294 |
| 255 | 225 | 195 | | 245 | 2 | 9 | 0,352941176 |
| 255 | 225 | 196 | | 245 | 2 | 9 | 0,352941176 |
| 255 | 226 | 197 | | 245 | 2 | 8 | 0,31372549 |
| 255 | 226 | 198 | | 245 | 2 | 8 | 0,31372549 |
| 255 | 227 | 199 | | 245 | 2 | 8 | 0,31372549 |
| 255 | 227 | 200 | | 245 | 2 | 8 | 0,31372549 |
| 255 | 228 | 201 | | 246 | 2 | 8 | 0,282352941 |

Figure 9 (continued)

| | | | | | | |
|---|---|---|---|---|---|---|
| 255 | 228 | 202 | 246 | 2 | 8 | 0,282352941 |
| 255 | 229 | 203 | 246 | 2 | 7 | 0,247058824 |
| 255 | 229 | 204 | 246 | 2 | 7 | 0,247058824 |
| 255 | 230 | 205 | 246 | 2 | 7 | 0,247058824 |
| 255 | 230 | 206 | 246 | 2 | 7 | 0,247058824 |
| 255 | 231 | 207 | 247 | 2 | 7 | 0,219607843 |
| 255 | 231 | 208 | 247 | 2 | 7 | 0,219607843 |
| 255 | 232 | 209 | 247 | 2 | 7 | 0,219607843 |
| 255 | 232 | 210 | 247 | 2 | 6 | 0,188235294 |
| 255 | 233 | 211 | 247 | 2 | 6 | 0,188235294 |
| 255 | 233 | 212 | 248 | 2 | 6 | 0,164705882 |
| 255 | 234 | 213 | 248 | 1 | 6 | 0,164705882 |
| 255 | 234 | 214 | 248 | 2 | 6 | 0,164705882 |
| 255 | 235 | 215 | 248 | 1 | 6 | 0,164705882 |
| 255 | 235 | 216 | 248 | 2 | 5 | 0,137254902 |
| 255 | 236 | 217 | 249 | 1 | 5 | 0,117647059 |
| 255 | 236 | 218 | 249 | 1 | 5 | 0,117647059 |
| 255 | 237 | 219 | 249 | 1 | 5 | 0,117647059 |
| 255 | 237 | 220 | 249 | 1 | 5 | 0,117647059 |
| 255 | 238 | 221 | 249 | 1 | 5 | 0,117647059 |
| 255 | 238 | 222 | 249 | 1 | 4 | 0,094117647 |
| 255 | 239 | 223 | 250 | 1 | 4 | 0,078431373 |
| 255 | 239 | 224 | 250 | 1 | 4 | 0,078431373 |
| 255 | 240 | 225 | 250 | 1 | 4 | 0,078431373 |
| 255 | 240 | 226 | 250 | 1 | 4 | 0,078431373 |
| 255 | 241 | 227 | 250 | 1 | 4 | 0,078431373 |
| 255 | 241 | 228 | 250 | 1 | 4 | 0,078431373 |
| 255 | 242 | 229 | 251 | 1 | 4 | 0,062745098 |
| 255 | 242 | 230 | 251 | 1 | 3 | 0,047058824 |
| 255 | 243 | 231 | 251 | 1 | 3 | 0,047058824 |
| 255 | 243 | 232 | 251 | 1 | 3 | 0,047058824 |
| 255 | 244 | 233 | 251 | 1 | 3 | 0,047058824 |
| 255 | 244 | 234 | 251 | 1 | 3 | 0,047058824 |
| 255 | 245 | 235 | 252 | 1 | 3 | 0,035294118 |
| 255 | 245 | 236 | 252 | 1 | 2 | 0,023529412 |
| 255 | 246 | 237 | 252 | 1 | 2 | 0,023529412 |
| 255 | 246 | 238 | 252 | 1 | 2 | 0,023529412 |
| 255 | 247 | 239 | 252 | 1 | 2 | 0,023529412 |
| 255 | 247 | 240 | 252 | 1 | 2 | 0,023529412 |
| 255 | 248 | 241 | 253 | 0 | 2 | 0,015686275 |
| 255 | 248 | 242 | 253 | 1 | 2 | 0,015686275 |
| 255 | 249 | 243 | 253 | 0 | 2 | 0,015686275 |
| 255 | 249 | 244 | 253 | 0 | 1 | 0,007843137 |
| 255 | 250 | 245 | 253 | 0 | 1 | 0,007843137 |
| 255 | 250 | 246 | 253 | 0 | 1 | 0,007843137 |
| 255 | 251 | 247 | 254 | 0 | 1 | 0,003921569 |
| 255 | 251 | 248 | 254 | 0 | 1 | 0,003921569 |
| 255 | 252 | 249 | 254 | 0 | 1 | 0,003921569 |
| 255 | 252 | 250 | 254 | 0 | 1 | 0,003921569 |
| 255 | 253 | 251 | 254 | 0 | 1 | 0,003921569 |
| 255 | 253 | 252 | 254 | 0 | 0 | 0 |

METHODS FOR ASSESSING ERYTHEMA

CROSS-REFERENCE TO RELATED APPLICATIONS

This application is a national phase application under 35 U.S.C. § 371 of International Application No. PCT/EP2014/055549 filed 19 Mar. 2014, which claims priority to European Application No. 13160048.8 filed 19 Mar. 2013. The entire contents of each of the above-referenced disclosures is specifically incorporated herein by reference without disclaimer.

FIELD OF THE INVENTION

The present invention relates to methods for an objective and quantitative erythema documentation and analysis. In particular, the invention relates to a method for assessing erythema of a subject comprising the steps of measuring the light reflectance of a skin or mucosal area of the subject, obtaining the $L^*$ value and the $a^*$ value of said measurement according to the $L^*a^*b^*$ color space, and calculating the erythema value according to the formula $(L^*_{max}-L^*) \times a^*$. Furthermore, the invention relates to a method for assessing the risk of a subject to develop erythema caused by irradiation by calculating the erythema value according to the invention; an according method for predicting the intensity of erythema that a subject develops due to irradiation; an according method for predicting the time until a subject develops erythema caused by irradiation; an according method for testing a pharmaceutical or cosmetic preparation for its ability to cause or treat erythema in a subject; and to an according method for testing a pharmaceutical or cosmetic preparation for its ability to ameliorate the appearance of erythema of a subject. The invention further relates to methods for analyzing skin color of a subject, methods for documenting or analyzing wounds or wound healing of a subject based on the formula $(L^*_{max}-L^*) \times a^*$. In another aspect, the invention relates to methods of analyzing meat based on the formula $(L^*_{max}-L^*) \times a^*$.

BACKGROUND TO THE INVENTION

Skin or mucosal inflammation is often manifested as erythema. Erythema is frequently associated with diaper rash, acne, dermatitis, eczema and other skin or mucosal conditions. Another example of erythema is radiation dermatitis, which is an inflammatory skin reaction associated with prolonged exposure to ionizing radiation.

Radiation dermatitis occurs to some degree in most patients receiving radiation therapy, with or without chemotherapy. In severe cases it leads to discontinuation of radiation therapy. Acute radiation induced dermatitis is one of the most frequent side effects of radiotherapy. The pathoethiological cause for the reaction is linked to massive ROS production which is induced during irradiation treatment (Beckmann and Flohé 1981) and in the course of chemotherapy (Kasapović et al. 2010). This ionizing radiation can lead to acute dermatitis in 95% of patients, whereof in 87% of patients moderate to severe radiodermatitis occurs during or at the end of the treatment (Mc Question M 2006). The severity of the skin reaction ranges from a moderate erythema to edema or deep ulcerations. The occurrence of this reaction depends on aspects associated with the therapy (radiation quality, dose per fraction, cumulative dose, fraction scheme, size of the treatment area, concomitant therapy, pre-radiation, localization of irradiated area) and on aspects associated with the patient (skin type, sensitivity to radiation, concomitant diseases). Pruritus, erythema, skin distension, epitheliolysis, and pain affect not only the quality of life but also pose a risk of an infection of the open wounds. Consequently, this may lead to treatment interruptions or discontinuations of the RTX, and longer deferment of the subsequently planned system therapy. Thus an early detection, precise documentation and treatment of these dermal toxicities are of great importance.

Furthermore, up to now there is no reliable prognostic parameter available to predict the risk to develop radiodermatitis upon radiation therapy. According to historical data, breast size, smoking history, body mass index (BMI) and comorbidities such as diabetes, rheumatoid arthritis and hypertension are under suspicion to be correlated with an increased risk for the development of radiodermatitis in the course of cancer irradiation therapy (Fernando I N et al., Clin Oncol 1996; 8:226-233). However the published data is conflicting. According to a recent single blind randomized phase III trial in breast cancer patients, no association between dermatitis and BMI or breast size were observed (Pinnix C et al., Int J Radiat Oncol Biol Phys 2012 Jul. 15; 83(4):1089-94), also confirmed by our own data. Furthermore, the radiation field size ($cm^2$) and the basic skin color according to the Fitzpatrick Scale (1-2 versus 3-4) did not correlate with the risk to develop grade 2 dermatitis (based on the CTCAE, further described below) according to our own data. However, a prognostic marker would allow to prevent or reduce radiation dermatitis by determining or adapting radiation dose and duration, and also to predict the time until a prophylaxis and/or treatment needs to be given.

So far, erythema is clinically assessed mainly by subjective observation by a physician. For example, the classification system Common Terminology Criteria for Adverse Effects (CTCAE v. 4.03), developed by the Radiation Therapy Oncology Group (RTOG), and the National Cancer Institute (NCI), divides skin reactions and other adverse events into 5 grades, according to the degree of severity. This grading system has already been used in numerous clinical trials. However, the shortcomings of said current clinical classification systems are mainly based on the subjective assessment of the skin condition, which can vary greatly among assessors and may even differ in one assessor in the course of one day or between several days. A further drawback of this method is the classification in only five grades. Thus, minor differences in the skin condition, as needed for clinical comparison of the effectiveness of e.g. topical medication, cannot be sufficiently indicated.

For a more objective assessment of erythema several devices have been used. For example, chromameters have been utilized for analyzing hemoglobin, since skin or mucosal erythema is primarily due to vasodilation and local increases in hemoglobin concentration. Chromameters give values of standardized parameters for color evaluation: $L^*$, $a^*$, $b^*$, with $a^*$ being used as an indicator of the "red" content and therefore related to erythema.

Spectrophotometers have also been used for analyzing hemoglobin based on diffuse reflectance spectroscopy, according to which the reflected light from skin is collected and analyzed into its spectral components. Spectral analysis algorithms have been used to calculate chromophore concentrations including oxy- and deoxy-hemoglobin (relating to erythema). Various light reflectance devices such as a Mexameter are also known for giving an erythema index.

The analysis of digital color images of skin has also been utilized for analyzing erythema Such methods are described for example in U.S. Pat. No. 8,150,501 and in Jung et al 2005, Lasers in Surgery and Medicine 37:186-191 or U.S. Pat. No. 8,150,501 and Jung et al 2004, Lasers in Surgery and Medicine 34:174-181.

Another imaging analysis tool for the assessment of erythema is the DermaVision system from the company OptoBioMed (http://www.optobiomed.co.kr/; see also the patent application KR2003083623).

The wound healing analysis tool (W.H.A.T) is a computer-based method to assess wound healing (see e.g. T. Wild, M. Prinz, N. Fortner, W. Krois, K. Sahora, S. Stremitzer and T. Hoelzenbein (2008). "Digital measurement and analysis of wounds based on colour segmentation". European Surgery 40(1):5-10; and S. Stremitzer and T. Wild (2007). "Digitate Wundanalyse mit W.H.A.T. (Wound Healing Analyzing Tool): Manual der Wundheilung. 15-22; and http://what-tool.com). The W.H.A.T system is based on certain threshold levels for parameters, such as color, which allow categorization and sizing of wound segments (e.g. wound center, wound border) and thus, allows to document wound healing based on the assessment of the decrease of the size of the central wound area, which is defined by certain threshold parameters.

Nischek et al. (IEEE Transactions on Medical Imaging, vol 16, no 6, 1997) analyse skin erythema using true-color images. Hirotsugu (The Journal of Medical Investigation, vol 44, 1998, pages 121-126) discloses methods for use in measurement of skin color. Document US 2005/030372 A1 (Jung et al.) discloses a method for assessing erythema of a subject.

All of the methods described above are able to identify erythema or skin redness and to define areas of erythema. However, these techniques show substantial deficiencies in the assessment of erythema intensity. In particular, the prior art methods do not allow a reliable quantitative measurement of various grades of inflammation or the differentiation between several intensities of erythema, especially not for rather low or high intensities of erythema. Thus, the methods of the prior art do neither provide a solid measure for erythema and therewith associated cutaneous alterations over the entire range of intensities nor do they offer a innovative computational techniques linking erythema assessment and erythema documentation with the possibility for remote monitoring of individual subjects or subject areas over varying observation periods.

Accordingly, novel objective methods and innovative computational assessment and monitoring tools are urgently needed for reduction of these inter- and intra-observer variability as well as for sensitive and quantitative assessment of the degree of erythema over the entire intensity range and varying observation times.

BRIEF DESCRIPTION OF THE INVENTION

In a first aspect, the invention relates to a method for assessing erythema of a subject comprising the steps of
measuring the light reflectance of a skin or mucosal area of the subject,
obtaining the L* value and the a* value of said measurement according to the L*a*b* color space, and
calculating the erythema value according to the formula $$(L^*_{max}-L^*) \times a^*.$$

In a second aspect, the invention relates to a method for assessing the risk of a subject to develop erythema caused by irradiation comprising the steps of
measuring the light reflectance of a skin or mucosal area of a subject prior to irradiation,
obtaining the L* value and the a* value of said measurement according to the L*a*b* color space,
calculating the baseline erythema value according to the formula $$(L^*_{max}-L^*) \times a^*, \text{ and}$$

correlating the baseline erythema value to the risk of the subject to develop erythema caused by irradiation.

In a third aspect, the invention relates to a method for predicting the intensity of erythema that a subject develops due to irradiation comprising the steps as described above, and correlating the baseline erythema value to the intensity of erythema that the subject develops due to irradiation.

In a fourth aspect, the invention relates to a method for predicting the time until a subject develops erythema caused by irradiation comprising the steps as described above, and inversely correlating the baseline erythema value to the time until the subject develops erythema caused by irradiation.

In a fifth aspect, the invention relates to a method for testing a pharmaceutical or cosmetic preparation for its ability to cause or treat erythema in a subject comprising the steps of
measuring the light reflectance of a skin or mucosal area of the subject prior to and following the administration of the pharmaceutical or cosmetic preparation,
obtaining the L* value and the a* value of each measurement according to the L*a*b* color space, and
calculating the erythema value for each measurement according to the formula $$(L^*_{max}-L^*) \times a^*.$$

In a sixth aspect, the invention relates to a method for testing a pharmaceutical or cosmetic preparation for its ability to ameliorate the appearance of erythema of a subject comprising the steps as described above.

In a seventh aspect, the invention relates to a method for analyzing skin color of a subject comprising the steps of
measuring the light reflectance of a skin or mucosal area of the subject,
obtaining the L* value and the a* value of said measurement according to the L*a*b* color space, and
calculating the skin redness value according to the formula $$(L^*_{max}-L^*) \times a^*.$$

BRIEF DESCRIPTION OF THE FIGURES

The patent or application file contains at least one drawing executed in color. Copies of this patent or patent application publication with color drawing(s) will be provided by the Office upon request and payment of the necessary fee.

radiodermatitis. The threshold erythema values for grade 2 and 3 are given based on the subjective erythema grading.

Figure 6:
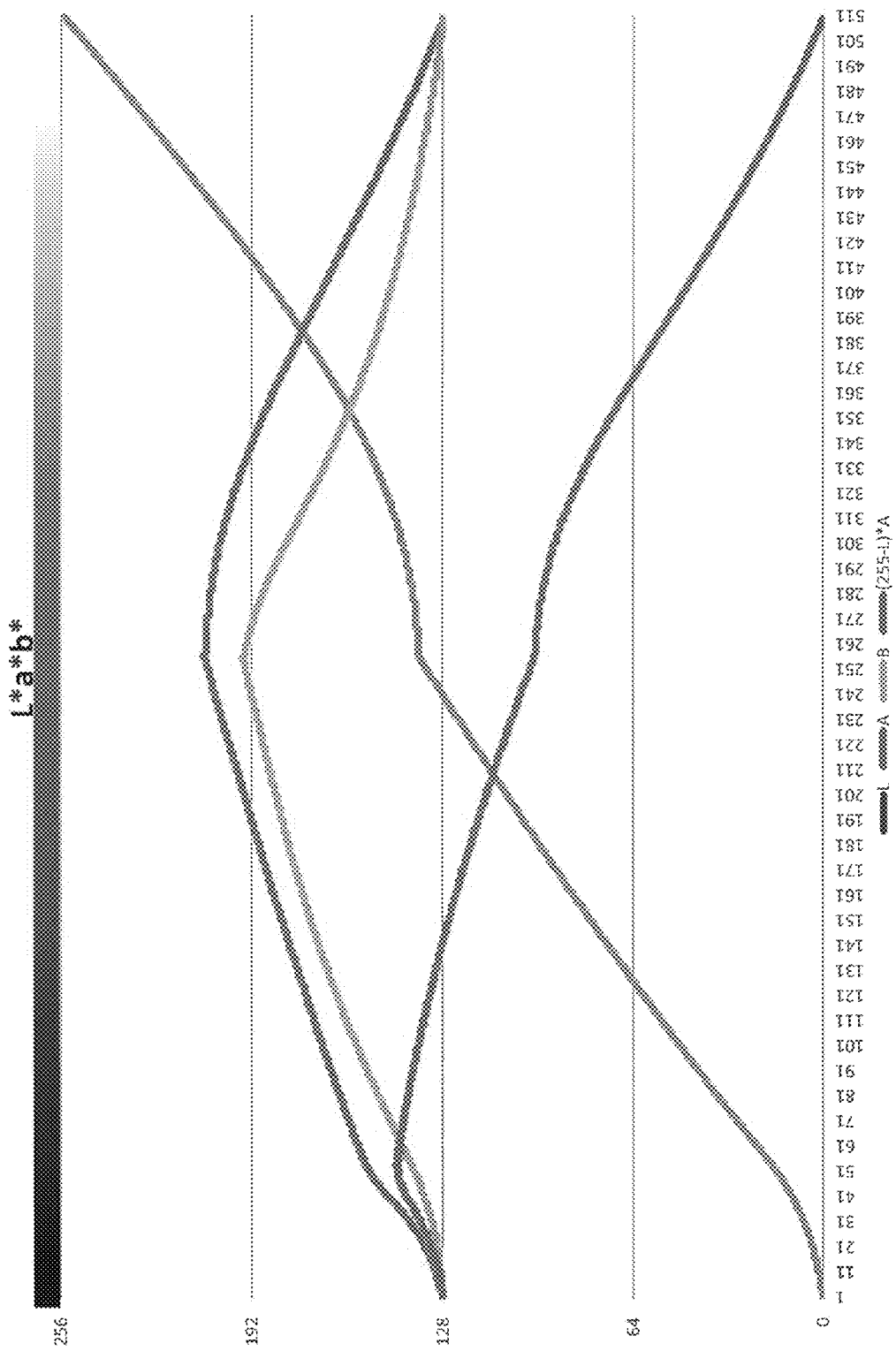

FIG. 6: Red color gradient (A) and calculated imaging variants based on an image with 8 bit per channel according to the L*a*b* color space (B).

Figure 7:
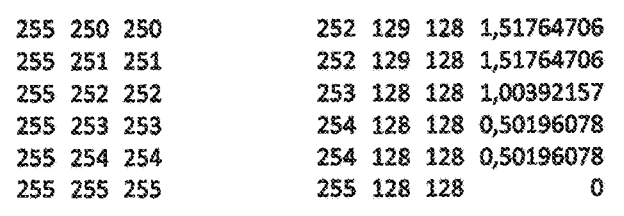

FIG. 7: Table comprising the color gradient as well as all values of the RGB and L*a*b* color space underlying said red color gradient.

Figure 8:
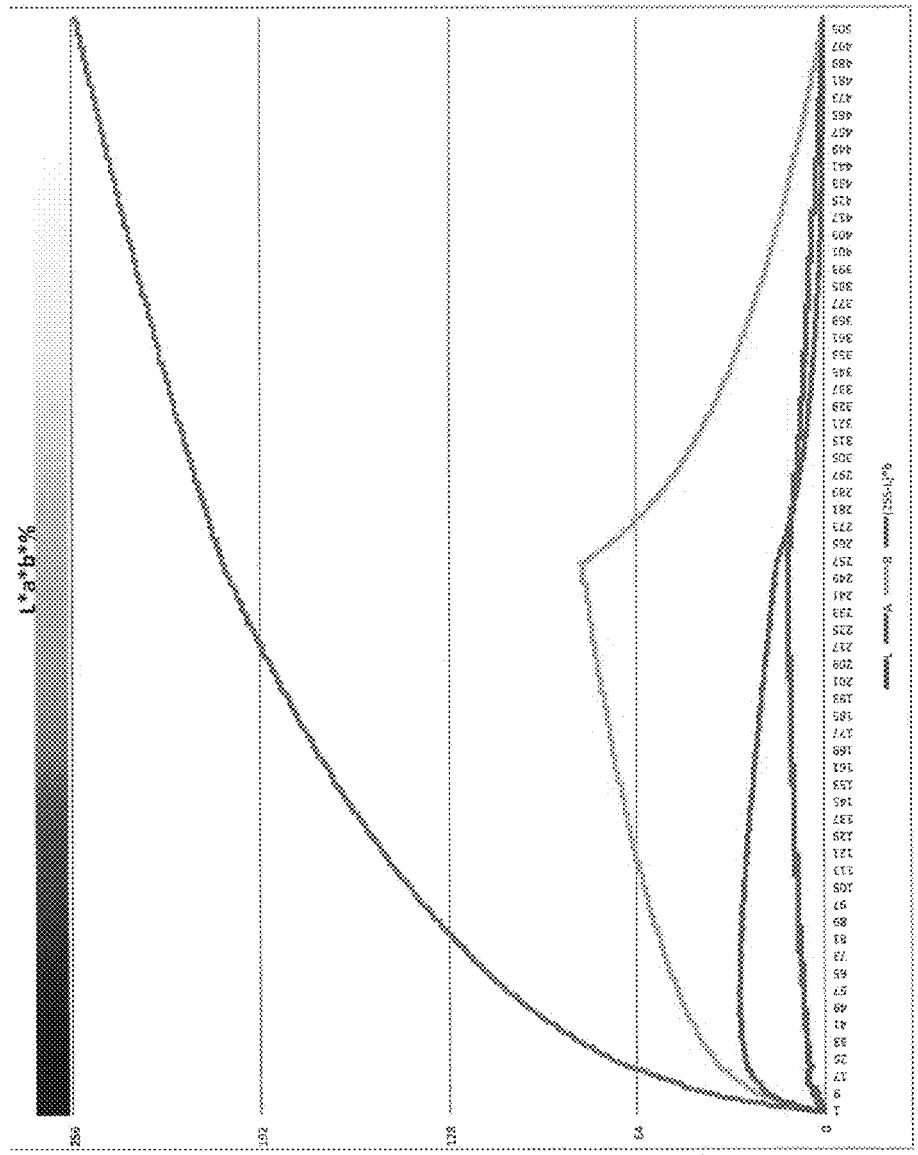

FIG. 8: Yellow color gradient (A) and calculated imaging variants based on an image with 8 bit per channel according to the L*a*b* color space (B).

FIG. 9: Table comprising the color gradient as well as all values of the RGB and L*a*b* color space underlying said yellow color gradient.

Figure 10:
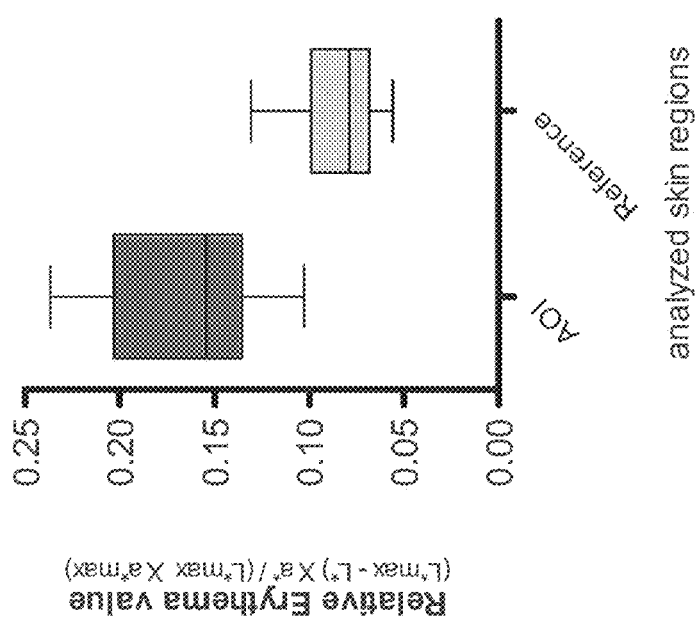
Figure 10:
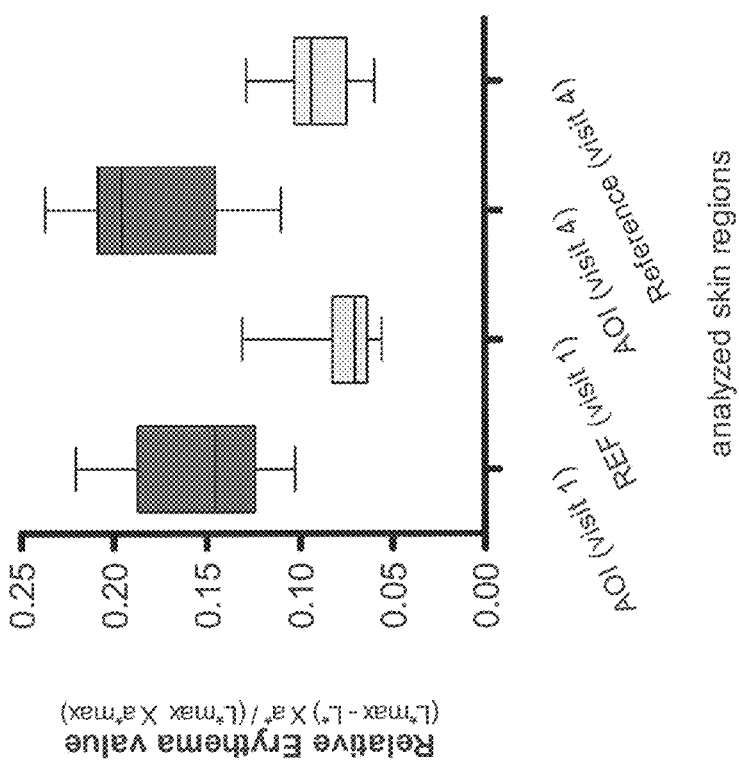

FIG. 10: Using a software app integrating the invented methods to analyse erythema values of Naevus lenticularis areas in a phase I trial (A) and time dependent changes of analyzed erythema values (B)

DETAILED DESCRIPTION OF THE INVENTION

The invention provides methods for analyzing skin color and methods for assessing erythema based on measuring the light reflectance of a skin or mucosal area and analyzing said measurement by using a novel formula to calculate the erythema value. The skin redness or erythema value provides an objective, continuous measure for skin redness or erythema over the entire range of intensities. Accordingly, the higher the skin redness erythema value the higher is the intensity of erythema.

The term "erythema" as used herein may comprise any skin or mucosal redness, or skin or mucosal irritation, or skin lesions. For example, erythema may include dermatitis (e.g. radiodermatitis), eczema, epitheliolysis, desquamation, redness, rubor, and/or rash. Erythema may also comprise any type of erythema, such as erythema ab igne, erythema chronicum migrans, erythema induratum, erythema infectiosum, erythema marginatum, erythema migrans, erythema multiforme, erythema nodosum, erythema toxicum, keratolytic winter erythema, palmar erythema, Stevens-Johnson syndrome, and toxic epidermal necrolysis (TEN, also known as "Lyell's syndrome") and Naevus flammeus nuchae. The term "erythema" further refers to skin lesions or wounds. The term "erythema" may also include wounds of any stage, i.e. fresh wounds, as well as wounds in different stages of wound healing.

Erythema may affect one or more layers of skin or mucosa, e.g. one or more layers of the epidermis and/or one or more layers of the dermis; or one or more layers of the mucous membranes, e.g. the mucosal epithelium (Lamina epithelialis mucosae) and/or the Lamina propria or the conjunctive tissue (e.g. sclera; conjunctiva of the eye).

The term "using a software application" as used in our invented methods can be recognized and understood in any context interchangeable for using a software app, or using an application program or using an application or using an app or a software tool or a web software or in more general words, the use of any software allowing to perform useful tasks which go beyond the running of the computer itself allowing the integration of our invented computational methods.

In a first aspect, the invention relates to a method for assessing erythema of a subject comprising the steps of
measuring the light reflectance of a skin or mucosal area of the subject,
obtaining the L* value and the a* value of said measurement according to the L*a*b* color space, and
calculating the erythema value according to the formula $$(L^*_{max} - L^*) \times a^*.$$

In a second aspect, the invention relates to a method for assessing the risk of a subject to develop erythema caused by irradiation comprising the steps of
measuring the light reflectance of a skin or mucosal area of said subject prior to irradiation,
obtaining the L* value and the a* value of said measurement according to the L*a*b* color space,
calculating the baseline erythema value according to the formula $$(L^*_{max} - L^*) \times a^*, \text{ and}$$

correlating said baseline erythema value to the risk of the subject to develop erythema caused by irradiation.

In a third aspect, the invention relates to a method for predicting the intensity of erythema that a subject develops due to irradiation comprising the steps of
measuring the light reflectance of a skin or mucosal area of said subject prior to irradiation,
obtaining the L* value and the a* value of said measurement according to the L*a*b* color space, and
calculating the baseline erythema value according to the formula $$(L^*_{max} - L^*) \times a^*, \text{ and}$$

correlating said baseline erythema value to the intensity of erythema that the subject develops due to irradiation.

In a fourth aspect, the invention relates to a method for predicting the time until a subject develops erythema caused by irradiation comprising the steps of
measuring the light reflectance of a skin or mucosal area of said subject prior to irradiation,
obtaining the L* value and the a* value of said measurement according to the L*a*b* color space,
calculating the baseline erythema value according to the formula $$(L^*_{max} - L^*) \times a^*, \text{ and}$$

inversely correlating said baseline erythema value to the time until the subject develops erythema caused by irradiation.

In an embodiment of the second, third and fourth aspect, the light reflectance of a skin or mucosal area of the subject is measured prior to irradiation. With regard to said embodiments, the term "prior to irradiation" refers to a time-point prior the start of irradiation exposure or at the beginning of irradiation, i.e. prior to the first irradiation, which may be a first irradiation in a course of several subsequent irradiations. The according erythema value is calculated based on said baseline measurement and is a baseline erythema value. The light reflectance of a skin or mucosal area of the subject may be measured at two or more time-points prior to irradiation, and an according mean baseline erythema value may be calculated. In an embodiment of the second, third and fourth aspect, the light reflectance of a skin or mucosal area of the subject is measured at one or more time-points following irradiation. The term following irradiation with regard to said aspects refers to one or more time-points within the initial period of irradiation, in particular, during the phase of the first few exposures to irradiation, or during the first few days of irradiation therapy. For example, the light reflectance of a skin or mucosal area of the subject is measured at one or more days during the first week of radiation therapy. The one or more erythema values are calculated based on said initial measurements, and may be defined as initial erythema values.

The term "correlating" as used herein refers to a direct relation of the erythema value to the respective other parameter. For example, the higher the baseline erythema value of a subject, the higher is the risk of the subject to develop erythema caused by irradiation, and/or the intensity of erythema that the subject develops due to irradiation.

The term "inversely correlating" as used herein refers to an inverse relation of the erythema value to the respective other parameter. For example, the higher the baseline erythema value of a subject, the shorter is the time until the subject develops erythema caused by irradiation, or the lower the baseline erythema value of a subject, the longer is the time until the subject develops erythema caused by irradiation.

The gradient between said baseline and/or initial erythema values may be calculated, e.g. between the baseline erythema value and one or more of said initial erythema values, or between two or more initial erythema values. The baseline erythema value, as well as said gradient may be correlated to the risk to develop erythema caused by irradiation, to the intensity of erythema caused by irradiation, or may be inversely correlated to the time until a subject develops erythema caused by irradiation. Accordingly, either the baseline erythema value, or the gradient between two or more erythema values, or a combination of both may be used to assess or predict these parameters. In one embodiment, the light reflectance is measured prior to irradiation and at one or more time-points following irradiation, the gradient between two or more erythema values is calculated, and said gradient is correlated to the risk of a subject to develop erythema caused by irradiation, or to the intensity of erythema that the subject develops due to irradiation, or inversely correlated to the time until the subject develops erythema caused by irradiation. In another embodiment, the risk of a subject to develop erythema caused by irradiation, the intensity of erythema that the subject develops due to irradiation, or the time until the subject develops erythema caused by irradiation is assessed or predicted based on the baseline erythema value and on the gradient between two or more erythema values.

In one embodiment, a prognosis for the subject is given for all three parameters based on one or more baseline and/or initial erythema values. Accordingly, the risk of the subject to develop erythema caused by irradiation is assed based on calculating the baseline and/or initial erythema value according to the invention and correlating it to said risk, the intensity of erythema that the subject develops due to irradiation is predicted based on calculating the baseline and/or initial erythema value according to the invention and correlating it to said intensity, and the time until the subject develops erythema caused by irradiation is predicted based on calculating the baseline and/or initial erythema value according to the invention and inversely correlating it to said time.

In a fifth aspect, the invention relates to a method for testing a pharmaceutical or cosmetic preparation for its ability to cause or treat erythema in a subject comprising the steps of
measuring the light reflectance of a skin or mucosal area of the subject prior to and following the administration of said pharmaceutical or cosmetic preparation,
obtaining the L* value and the a* value of each measurement according to the L*a*b* color space, and
calculating the erythema value for each measurement according to the formula $$(L^*_{max} - L^*) \times a^*.$$

In a sixth aspect, the invention relates to a method for testing a pharmaceutical or cosmetic preparation for its ability to ameliorate the appearance of erythema in a subject comprising the steps of
measuring the light reflectance of a skin area of the subject prior to and following the administration of said pharmaceutical or cosmetic preparation,
obtaining the L* value and the a* value of each measurement according to the L*a*b* color space, and
calculating the erythema value for each measurement according to the formula $$(L^*_{max} - L^*) \times a^*.$$

In an embodiment of the fifth or sixth aspect, the light reflectance of a skin or mucosal area of said subject is measured at least once prior to administration of the pharmaceutical or cosmetic preparation, and at one or more time-points following the administration pharmaceutical or cosmetic, and the erythema values are calculated for each measurement. The term "following the administration of said pharmaceutical or cosmetic preparation" with regard to said aspects refers to one or more time-points within and/or after the period of administration of the pharmaceutical or cosmetic preparation. For example, the light reflectance of a skin or mucosal area of the subject is measured at one or more time-points after single or repeated administration of the pharmaceutical or cosmetic preparation. The light reflectance of a skin or mucosal area of the subject may also be measured at one or more time-points after the period administration of the pharmaceutical or cosmetic preparation, i.e. when the pharmaceutical or cosmetic preparation is no longer administered. The gradient between two or more of said erythema values may be determined, e.g. between two or more subsequent measurements or erythema values, or between two or more measurements or erythema values over treatment or observation time. An increase of the erythema value between two or more erythema values over administration time indicates progression of erythema, i.e. that the pharmaceutical or cosmetic preparation causes erythema, or is not effective in preventing erythema. No significant change of the erythema value between two or more erythema values over administration time indicates a stable skin or mucosal condition, i.e. that the pharmaceutical or cosmetic preparation does not cause erythema, is effective in preventing erythema, is not effective in treating erythema, or is not effective in ameliorating the appearance of erythema. A decrease of the erythema value between two or more erythema values over administration time indicates regression of erythema, i.e. that the pharmaceutical or cosmetic preparation is effective in treating erythema, or in ameliorating the appearance of erythema.

In an embodiment of the sixth aspect, the opacity of a cosmetic product is tested. The cosmetic product may be make-up, a foundation, face powder, camouflage, a cover stick, or a concealer. A decrease of the erythema value after application of the product indicates that the cosmetic product is effective in covering erythema.

In a seventh aspect, the present invention provides a method for analyzing skin color of a subject comprising the steps of
measuring the light reflectance of a skin or mucosal area of the subject, obtaining the L* value and the a* value of said measurement according to the L*a*b* color space, and
calculating the skin redness value according to the formula $$(L^*_{max} - L^*) \times a^*.$$

In a major aspect of the above given invention the term "skin color" refers to skin or mucosal or conjunctiva color comprising any shades of red, especially skin redness or mucosal redness. Such skin redness includes healthy skin or mucosa or conjunctiva and irritations of the skin or mucosal or conjunctiva, such as e.g. erythema. Accordingly, the term "skin redness value" refers to the value calculated based on the measurement of skin or mucosal color. For example, the skin redness value may be defined as erythema value and referring to such aspect local or time dependent differences in the erythema value can be used to objectively analyze and interpret changes in context to Lentigo solaris or Lentigo simplex or Lentigo maligna or Lentigo aestiva of a subject.

In another aspect the definition "skin color" refers to skin or mucosa or conjunctiva color comprising erythema shades and further comprising shades of yellow pigmentation, especially in the skin or sclera (white of the eye). Such yellowish skin pigments are included in the normal healing process of a skin hematoma or can be observed in context to life threatening diseases e.g. Icterus (Jaundice). Slightly increased levels of bilirubin, the yellow breakdown product of haeme catabolism, is visually noticeable in the sclera at bilirubin levels of about 2 to 3 mg/dL (34 to 51 µmol/L) but much higher Bilirubin levels are required for reliable icterus assessment of the skin due to masking effects of normal skin pigmentation. Normal skin pigmentation however is considered in our method by obtaining the L* and b* value and calculating the yellowness value of the skin or mucosa according to the formula $(L^*_{max} - L^*) \times b^*$ providing a novel sensitive and non invasive method for objective documentation and assessment of icterus grading and development of a subject over time.

In another aspect the invented method may be used to assess the ability of a cosmetic preparation to tan the skin of a subject, i.e. to test a skin tanning preparation. Accordingly, the skin redness value (including the information of brightness, i.e. also considering the skin tanning) is calculated based on one or more measurements of a treatment area prior to and after the administration or usage of a skin tanning preparation. In said embodiment, the reference area may be an area that is not a treatment area, i.e. not covered by the cosmetic preparation.

In a more distant aspect the invented method may be used for analyzing meat.

In one embodiment of the present invention, the subject is a human. In one embodiment, the human is a Caucasian. In another embodiment, the subject is a non-human animal. The non-human animal may be a non-human mammal selected from the group consisting of non-human primates, pigs, rodents, or rabbits. In an embodiment, the subject is a pig, such as a minipig. In another embodiment, the subject is a nude mouse. In one embodiment, the subject is a human female breast cancer patient who receives radiation therapy. The breast cancer patient may have undergone surgery, e.g. breast-preserving surgery. In one embodiment, the subject is a human head and neck cancer (HNC) patient who receives radiation therapy. The HNC patient may have undergone surgery. In an embodiment, the subject is treated with chemotherapy.

In an embodiment, the subject is or will be treated with a treatment that may cause erythema, or is prone to erythema.

In another embodiment, the subject is or will be treated with a treatment that may cause erythema, or is prone to erythema, and is or will be treated with a treatment that prevents erythema. In still another embodiment, the subject is suffering from erythema and is or will be treated with a treatment that may treat erythema and/or ameliorate the appearance of erythema.

In an embodiment, the subject is or will be exposed to irradiation, or is suffering from or prone to radiation induced dermatitis or sunburn.

In one embodiment, the subject is or will be treated with cytotoxic drugs, such as e.g. fluorouracil, capecitabine, cytarabine, sorafenib, or pegylated liposomal doxorubicin (Doxil), or tyrosine kinase inhibitors (e.g. sorafenib and sunitinib). For example, the subject may suffer from or is prone to palmar-plantar erythrodysesthesia or hand-foot syndrome.

In an embodiment, the subject is or will be treated with a drug that may cause erythema, such as e.g. antibiotics (sulfonamides, penicillins, cefixime), barbituates, lamotrigine, phenytoin (e.g., Dilantin), nonsteroidal anti-inflammatory drugs (NSAIDs); or EGFR inhibitors. For example, the subject is or will be treated with an anti-EGFR antibody therapy, especially with cetuximab (Erbitux®).

In an embodiment, the subject is or will be exposed to one or more allergens, such as e.g. various allergens for allergy testing, urushiol (a resin produced by poison ivy and poison oak), penicillin, latex, or wasp, fire ant and bee stings.

In an embodiment, the subject is suffering from a fungal infection, such as e.g. tinea (ringworm), or candida.

In an embodiment, the subject is suffering from a bacterial infection, e.g. with staphylococcus, streptococcus, or by a treponemal disease, such as e.g. syphilis, bejel, pinta and yaws.

In an embodiment, the subject is suffering from a viral infection, which may be selected from the group consisting of shingles, rubella, herpes, hand-foot-mouth disease, enterovirus infection, chickenpox infection, or infection by erythrovirus (erythema infectiosum or fifth disease).

In an embodiment, the subject is suffering from a skin disease, which may be selected from the group consisting of psoriasis, atopic eczema or atopic dermatitis (neurodermatitis), eczema, or acne.

In an embodiment, the subject is suffering from a disease affecting internal or external mucosa, e.g. oral, nasal, or intestinal mucosa. For example, the subject is suffering from inflammatory bowel disease, Morbus Crohn (or Crohn's disease), aphthous stomatitis, conjunctivitis, chronic obstructive pulmonary disease, peptic ulcers, alcohol abuse, or gastritis.

In an embodiment, the subject is suffering from a somatoform disorder, such as blushing.

In an embodiment, the subject will have or has one or more wounds. Said wounds may be of any origin (e.g. surgery or injury), as well as of any stage, i.e. fresh wounds or wounds in any stage of wound healing. A wound is a type of injury in which skin is torn, cut, or punctured (an open wound), or where blunt force trauma causes a contusion (a closed wound). In particular, a wound is an injury which damages the epidermis and/or dermis of the skin. However, the wound may also be a mucosal lesion or injury. In general, the wound may affect one or more layers of skin or mucosa, e.g. one or more layers of the epidermis and/or one or more layers of the dermis; or one or more layers of the mucous membranes, e.g. the mucosal epithelium (Lamina epithelialis mucosae) and/or the Lamina propria.

Thus, in an aspect, the present invention can be applied for documenting or analyzing wounds or wound healing of a subject or for documenting hematoma intensity or hematoma development of the skin or mucosa or conjunctiva of a subject over time. This may be done with the inventive method
comprising the steps of
measuring the light reflectance of a skin or mucosal area of the subject,
obtaining the L* value and the a* value of said measurement according to the L*a*b* color space, and
calculating the erythema value according to the formula $$(L^*_{max} - L^*) \times a^*.$$

In one embodiment, the skin or mucosal area is a skin area. In another embodiment, the skin or mucosal area is a mucosal area. The mucosal area may be an external or internal mucosa, e.g. nasal, oral, intestinal mucosa. In an embodiment, the skin or mucosal area is a gross area comprising one or more segment areas. In said embodiment, each step of the methods of the invention is done separately for each segment area. Accordingly, the erythema value is calculated for each segment area according to the invention.

In one embodiment, the erythema value or any other skin color value may be calculated separately for each subarea. A subarea may a subarea as described below, or—if the light reflectance of a skin or mucosal area is measured by obtaining an image, a subarea may also be a single pixel of said image, i.e. the erythema value is calculated for one or more single pixels. Accordingly, a mean erythema value or a mean value of any other skin color value may be calculated of one or more single pixels of the image, the gross area, and/or the segment area.

The segment area may be an erythema area (or a representative part of an erythema area). In one embodiment, the erythema area is an area being prone to erythema, which may e.g. be caused by a disease and/or treatment as further described below. In another embodiment, the erythema area is an area characterized by erythema. Said erythema may have been caused by a disease and/or treatment as further described below. The term "treatment" must be realized in this context as a required therapeutic treatment of a subject which may be a local treatment (e.g. of the skin or mucosal area of the subject), or a systemic treatment of the subject (e.g. a treatment with an anti-EGFR antibody). Accordingly, in an embodiment, the segment area prone to erythema or characterized by erythema may be the analyzed treatment area of a local treatment, or the analyzed area at which the erythema occurs upon systemic treatment.

The analyzed segment area may also be a treatment area (or a representative part of a treatment area), i.e. an analyzed area that is or will be physically and/or chemically treated, e.g. with irradiation (including but not limited to x-ray, ultraviolet, and/or solar irradiation), and/or with a pharmaceutical and/or cosmetic preparation. In one embodiment, the analyzed erythema area is also a treatment area. In an embodiment, the irradiation is radiotherapy, especially fractionated radiotherapy.

An analyzed segment area may also be a reference area (or a representative part of a reference area). Said reference area may be an area of the same subject. In an embodiment, the reference area may be an area of one or more subjects other than the subject to be assessed. Said different subjects may be of the same race (e.g. Caucasian), of the same or similar skin color, and/or of the same skin type (e.g. according to the Fitzpatrick Skin Scale). In an embodiment, said different subjects have the same kind of skin condition, e.g. erythema. In still another embodiment, said different subjects suffer from the same or a similar disease and/or undergo the same or similar treatment. Accordingly, a reference curve of two or more reference erythema values may be generated for comparison to the subject's measurements. In general, for any comparison of erythema values (e.g. to reference values), the area under the curve between two or more erythema values may be determined and compared to e.g. the area under the curve of two or more reference erythema values.

Furthermore, The reference area may be an area similar to the erythema and/or treatment area, i.e. an area of the same or a similar region of the body, and/or of the same or similar nature (e.g. of similar color and/or shape). In one embodiment, the reference area is adjacent to the segment area to be compared to, e.g. the erythema and/or treatment area. In one embodiment, the reference area is of the same size as the segment area to be compared to, e.g. the erythema and/or treatment area. The erythema value calculated for a reference area may also be called reference erythema value. In an embodiment, the reference area is not an erythema area, for example, if the method of the present invention is used to assess a treatment that may cause erythema. In said embodiment, the reference area is not characterized by erythema, i.e. is free from erythema. For example, the reference area may be the treatment area prior to treatment with a preparation or treatment that may cause erythema, thus, prior to development of erythema. In one embodiment, the reference area is not a treatment area. In an example, the reference area is left completely untreated. In a further embodiment, the reference area is treated with a placebo or with a reference treatment, such as e.g. the gold standard treatment or a competitive or comparative product. In another embodiment, the reference area is characterized by erythema, for example, if the method of the present invention is used to assess a treatment that may ameliorate erythema. In another embodiment, the reference area is an erythema and/or treatment area prior to development of erythema and/or prior to treatment. The reference erythema value calculated for a reference area that is an erythema and/or a treatment area, but based on a measurement prior to development of erythema and/or prior to treatment, may also be called baseline erythema value or initial erythema value.

In an embodiment, the erythema value is compared to a reference erythema value. For example, the erythema value of a segment area (e.g. a treatment and/or erythema area) is compared to one or more reference erythema values. In one embodiment, the reference erythema value is calculated based on one or more reference areas. In another embodiment, the reference erythema value is the erythema value of the same segment area from which the follow-up erythema value is calculated, e.g. an erythema and/or treatment area, assessed prior to treatment and/or development of erythema.

In another embodiment, the erythema value may be compared to more than one reference erythema values and/or one or more reference gradients between two or more erythema values of reference areas. Said reference erythema values and/or reference gradients may include reference erythema values of the same subject or of one or more different subjects. For example, a reference erythema gradient, or a rating or reference curve may be determined from subjects with the same or similar type and/or grade of erythema, e.g. with the same disease or treatment. Accordingly, the erythema of a subject may be assessed by calculating one or more erythema values according to the invention and comparing said one or more erythema values to one or more reference erythema values, a reference erythema gradient between two or more reference erythema values, and/or to a rating or reference curve.

The light reflectance of the skin or mucosal area may be measured by using an imaging method, such as digital photography. Accordingly, in an embodiment, the light reflectance of a skin or mucosal is measured by obtaining an image of said skin or mucosal area. The image may be a raster graphics image (or bitmap). Accordingly, in one embodiment, the steps of obtaining the L* value and the a* value of said measurement according to the L*a*b* color space, and calculating the erythema value according to the formula of the invention are done per pixel, i.e. separately for one or more pixels of the skin or mucosal area. For example, the image may comprise a gross area comprising one or more segment areas, and the erythema values are calculated for one or more pixels of said area. The erythema value may be calculated for all pixels that are representative of said skin or mucosal area, or of each pixel of said skin or mucosal area. The erythema value may be calculated for each pixel of the image. Optionally, one or more pixels may be excluded, e.g. any pixels of non-representative subareas may be excluded, as further described below. Based on the single pixel erythema values, a mean erythema value may be calculated for the skin or mucosal area. In an embodiment, the mean erythema value is the arithmetic mean of single pixel erythema values of the skin or mucosal area.

In one embodiment, the light reflectance is measured in the L*a*b* color space and the L* value and the a* value are obtained directly from said measurement.

In another embodiment, the light reflectance is measured in a color space other than the L*a*b* color space, and the L* value and the a* value according to the L*a*b* color space are obtained by converting the light reflectance values of said measurement into the corresponding values of the L*a*b* color space.

In one embodiment, the light reflectance values of one or more pixels of the image according to the color space of the measurement are obtained directly from the image file. In an embodiment, the light reflectance values of each single pixel of the image are obtained. In another embodiment, said one or more single pixel values are obtained by using a graphics software, such as Adobe Photoshop, Corel Paint Shop, Corel Photo Paint, Irfan View, GIMP, Paint.NET, or the like.

In one embodiment, a mean erythema value based on single pixel erythema values is calculated for each segment area. In one embodiment, a mean erythema value based on single pixel erythema values is calculated for each reference area. In another embodiment, a mean erythema value based on single pixel erythema values is calculated for each gross area. Furthermore, a mean erythema value may be calculated for more than one segment areas, reference areas, and/or gross areas. The mean erythema value may comprise all single pixel erythema values of the skin or mucosal area, e.g. the segment area. However, in an embodiment, one or more single pixel erythema values may be excluded from the calculation of the mean erythema value.

In general, any of the above described methods for measuring the light reflectance of a skin or musosal area may be combined with laser scanning, such as e.g. 3D laser scanning, to obtain further information of the skin or mucosal area, such as the 3D structure.

In one embodiment, the erythema area is a treatment area that is or will be (locally) treated with a physical and/or chemical treatment that may cause erythema. For example, the physical and/or chemical treatment may be selected from the group consisting of irradiation, systemic treatment (e.g. subcutaneous, mucosal, intramuscular injections), or topical treatment (including mucosal administration) with a pharmaceutical and/or cosmetic preparation, allergy tests, such as e.g. a Prick test, and/or a patch test. In said embodiment, the erythema area is an area prone to erythema. Furthermore, in said example, the erythema area is also a treatment area. In said example, a respective reference area is not characterized by erythema. Accordingly, the reference area may be the same area as the erythema area, but prior to treatment. If the reference area is an area other than the erythema area, the reference area is not a treatment area.

In an embodiment, the treatment area is an erythema area characterized by erythema that is or will be treated with a pharmaceutical or cosmetic that may ameliorate the erythema, e.g. a preparation comprising one or more antibiotic, anti-inflammatory, wound-healing, and/or anti-oxidant agents. In said embodiment, the reference area is an erythema area characterized by erythema that is not a treatment area, i.e. that is not treated with the pharmaceutical or cosmetic. In one embodiment, the anti-oxidant agent is superoxide dismutase (SOD), especially recombinant human Cu/Zn SOD, optionally in a liposomal formulation.

In another embodiment, the treatment area is an erythema area characterized by erythema that is or will be topically treated with a cosmetic preparation to cover the erythema, e.g. a preparation comprising one or more pigments, such as make-up, foundations, face powder, camouflage, cover sticks, concealers. In said embodiment, the method according to the present invention may be used to assess the opacity of the cosmetic preparation. In said embodiment, the reference area is an erythema area characterized by erythema that is not a treatment area, i.e. not covered by the cosmetic preparation.

In another embodiment, the treatment area is an area prone to erythema (e.g. an area that is or will be exposed to sun) that is or will be topically treated with a cosmetic preparation to prevent erythema, e.g. a sun care preparation. In said embodiment, the method according to the present invention may be used to assess the ability of the cosmetic preparation to prevent sunburn. In said embodiment, the reference area may be an area that is or will be exposed to sun that is not a treatment area, i.e. not covered by the cosmetic preparation. A segment area may be determined and/or analyzed based on a software, such as a computer-based manual selection or de-selection tool (e.g. a graphic selection or de-selection tool, for example, a linear, circular, elliptical, rectangular, or polygonal selection or de-selection tool), and/or an automated or semi-automated pattern recognition and/or analysis software (or image recognition and/or analysis software). For example, certain representative areas may be selected and/or certain non-representative areas may be deselected. An example of a semi-automated image analysis is the above referenced Wound Healing Analyzing Tool (W.H.A.T) software.

In general, certain subareas may be excluded from a segment area and/or the gross area. Accordingly, such subareas may be excluded from the calculation of the respective EV.

In an embodiment, one or more subareas are manually or automatically excluded from the segment and/or gross area. Such subareas may be any non-representative area (e.g. a border area), or an area with a pigmentation, shade, and/or shape different from the remaining area to be analyzed. The subarea may e.g. be characterized by a scar, a nevus, a freckle, an age spot, a skin fold (e.g. the inframammary fold (IMF), also called inframammary crease or inframammary line), an acromastium, a shadow, a plaster, and/or a mark (such as a patch, a tattoo, an ink mark, e.g. a radiation mark), or parts thereof. Such subareas may be excluded by a computer-based manual selection or de-selection tool (e.g. a graphic selection or de-selection tool, for example, a linear, circular, elliptical, rectangular, or polygonal selection or de-selection tool), and/or by using automated or semi-automated image recognition techniques, such as a pattern recognition software (or an image recognition software).

A representative part of a segment area may be a subarea of said segment area that shows the main characteristics of the segment area. A representative part of a segment area may be a central subarea of said segment area. Such representative part of a segment area may not include any border areas, e.g. border areas to the surrounding areas, e.g. other segment areas. A representative part of a segment area may also be a segment area, from which one or more non-representative subareas have been excluded. In general, two or more segment areas may or may not overlap. For example, two or more segment areas may partially overlap. Also, any non-representative area may overlap with two or more segment areas, and thus, may be excluded from the gross area comprising said two or more segment areas.

If the light reflectance is measured by obtaining an image of the skin or mucosal area, the above described selection or de-selection of subareas can be applied to the pixels of the image, i.e. one or more or all pixels of a non-representative subarea may be deselected, or one or more or all pixels of a representative subarea may be selected. Accordingly, said one or more pixels of the non-representative subarea may be excluded from calculating the erythema value, e.g. from calculating the single pixel erythema value and/or the mean erythema value for the segment area. Furthermore, said one or more pixels of the representative subarea may be included into the calculation of the the erythema value or any other color value, e.g. the single pixel erythema value and/or the mean erythema value for the segment area.

In one embodiment, the gross area comprises at least one erythema and/or treatment area. In one embodiment, the gross area comprises at least one reference area. In one embodiment, the gross area comprises at least one erythema and/or treatment area, and at least one reference area.

The gross area and/or the segment area may be a predetermined area. The gross area and/or the segment area may be marked, e.g. by one or more patches, tattoos and/or ink marks.

The light reflectance of a skin or mucosal area may be measured or represented in any color space, i.e. the measurement method or imaging method (and thus, the representation of the measurement or image) may be based on any color space (or color model), such as e.g. the CIE-Lab (or L*a*b*) color space, the XYZ color space, the Yxy color space, the Luv color space (e.g. the CIE-Luv color space, also designated L*u*v*), the RGB color space, the RYB color space, the CMYK color space, HSL, HSV and/or the CIECAM02 color space. The L*a*b*, the XYZ, and the Luv color spaces are independent of the device, with which the light reflectance is measured. In one embodiment, the light reflectance of a skin or mucosal area is measured in the L*a*b* color space. The measurement or image is represented in the L*a*b* color space and the parameters or values are L* (brightness), a* (red/green) and b* (blue/yellow). In said embodiment, the erythema value can directly be calculated based on the actually measured values for brightness (L*values) and redness (a* values). If the light reflectance of a skin or mucosal area is measured in a color space other than the L*a*b* color space, and the measurement or image is represented in a color space other than the L*a*b* color space, the actually measured values (or parameters) are converted into the respective values of the L*a*b* color space. For example, a measurement or image in the RGB or CMYK color space may be converted into the L*a*b* color space. The RGB or CMYK values first need to be converted to a specific absolute color space, such as sRGB or Adobe RGB. This adjustment may be device dependent, but the resulting data from the transformation may be device independent, allowing data to be converted to the CIE 1931 color space and then converted into L*a*b*. Methods and tools for conversion of values between different color spaces are provided e.g. by the ColorSync service program of Apple, the "Convert to Profile dialog" in Adobe Photoshop (http://www.photoshop.com/), and the easy RGB color calculator (http://www.easyrgb.com/).

Figure 1:
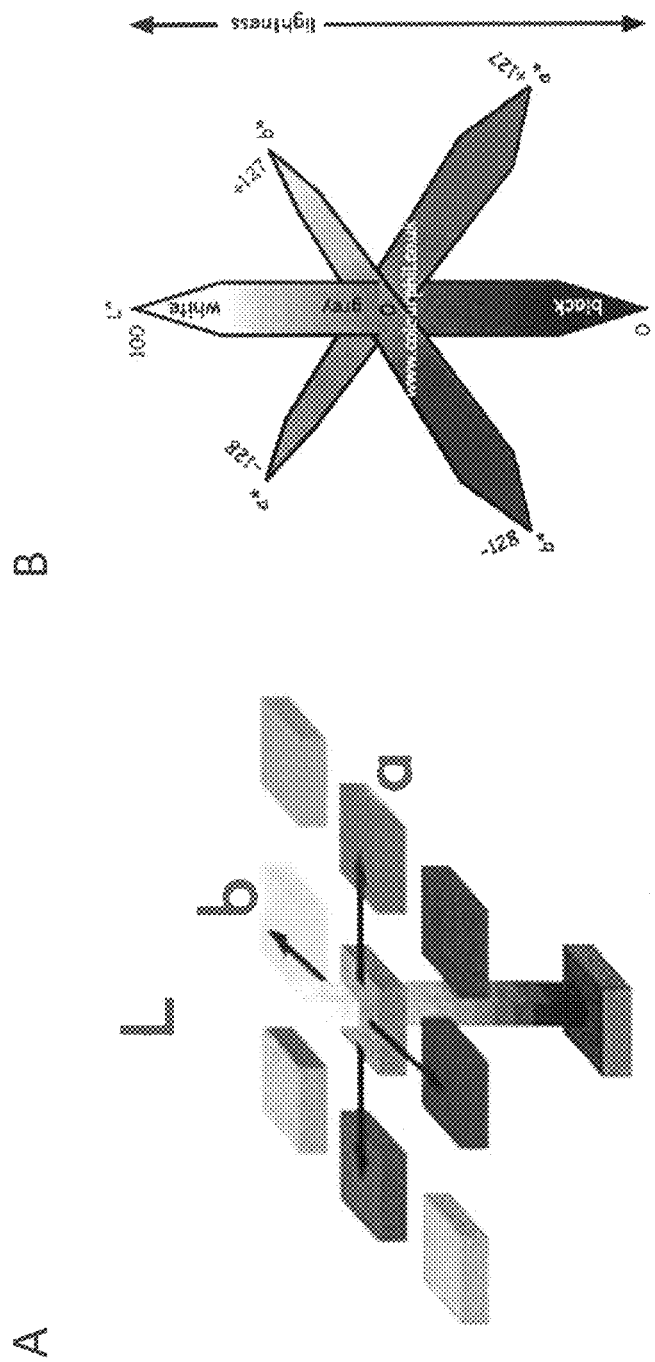
FIG. 1: Graphical representations of the L*a*b* color space.

The color space may be the L*a*b* color space, as approved by the French Commission Internationale de l'Éclairage (CIE) (also designated CIE 1976 L*a*b* or CIELAB; see e.g. ÖNORM EN ISO 11664-4:2008, edition 2012 May 15). It describes all the colors visible to the human eye and was created to serve as a device-independent model to be used as a reference. The three coordinates of the color space represent the lightness of the color (L*=0 yields black and L*=100 indicates diffuse white), its value between red and green (a*, negative values indicate green while positive values indicate red), and its value between yellow and blue (b*, negative values indicate blue and positive values indicate yellow). The color saturation increases with increasing distance of the center. Accordingly, each color can be represented in said three-dimensional color system by one single point, i.e. each color can be represented by the three parameters (or coordinates). FIG. 1 shows two graphical representations of the L*a*b* color space.

With reference to the CIELAB color space the a* scale ranges from maximal green saturation ($a_{min}$) to maximal red saturation ($a_{max}$) whereas the b* scale ranges from maximal blue saturation ($b_{min}$) to maximal yellow saturation ($b_{max}$). In the present invention the maximal values (i.e. $L_{max}$, $a_{max}$, and $b_{max}$) and the minimal values ($a_{min}$ and $b_{min}$) are determined on the one hand by the measurement method or imaging method and on the other hand by the respective color space and its color depth. The color depth (or bit depth) is the number of bits used to indicate the color of a single pixel of a bitmap, video frame buffer, or image. This concept is usually quantified as bits per pixel (bpp), which specifies the number of bits used. Color depth is only one aspect of color representation, expressing how finely levels of color can be expressed (also known as color precision); the other aspect is how broad a range of colors can be expressed (the gamut). The definition of both color precision and gamut is accomplished with a color encoding specification which assigns a digital code value to a location in a color space.

In one embodiment, the light reflectance is measured in a single spot measurement. From such single spot measurement, one single L* value and one single a* value are obtained, and the erythema value is calculated based on said single spot values. In another embodiment, the light reflectance is measured by obtaining an image of the skin or mucosal area. Said image comprises multiple pixels and each pixel is defined by the color parameters of the color space in which the measurement is taken. Thus, each single spot measurement or each pixel of a measurement or of an image may be defined by the parameters or values of the respective color space, e.g. the L*a*b* color space. If the single spot measurement or single pixel is defined by parameters or values of a color space other than the L*a*b* color space, the parameters or values are converted into the L*a*b* color space, as described above.

For example, the measurement method is spectrophotometry. Spectrophotometry is a single spot measurement, i.e. the skin or mucosal area is measured in one spot. The area which is measured in said spot is predefined by the target mask of the spectrophotometer. In an embodiment, the spectrophotometer has 32 diodes measuring the spectrum of about 400 to 700 nm in 10 nm steps. The spectrophotometry may be based on the L*a*b* color space. Accordingly, this single spot spectrophotometric measurement results in one single L*, a*, and b* value according to the L*a*b* color space. In one example, the data obtained from the spectrophotometer are directly provided in the L*a*b color space. In an example, the spectrophotometer has a maximal value of brightness, i.e. $L_{max}$, of 100. In said example, the maximal value of redness, i.e. $a_{max}$, is 127 (see FIG. 1B).

In another example, the measurement method or imaging method is digital photography. The color depth may e.g. be 8, 12, 15, or 16 bit per channel (or per color parameter). In an embodiment, the color depth is 8 bit per channel, i.e. 24 bit in total. If the color depth is 8 bit per channel, there are 256 possible values for each parameter (L*, a*, and b*). Accordingly, in said example the maximal L* value is 255 (since the lowest value is 0). The a* value representing the two colors red and green also comprises 256 possible values (i.e. 0-255). Thus, the minimal value for red is 128 and the maximal value for red is 255. The maximal value for brightness and redness may be calculated accordingly for any given color depth and/or color space. Based on said maximal L* and a* values, the calculated erythema values may be normalized.

The measurement or image may be obtained by any suitable measurement method or imaging method, such as e.g. spectrophotometry, video, video frame buffer, and/or photography. For example, the measurement or image may be obtained by a method not requiring any direct contact with the gross area and/or segment areas, e.g. photography. In an embodiment, the measurement or image is obtained by spectrophotometry and/or photography. In an embodiment, the measurement or image is obtained by digital photography.

In one embodiment, the image is obtained by using the CM-700d spectrophotometer from Konica Minolta. In one embodiment, the image is obtained by using the digital camera Canon powershot G12 from Canon. In one embodiment, the image is obtained by using a digital camera and the SOLIGOR ring flash from Canon.

For example, the spectrophotometry may be single spot spectrophotometry. The spectrophotometric measurement may be done under standardized conditions. For example, the personnel conducting the measurement is allocated and trained accordingly, the gross are to be measured may be standardized (e.g. predefined), the illumination area (i.e. the measurement area) is predefined (e.g. by a 8 mm target mask), and the spectrophotometer is calibrated prior to each measurement (e.g. an automatic white balance is done prior to each measurement).

In another embodiment, the photography is digital photography. The measurement or image may be obtained by using one or more devices selected from the group consisting of a digital camera, a flash (e.g. a ring flash), and a spectrophotometer.

The measurement or image may also be obtained by using endoscopic devices. In one embodiment, the skin or mucosal area is an internal mucosal area and the light reflectance is measured by endoscopic methods. For example, the methods according to the present invention may be used to diagnose and monitor diseases affecting internal mucosa and their treatment, such as e.g. Morbus Crohn.

The image may be obtained under standardized conditions, such as the imaging method and equipment, the settings of the imaging devices, the positioning of the object and the imaging device (i.e. the image perspective), and the light exposure. For example, a flash may be used for standardization to improve color contrast and to reduce shading effects. In an example in which several images are compared (e.g. several images of the same area at different time-points, and/or several images of different areas, either at the same or at different time-points), the images may be obtained in the same room, in which the lamps are on (either all available lamps or certain predefined lamps), and in which the window curtains and/or shades are closed (either all available window curtains and/or shades or certain predefined window curtains and/or shades). In one embodiment, the internal flash of the camera is deactivated and a standardized external flash is activated. This is especially important if different cameras are used for several images. The settings of the imaging device may be standardized, such as e.g. the image size, image format, image color scheme, flash, auto and/or scene modes, white balance, zoom, image focus, ISO sensitivity, shutter speed, image color parameters, etc. Furthermore, the image section, as well as the distance and orientation between the camera and the object or area may be standardized. For example, the image size may be 4:3 with 3648×2736 pixel; the image format may be raw, the image color scheme may be neutral, the internal flash may be deactivated, the external flash may be activated, the mode may be set to auto, the white balance may be set to auto, the zoom may be deactivated, the image focus may be set to autofocus TTL, the ISO sensitivity may be set to a defined value (e.g. a value between 200 and 400), the shutter speed may be set to auto, and/or the image color parameter is set to neutral. In one embodiment, the ISO sensitivity is 200. In general, the ISO sensitivity may be as low as possible. In one embodiment, the distance between the camera and the object or area is at least 2 m. In general, the distance between the camera and the object or area should be selected based on the power of the flash, i.e. to ensure that the flash (e.g. the camera-internal flash or the external flash) is able to adequately illuminate the object or area.

Also, the preparation of the measurement device or imaging device may be standardized, e.g. the method for disinfection of the measurement diaphragm of a spectrophotometer. Also, the pre-treatment of the gross area and/or one or more segment areas prior to obtaining the image may be standardized, e.g. covering, uncovering, cleaning, drying and/or disinfection of the gross area and/or one or more segment areas. The measurement or imaging conditions may be further standardized by selecting the same personnel for obtaining the measurements or images, and by properly training said personnel in all standardization conditions.

In an embodiment, the image represents the gross area.

The image may also comprise an identification object, such as a patient identification card, a hospital bar code, a QR code or the like.

In one embodiment, the image is saved in a format that is uncompressed, or lossless or nearly lossless compressed, i.e. comprises minimally processed data from the image sensor of the imaging device (e.g. camera, scanner, etc.). In an embodiment, the image is saved in a Raw format. In another embodiment, the image is saved in a Tif format. The image may be exported, e.g. for further analysis or visualization, in a format other than Raw format. For example, the image may be converted in a format selected from the group consisting of Tif, Png, or other lossless compressed image formats. In one embodiment, the image is saved in a Raw format, first converted into a Tif format, and the Tif format is then converted into an Png format. In one embodiment, the conversion from the Raw format to a format for exportation is a lossless or nearly lossless compression. This can be achieved e.g. by using a suitable Raw converter or graphics software, such as Adobe Photoshop, Corel Paint Shop, Corel Photo Paint, Irfan View, GIMP, Paint.NET, or the like. For pure visualization, the image may also be converted in any other suitable format, such as e.g. Jpeg.

In order to adjust any potential differences in imaging devices, light exposure, or other variable imaging conditions, the image may comprise a standard reference object, such as a color calibration tool (e.g. a gray card and/or a color card). In one embodiment, the color calibration tool is a QP calibration card, as described for example in EP 1240549, WO2004/028144, and/or PCT/SE2011/050367.

Accordingly, the data underlying the erythema value, e.g. the L* and a* values, may be normalized to a reference, such as a color calibration tool.

In one embodiment, the erythema value are normalized based on the maximal values for a* and L*.

For example, the erythema value may be converted into a relative value compared to the respective maximal value, which is set to 100%, in order to compare several erythema values based on different measurement methods or imaging methods, and/or based on different color depths.

Figure 2:
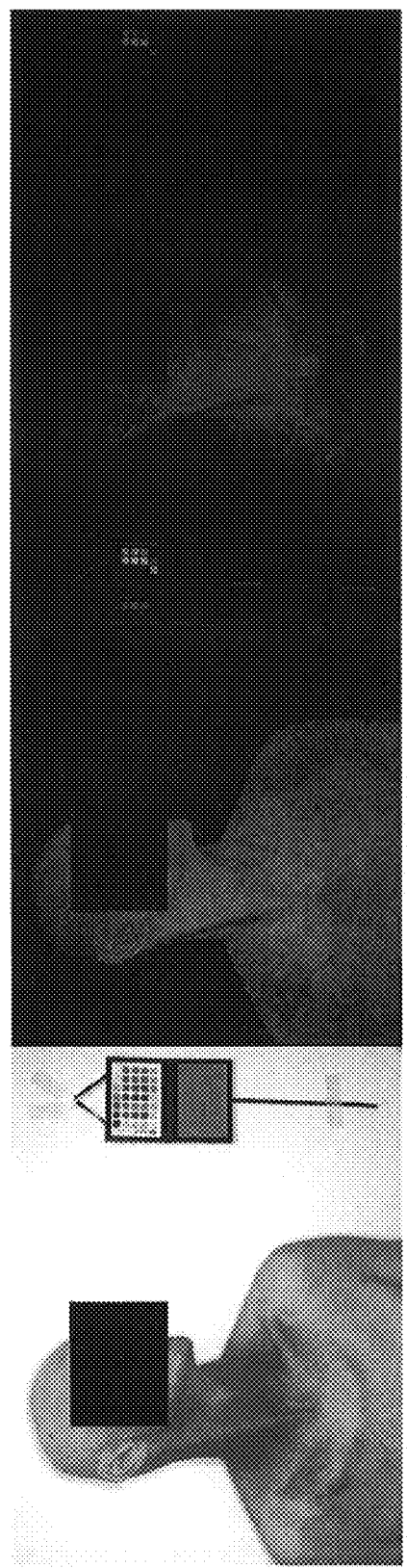
FIG. 2: Original photo and pseudo grey scale images based on the a* value and on the erythema value calculated by the novel algorithm the for improved visualization of erythema.

Optionally, the image may be converted into a false color image in order to visualize and/or analyze skin redness or erythema or ancillary assessed color values. For example, the image may be converted into a pseudo color image (similar to the color image provided by an infrared camera), e.g. a pseudo gray scale or pseudo red scale image, in which the erythema value is represented in gray scale or red scale (see FIG. 2). In said false color image, any "non-red" a* value (or negative a* value; e.g. representing green color in the L*a*b* color space) may be set to a pre-defined value. In an embodiment, any negative a* value is set to the minimal red value. For example, if the color space is the L*a*b* color space and the color depth is 8 bit per channel, then any a* value of 127 or lower may be set to 128. Such false color image may also be used to detect overexposure. Such overexposed images may then be excluded from analysis.

In one embodiment, the L* value decreases with increasing erythema intensity. In a further embodiment, the a* value increases with increasing erythema intensity. In another embodiment, the L* value decreases and the a* value increases with increasing erythema intensity.

In an embodiment, only the L* and the a* values are considered. In said embodiment, the erythema or skin color is assessed solely by using the L* and the a* value, and accordingly, the erythema value or skin redness value or redness value is calculated solely based on the L* and the a* value. However, since the a* value of the L*a*b* color space may include negative a* values representing green color, green color may be considered as well in the methods of the present invention. Since in skin or mucosa usually the positive a* values (or red values) prevail over negative a* values (or green values), it is not necessary to exclude any negative a* values because of their insignificant influence on the mean erythema value of the skin or mucosal area. In one embodiment, all a* values are considered, i.e. negative as well as positive a* values. Thus, in one embodiment, any pixels of an image having a negative a* values are included into the calculation of the mean erythema value. However, in another embodiment, only positive a* values are considered. According to said embodiment, any pixels of an image having a negative a* value are excluded from the calculation of the mean erythema value. Any other parameters are disregarded, such as e.g. the values for yellow, blue or any other color. According to said embodiment, the erythema value is calculated exclusively based on the values for brightness (from black to white) and redness (which may include the values for green), e.g. the L* value and the a* value.

In an embodiment, the erythema value provides a continuous erythema intensity measure without any grading or steps, i.e. not depending on any predefined grades.

In one embodiment, the methods of the invention are repeated at several time-points, e.g. at one or more time-points prior to, during, and/or after treatment, development, and/or amelioration of erythema.

In particular, the light reflectance of a skin or mucosal area of a subject is measured at one or more time-points prior to, during, and/or after development or progression of erythema, or prior to, during, and/or after amelioration or regression of erythema, or prior to, during, and/or after the period of administration of the pharmaceutical or cosmetic preparation, or prior to, during, and/or after the period of treatment (e.g. a local treatment of the skin or mucosal area, or a systemic treatment of the subject). The gradient between two or more of said erythema values may be determined, e.g. between two or more subsequent measurements or erythema values, or between two or more measurements or erythema values over treatment or observation time. Accordingly, the erythema value calculated based on a measurement taken prior to any treatment (e.g. radiation) and/or manifestation of erythema may be the baseline erythema value. Any erythema value calculated based on a measurement taken during or after any treatment (e.g. radiation) and/or manifestation of erythema may be a follow-up erythema value.

The gradient between two or more erythema values may be determined, e.g. between two or more subsequent measurements or erythema values, or between two or more measurements or erythema values over treatment or observation time. An increase of the erythema value between two or more erythema values indicates progression of erythema. No significant change of the erythema value (or no gradient between two or more erythema values) indicates a stable skin or mucosal condition. A decrease of the erythema value between two or more erythema values indicates regression of erythema.

In an embodiment, the erythema is caused by irradiation and may be selected from the group consisting of radiation induced dermatitis (also called radiation dermatitis, or radio-dermatitis) and sunburn.

In one embodiment, the erythema is caused by chemotherapy with cytotoxic drugs, such as e.g. fluorouracil, capecitabine, cytarabine, sorafenib, or pegylated liposomal doxorubicin (Doxil), or tyrosine kinase inhibitors (e.g. sorafenib and sunitinib). Such erythema may also be called palmar-plantar erythrodysesthesia or hand-foot syndrome.

In an embodiment, the erythema is caused by drug intake, such as e.g. antibiotics (sulfonamides, penicillins, cefixime), barbituates, lamotrigine, phenytoin (e.g., Dilantin), non-steroidal anti-inflammatory drugs (NSAIDs); or EGFR inhibitors, for example, anti-EGFR antibody therapy, especially the administration of cetuximab (Erbitux®).

In an embodiment, the erythema is caused by allergen exposure, such as e.g. various allergens for allergy testing, urushiol (a resin produced by poison ivy and poison oak), penicillin, latex, or wasp, fire ant and bee stings.

In an embodiment, the erythema is caused by fungal infection, such as e.g. tinea (ringworm), or candida.

In an embodiment, the erythema is caused by bacterial infection, e.g. with staphylococcus, streptococcus, or by a treponemal disease, such as e.g. syphilis, bejel, pinta and yaws.

In an embodiment, the erythema is caused by viral infection, and may be selected from the group consisting of shingles, rubella, herpes, hand-foot-mouth disease, enterovirus infection, chickenpox infection, or infection by erythrovirus (erythema infectiosum or fifth disease).

In an embodiment, the erythema is caused by a skin disease, which may be selected from the group consisting of psoriasis, atopic eczema or atopic dermatitis (neurodermatitis), eczema, or acne.

In an embodiment, the erythema is caused by a disease affecting internal or external mucosa, e.g. oral, nasal, or intestinal mucosa, and may be selected from the group consisting of inflammatory bowel disease, Morbus Crohn (or Crohn's disease), aphthous stomatitis, conjunctivitis, chronic obstructive pulmonary disease, peptic ulcers, alcohol abuse, and gastritis.

In an embodiment, the erythema is caused by a somatoform disorder, such as blushing.

All embodiments, examples, definitions and description of the methods for assessing erythema as specified above also apply to this aspect of the invention.

As described above, for a subjective assessment of erythema, e.g. radiodermatitis, validated assessment tools are available, such as the classification system "Common Terminology Criteria for Adverse Effects" (CTCAE, e.g. CTCAE version 4.03), which has been developed by the Radiation Therapy Oncology Group (RTOG) and the National Cancer Institute (NCI).

According to said CTCAE grading, grade 1 radiodermatitis include faint erythema or dry desquamation, which may be accompanied by pruritus, skin distension, hair loss, and pigment alteration. These skin irritations normally occur a couple of days or up to a couple of weeks after the beginning of radiation treatment. Grade 2 radiodermatitis skin irritations include moderate to brisk erythema or a patchy moist desquamation, mostly confined to skin folds and creases, and a moderate edema. These skin irritations are often painful and bear an increased risk of infection (Hymes, Strom, & Fife, 2006). In grade 3 radiodermatitis according to said CTCAE grading the area of moist desquamation spreads to areas outside of the skin folds. Haemorrhage from minor trauma and abrasion are often present. Grade 4 radiodermatitis is a life-threatening condition characterized by skin necrosis and ulceration of full thickness dermis. There is a particularly high risk of spontaneous bleeding. These changes are very painful and are characterized by poor healing. Skin grafts may be needed. Grade 5 radiodermatitis according to said CTCAE grading leads to the death of the patient.

In one embodiment, the erythema is a radiation dermatitis of grade 0, 1, 2, 3, or 4. In one embodiment, the erythema is a radiation dermatitis of grade 0 or higher, 1 or higher, 2 or higher, 3 or higher, or 4 or higher. In one embodiment, the erythema is a radiation dermatitis according to grade 0 to 1. In one embodiment, the erythema is a radiation dermatitis according to grade 0 to 2. In one embodiment, the erythema is a radiation dermatitis according to grade 0 to 3. In one embodiment, the erythema is a radiation dermatitis according to grade 0 to 4.

In one embodiment, the subject is a human. In one embodiment, the subject is a non-human animal. The non-human animal may be a mammal selected from the group consisting of primates (non-human primates), pigs, rodents, or rabbits. On an embodiment, the subject is a cancer patient who is or will be treated with radiation. In one embodiment, the subject is a breast cancer patient, who is or will be treated with radiation. The breast cancer patient may have undergone surgery, e.g. breast-preserving surgery. In one embodiment, the subject is a head and neck cancer (HNC) patient who is or will be treated with radiation. The HNC patient may have undergone surgery. The subjects may also be treated with a chemotherapy.

In one embodiment, the erythema value is calculated based on a measurement or image obtained prior to and/or at the beginning of irradiation. In said embodiment, the erythema value is a baseline erythema value (i.e. the initial or reference erythema value). Irradiation may be treatment with or exposure to x-ray, UV irradiation, and/or solar irradiation. In one embodiment, the erythema caused by irradiation is dermatitis radiation grade 2 or higher according to the CTCAE as described above. In one embodiment, erythema caused by irradiation is characterized by epitheliolysis, desquamation, and/or rash. In one embodiment, erythema caused by irradiation is characterized by initial or minor epitheliolysis, desquamation, and/or rash.

The calculation of the erythema value prior to or at the beginning of irradiation (baseline erythema value, or initial erythema value), as well as the gradient between the erythema values measured during the initial phase of irradiation according to the present invention allows to predict the risk to develop erythema, the intensity of erythema, and/or the time to occurrence of erythema. Thus, the erythema value provides a prognostic factor in radiation therapy and may be used to assess and/or adapt the dose and/or duration of radiation. Furthermore, the baseline erythema value and/or any follow-up erythema values may be used to assess and/or adapt the dose and/or duration of a treatment and/or prophylaxis, such as the treatment and/or prophylaxis of one or more adverse events of radiation or adverse drug reactions of a treatment. With said methods, it is possible to provide a prognosis of the expected severity of radiation dermatitis, as well as the time until a prophylaxis and/or treatment has to be given.

As can be seen in the examples of the present invention, the baseline erythema value strongly correlates to the grade as well as to the duration until radiation dermatitis of a certain grade (e.g. grade 2) is developed.

Accordingly, the methods of the invention may be used to objectively predict and assess the grade of erythema, the time to occurrence of a certain grade of erythema, as well as the individual risk of a subject to develop a certain grade of erythema.

In contrast to the erythema value, the Fitzpatrick Scale (Table 2) did not correlate with the developed grade of radiation dermatitis in the studies underlying the present invention. The Fitzpatrick Scale (also called Fitzpatrick skin typing test or Fitzpatrick phototyping scale) is a numerical classification schema for the color of skin. It was developed in 1975 by Thomas B. Fitzpatrick, a Harvard dermatologist, as a way to classify the response of different types of skin to UV light. It remains a recognized tool for dermatologic research into the color of skin. It measures several components: genetic disposition, reaction to sun exposure and tanning habits.

TABLE 2

Fitzpatrick Skin Color Scale

The Fitzpatrick Scale:
Type I (scores 0-7) Light, pale white. Always burns, never tans.
Type II (scores 8-16) White; fair. Usually burns, tans with difficulty
Type III (scores 17-24) Medium, white to olive. Sometimes mild burn, gradually tans to olive.
Type IV (scores 25-30) Olive, moderate brown. Rarely burns, tans with ease to a moderate brown.
Type V (scores over 30) Brown, dark brown. Very rarely burns, tans very easily.
Type VI Black, very dark brown to black. Never burns, tans very easily, deeply pigmented.

In an embodiment, the methods of the present invention may be used independently of the skin type, and even independent from basic skin color. For example, erythema or skin color may be assessed in subjects with similar and/or different basic skin colors. For comparison of subjects with different skin colors (e.g. of different races), reference erythema values or reference gradients between two or more erythema values of reference areas or reference subjects may be generated and the measured erythema values may be compared to said references.

Moreover, with the methods of the invention, it is possible to assess erythema or skin irritations that are characterized by colors other than red or in addition to red, especially white or black. For example, psoriasis is often characterized by white or silver scale with underlying erythema. In another example, erythema may also be characterized by very dark skin irritations, especially if necrosis of keratinocytes occurs, such as e.g. in Stevens-Johnson syndrome or toxic epidermal necrolysis (TEN, also known as "Lyell's syndrome"). Furthermore, the methods of the present invention can be used to document and/or assess wounds and wound healing. In general, the methods of the present invention allow an assessment of skin or mucosal color (or erythema) changes between two or more measurements.

A description of radiotherapy in breast cancer, skin reactions caused by radiotherapy, the visual assessment of erythema by the above referenced CTCAE grading, spectrophotometric methods and analysis can be found e.g. in Haigis 2005 (Kristine Haigis, Inaugural-Dissertation zur Erlangung des medizinschen Doktorgrades der Medizinischen Fakultät der Albert-Ludwigs-Universität Freiburg im Breisgau).

In another aspect, the invention provides a software tool for erythema monitoring and analysis by using the methods according to the invention. A software tool is used computer-based. Thus the inventive method is generally computer-implemented. Accordingly, the above described methods according to the present invention may be integrated into a software platform that runs on a computer or computer-like device. Said software platform may be web based (or cloud based), and may include tools for image generation and data input (e.g. mobile imaging and/or computer imaging, patient identification and/or patient information), data management and data output (e.g. databases and/or statistics), as well as data security (e.g. encryption). For example, mobile devices such as smartphones, tablets, i-phones, i-Pads etc. may be used for the methods of the present invention.

The software tool according to the invention may be a mobile application or in another embodiment may integrate into the software platform of a stationary device (e.g. a radiation machine). At any point during the method of the invention, method-relevant data may be transmitted over computer-based networks such as the internet or local area networks or wireless networks, and the method may be continued at a another physical location or locations, such as a web-based or cloud-based server or computer.

Examples of medical software tools for the documentation and analysis of clinical data are, for example, the Secure Platform for Integrating Clinical Services (SPICS) systems provided by the company RISE (Research Industrial Systems Engineering GmbH), developed by RISE and the Technical University Vienna, e.g. the SPICS SOUL (http://soul-doc.com/) and SPICS VASC (http://vasc-world.com/), as well as the SPICS based W.H.A.T system (referenced above). The software tools of the prior art, especially the W.H.A.T system, as well as the methods for assessing erythema described in the prior art may be improved by using the methods of the present invention, in particular, the calculation of the erythema value or the methodically derived yellowness value.

In addition to the methods of the present invention, subjective assessment of erythema may be done. Accordingly, the grade of erythema may be clinically assessed by a physician, e.g. according to the CTCAE. The erythema value calculated with the methods of the invention may be compared to the subjectively assessed erythema grade.

The methods according to the invention, especially the calculation of the erythema value, can be used to assess erythema caused by a treatment or disease, to assess the efficacy of a treatment that may ameliorate erythema, and/or to assess the opacity of a cosmetic preparation. For example, the methods of the invention may be used for demonstrating the efficacy of a pharmaceutical and/or cosmetic product. Said pharmaceutical product may be intended for the prevention and/or amelioration of erythema. Said cosmetic product may be a non-therapeutic product, e.g. for prevention or amelioration of the appearance of erythema, and/or for covering erythema. Furthermore, the methods of the present invention may be used to identify a subject as prone to erythema caused by irradiation. The methods of the present invention allow an improvement in erythema management in daily care. Moreover, the calculation of the erythema value, especially the baseline erythema value (i.e. the initial erythema value prior to any treatment, or reference erythema value), may be used for selecting and/or deselecting subjects, e.g. for a treatment, a prophylaxis, or for participation in a clinical trial. For example, the baseline erythema value, as well as any follow-up erythema values, or the gradient between two or more of such erythema values, may be used in the planning and conduction of clinical trials, e.g. as prospective screening parameter to impede dilution of study data by patients at a lower risk of developing radiodermatitis. Moreover, the erythema value may be used to generate standard erythemal curves, standard erythema doses, and/or erythema reference action spectra, e.g. according to the ISO 17166 CIE S 007/E.

In addition, the methods of the present invention may be used to assess erythema, e.g. skin toxicities, in an animal model, e.g. in research and pre-clinical development of a pharmaceutical preparation, or in the development of a cosmetic preparation. For example, the methods according to the invention may be used in an acute dose toxicity study and/or in a repeated dose toxicity study. The methods of the invention may also be used to measure the skin irritation potential of a pharmaceutical or cosmetic preparation.

Furthermore, the baseline erythema value or one or more erythema values calculated based on measurements during the initial phase of irradiation treatment (e.g. during the first week of radiation therapy with one radiation fraction per day), or the gradient between such two or more erythema values may be used to prospectively assess the risk to develop radiation dermatitis, the time until development of radiation dermatitis, and/or the expected severity of radiation dermatitis, as well as the time until a prophylactic intervention has to be taken.

With the methods of the present invention, it is possible to re-analyse any data obtained from the measurements, since measurements or images may be analyzed several times, with several methods, and/or at any point in time.

Still another application of the methods of the present invention is the analysis of meat. Since meat is characterized by different shades of red color, as well as white and dark colors, the methods of the invention, especially the calculation of the redness value according to the formula of the invention, can be used to identify the animal species from which the meat originates, the part of the animal from which the meat origins, the degree of freshness of the meat, as well as its fat content.

The present invention also relates to a computational method for objective assessment and remote monitoring of erythema by using a mobile application software integrated in a software platform of a mobile device further enabling to automate the allocation between a measurement of an area of a subject and obtained erythema value to such subject. The invented method also provides a novel timesaving and cost efficient technology capable of being linked with any electronic clinical monitoring and service system.

In particular, the invention also relates to a method for assessing erythema of a subject comprising the steps of using a software application integrated into a software platform of a mobile device for measuring the light reflectance of a skin or mucosal area of the subject, obtaining the L* value and the a* value of said measurement according to the L*a*b* color space, and calculating the erythema value according to the formula $(L^*_{max}-L^*) \times a^*$. Furthermore, the invention relates to a method for assessing the risk of a subject to develop erythema caused by irradiation by calculating the erythema value according to the invention; an according method for predicting the intensity of erythema that a subject develops due to irradiation; an according method for predicting the time until a subject develops erythema caused by irradiation; an according method for analyzing a pharmaceutical or cosmetic preparation or an allergen for its ability to cause erythema in a subject; and to an according method for analyzing a pharmaceutical or cosmetic preparation for its ability to ameliorate the appearance of erythema in a subject. The invention relates further to methods for analyzing skin color of a subject, for documenting or analyzing wounds or wound healing of a subject, for documenting hematoma grading and hematoma development of a subject and for documentation and objective assessment of moles or lentigine or freckles of a subject, based on the formula $(L^*_{max}-L^*) \times a^*$. In another aspect, the invention relates to the method of analyzing meat based on the formula $(L^*_{max}-L^*) \times a^*$. In another embodiment, the invention refers to an equivalently derived method for calculating the yellowness of a subject comprising the steps of using a software application integrated into a software platform of a mobile device, for measuring the light reflectance of a skin or mucosal or conjunctive area of the subject, obtaining the L* value and the b* value of said measurement according to the L*a*b color space, and calculating the yellowness value according to the formula $(L^*_{max}-L^*) \times b^*$; an according method combined with the erythema value can be used for documenting and analyzing icterus or cyanosis of a subject.

The present invention also provides computational methods for analyzing and monitoring erythema and any other skin color comprising the usage of a mobile application software integrated in a software platform of a mobile device, measuring the light reflectance of a skin or mucosal area, analyzing said measurement and applying a novel formula to calculate the erythema value. The skin redness or erythema value provides an objective, continuous measure for skin redness or erythema over the entire range of intensities. Accordingly, the higher the skin redness erythema value the higher is the intensity of erythema. Further detection of a quick response or a barcode code the developed method allows to automatize the allocation process between a subject and the obtained color values of such a subject. The invented computational method consequently delivers a novel timesaving and cost efficient technology capable of being linked with any electronic clinical monitoring and service system.

In another aspect, the invention relates to a method wherein the software application integrated into a software platform of a mobile device is used for analyzing a pharmaceutical or cosmetic preparation or an allergen for its ability to cause erythema. In another aspect, the invention relates to a method wherein the software application integrated into a software platform of a mobile device is used for analyzing a pharmaceutical or cosmetic preparation for its ability to ameliorate the appearance of erythema.

In another embodiment, the light reflectance of a skin or mucosal area of said subject is measured at least once prior therapeutic use of a pharmaceutical or topical use of a cosmetic preparation, and at one or more time-points during the therapeutic use of a pharmaceutical or topical use of a cosmetic, and the erythema values are calculated for each measurement. The term "therapeutic use of said pharmaceutical or topical use of cosmetic preparation" with regard to said aspects refers to one or more time-points within and/or after the period of therapeutic use of the pharmaceutical or topical use of a cosmetic preparation. For example, the light reflectance of a skin or mucosal area of the subject is measured at one or more time-points after single or repeated therapeutic use of the pharmaceutical or topical use of a cosmetic preparation. The light reflectance of a skin or mucosal area of the subject may also be measured at one or more time-points after the period therapeutic use of the pharmaceutical or topical use of the cosmetic preparation, i.e. when the pharmaceutical or cosmetic preparation is no longer applied. The gradient between two or more of said erythema values may be determined, e.g. between two or more subsequent measurements or erythema values, or between two or more measurements or erythema values over treatment or observation time. An increase of the erythema value between two or more erythema values over application time indicates progression of erythema, i.e. that the pharmaceutical or cosmetic preparation causes erythema, or is not effective in preventing erythema. No significant change of the erythema value between two or more erythema values over application time indicates a stable skin or mucosal condition, i.e. that the pharmaceutical or cosmetic preparation does not cause erythema, is effective in preventing erythema, is not effective in treating erythema, or is not effective in ameliorating the appearance of erythema. A decrease of the erythema value between two or more erythema values over application time indicates regression of erythema, i.e. that the pharmaceutical or cosmetic preparation is effective in treating erythema, or in ameliorating the appearance of erythema.

In another embodiment of the sixth aspect, the opacity of a cosmetic product is analyzed. The cosmetic product may be make-up, a foundation, face powder, camouflage, a cover stick, or a concealer. A decrease of the erythema value after topical use the product indicates that the cosmetic product is effective in covering erythema.

The present invention also relates to a computational method comprising the use of a software application integrating into a software platform of a mobile device, implying that the measurement or image can be obtained by any suitable mobile measurement method or imaging method, such as e.g. spectrophotometry, video, video frame buffer, and/or digital photography.

In a preferred embodiment of the present invention the measurement is obtained by using a software application integrating into the software platform of a smartphone (e.g. iPhone 4, iPhone 4S, iPhone 5 or higher) or into a tablet computer (e.g. iPad, iPad Air, iPad Retina or higher)

In an advantageous embodiment the measurement may be obtained by using a software application integrating into a software platform of a smartphone with Kinect-like 3D imaging sensors or a wearable computer with an optical head-mounted display (e.g. google glasses).

The measurement or image may also be obtained by integrating the used software application into the software platform of endoscopic imaging devices. Thus in one embodiment, the measured skin or mucosal area is an internal mucosal area and the light reflectance is measured by endoscopic methods. For example, the methods according to the present invention may be used to diagnose and monitor diseases affecting internal mucosa and their treatment, such as e.g. Morbus Crohn.

In a preferred embodiment of the invention the method further includes a computational step wherein the software application integrated in a mobile software platform automatically detects a barcode or a quick response code or a near field tag allowing automated allocation of a subject ID and the obtained color values of an analyzed area of this subject.

In another embodiment, the erythema value may be converted into a relative value compared to the respective maximal value, which is set to 100%, in order to compare several erythema values based on different measurement methods or imaging methods, and/or based on different color depths. In a preferred embodiment of the invention, a calculated reddening value (positive a*) is normalized based on the maximal values for L* and a* according to the formula $(L^*_{max}-L^*) \times a^*/(a^*_{max} \times L^*_{max})$.

In another embodiment a furthermore calculated yellowness value (positive b*) is normalized based on the maximal values for L* and b* according to the formula $(L^*_{max}-L^*) \times b^*/(b^*_{max} \times L^*_{max})$ and in a more advantageous embodiment a furthermore calculated blueness value (negative b*) is normalized based on the maximum value for L* and the minimum value for b* according to the formula $(L^*_{max}-L^*) \times b^*/(b^*_{min} \times L^*_{max})$.

In case of measured negative a* (green) values a similar technique can be derived according to the formula $(L^*_{max}-L^*) \times b^*/(b^*_{min} \times L^*_{max})$. The provided set of normalization methods may be used for time dependent analysis of erythema in context to any other observed skin color seen during development and therapy of icterus or hematoma or cyanosis of a subject.

As described earlier, the invention also relates in particular to a computational method which uses a mobile software application integrated in a software platform of a mobile device for erythema assessment and monitoring which applies the derived methods according to the invention. Accordingly, in this context is must be furthermore considered that any of the above described methods according to the present invention may be integrated into a online or cloud based software platform e.g. into a software suite. Said software app, in a preferred embodiment of the invention integrates into a software platform of a mobile device which directly links to a web based (or cloud based) image analysis and monitoring platform further allowing remote erythema assessment and monitoring of a measured area of a subject, and in one embodiment such software app has further access or may include tools for image generation and data input (e.g. mobile imaging and/or computer imaging, automated patient identification and/or allocation of patient information), data management and data output (e.g. databases and/or statistics), as well as data security (e.g. encryption). For example, mobile devices such as smartphones, computer tablets, i-phones (e.g. iPhone 4, iPhone 4S, iPhone 5 or higher), i-Pads (e.g. (e.g. iPad, iPad Air, iPad Retina or higher) etc. may be used for the methods of the present invention.

In an advantageous embodiment the measurement may be obtained by using a software application integrating into a software platform of a smartphone with Kinect-like 3D imaging sensors or a wearable computer with an optical head-mounted display (e.g. google glasses).

While the above embodiments have been disclosed as the best mode presently contemplated by the inventor it has to be noticed, that any of the above described methods connected with the analysis of the erythema value may be combined with a therefrom directly derived computational method applicable for analyzing the yellowness value of the skin or mucosa or conjunctiva of a subject, e.g. for objective and time resolved quantitative analysis of icterus grading and development of an skin or. Due to this reason the given examples should not be interpreted as limiting and a equivalently derived method may be used for analysis of blueness values or greenness values e.g. for time resolved analysis of cyanosis or hematoma of a skin or mucosa or conjunctive area of a subject.

The present invention is further exemplified by the following embodiments:

1. A method for assessing erythema of a subject comprising the steps of
    measuring the light reflectance of a skin or mucosal area of the subject,
    obtaining the L* value and the a* value of said measurement according to the L*a*b* color space, and
    calculating the erythema value according to the formula $$(L^*_{max}-L^*) \times a^*.$$

2. A method for assessing the risk of a subject to develop erythema caused by irradiation comprising the steps of
    measuring the light reflectance of a skin or mucosal area of the subject prior to irradiation,
    obtaining the L* value and the a* value of said measurement according to the L*a*b* color space,
    calculating the baseline erythema value according to the formula $$(L^*_{max}-L^*) \times a^*, \text{ and}$$

correlating the baseline erythema value to the risk of the subject to develop erythema caused by irradiation.

3. A method for predicting the intensity of erythema that a subject develops due to irradiation comprising the steps of measuring the light reflectance of a skin or mucosal area of the subject prior to irradiation, obtaining the L* value and the a* value of said measurement according to the L*a*b* color space, and calculating the baseline erythema value according to the formula $$(L^*_{max}-L^*) \times a^*, \text{ and}$$

correlating the baseline erythema value to the intensity of erythema that the subject develops due to irradiation.

4. A method for predicting the time until a subject develops erythema caused by irradiation comprising the steps of measuring the light reflectance of a skin or mucosal area of the subject prior to irradiation, obtaining the L* value and the a* value of said measurement according to the L*a*b* color space, calculating the baseline erythema value according to the formula $$(L^*_{max}-L^*) \times a^*, \text{ and}$$

inversely correlating the baseline erythema value to the time until the subject develops erythema caused by irradiation.

5. A method for testing a pharmaceutical or cosmetic preparation for its ability to cause or treat erythema in a subject comprising the steps of measuring the light reflectance of a skin or mucosal area of the subject prior to and following the administration of the pharmaceutical or cosmetic preparation, obtaining the L* value and the a* value of each measurement according to the L*a*b* color space, and calculating the erythema value for each measurement according to the formula $$(L^*_{max}-L^*) \times a^*.$$

6. A method for testing a pharmaceutical or cosmetic preparation for its ability to ameliorate the appearance of erythema of a subject comprising the steps of measuring the light reflectance of a skin area of the subject prior to and following the administration of the pharmaceutical or cosmetic preparation, obtaining the L* value and the a* value of each measurement according to the L*a*b* color space, and calculating the erythema value for each measurement according to the formula $$(L^*_{max}-L^*) \times a^*.$$

7. A method for analyzing skin color of a subject comprising the steps of measuring the light reflectance of a skin or mucosal area of the subject, obtaining the L* value and the a* value of said measurement according to the L*a*b* color space, and calculating the skin redness value according to the formula $$(L^*_{max}-L^*) \times a^*.$$

8. A method for documenting or analyzing wounds or wound healing of a subject comprising the steps of measuring the light reflectance of a skin or mucosal area of the subject, obtaining the L* value and the a* value of said measurement according to the L*a*b* color space, and calculating the erythema value according to the formula $$(L^*_{max}-L^*) \times a^*.$$

9. A computer-based method for assessing erythema of a subject comprising the steps of obtaining the measured light reflectance of a skin or mucosal or conjunctive area of the subject; and obtaining the L* value and the a* value of said measurement according to the L*a*b* color space; and calculating the erythema value according to the formula $$(L^*_{max}-L^*) \times a^*.$$

10. A computer-based method for analyzing skin color of a subject comprising obtaining the measured light reflectance of a skin or mucosal or conjunctive area of the subject; and obtaining the L* value and the a* value of said measurement according to the L*a*b* color space; and calculating the redness value according to the formula $$(L^*_{max}-L^*) \times a^*; \text{ and}$$

obtaining the L* value and the b* value of said measurement according to the L*a*b color space; and calculating the yellowness value according to the formula $$(L^*_{max}-L^*) \times b^*.$$

11. A computer-based method for assessing erythema of a subject comprising the steps of measuring the light reflectance of a skin or mucosal or conjunctive area of the subject;

obtaining the L* value and the a* value of said measurement according to the L*a*b* color space; and calculating the erythema value according to the formula $$(L^*_{max}-L^*) \times a^*.$$

12. A computer-based method for analyzing skin color of a subject comprising obtaining the measured light reflectance of a skin or mucosal or conjunctive area of the subject; and obtaining the L* value and the a* value of said measurement according to the L*a*b* color space; and calculating the redness value according to the formula $$(L^*_{max}-L^*) \times a^*; \text{ and}$$

obtaining the L* value and the b* value of said measurement according to the L*a*b color space; and calculating the yellowness value according to the formula $$(L^*_{max}-L^*) \times b^*.$$

13. The method of any of the preceding embodiments, wherein the erythema value is correlated to the intensity of erythema.

14. The method of any of the preceding embodiments, wherein the light reflectance is measured at two or more time-points and the erythema values are calculated for each measurement.

15. The method of embodiment 14, wherein the gradient between two or more erythema values is correlated to the development of erythema.

16. The method of embodiment 15, wherein an increase between two or more erythema values indicates progression of erythema.

17. The method of embodiment 14, wherein a decrease between two or more erythema values indicates regression of erythema.

18. The method of embodiment 14, wherein no gradient between two or more erythema values indicates stable skin or mucosal condition.
19. The method of any of the preceding embodiments, wherein the light reflectance is measured in the L*a*b* color space and the L* value and the a* value are obtained directly from said measurement.
20. The method of any of the preceding embodiments, wherein the light reflectance is measured in a color space other than the L*a*b* color space, and the L* value and the a* value according to the L*a*b* color space are obtained by converting the light reflectance values of said measurement into the corresponding values of the L*a*b* color space.
21. The method of any of the preceding embodiments, wherein the skin or mucosal area is a gross area comprising one or more segment areas, and wherein the erythema value is calculated for each segment area.
22. The method of embodiment 21, wherein the segment area is an erythema area, a treatment area, and/or a reference area.
23. The method of any of the preceding embodiments, wherein the erythema value is compared to a reference erythema value.
24. The method of any of the preceding embodiments, wherein the light reflectance of said area is measured by a single spot measurement from which one single L* value and one single a* value are obtained, and the erythema value is calculated based on said single spot values.
25. The method of any of the preceding embodiments, wherein the light reflectance of a skin or mucosal area of a subject is measured by spectrophotometry.
26. The method of any of the preceding embodiments, wherein the light reflectance of a skin or mucosal area of a subject is measured by obtaining an image of said skin or mucosal area.
27. The method of embodiment 26, wherein the L* value and the a* value of a single pixel of the image are obtained, and the erythema value is calculated for said single pixel.
28. The method of embodiment 26 or 27, wherein the L* value and the a* value of each pixel of the skin or mucosal area are obtained, and the erythema value is calculated for each pixel of the skin or mucosal area.
29. The method of any of embodiments 26 to 28, wherein the image is obtained by digital photography.
30. The method of any of embodiments 26 to 29, wherein a mean erythema value is calculated based on single pixel erythema values.
31. The method of any of embodiments 26 to 30, wherein a mean erythema value is calculated for each segment area.
32. The method of any of embodiments 26 to 31, wherein the light reflectance of the skin or mucosal area is measured with a color depth of 8, 12, 15 or 16 bit per channel.
33. The method of any of the preceding embodiments, wherein the skin or mucosal area is an internal mucosal area, and the light reflectance is measured by endoscopic methods.
34. The method of any of the preceding embodiments, wherein the subject is a human, a non-human primate, a pig, a rodent, or a rabbit.
35. The method of any of the preceding embodiments, wherein the subject
is prone to erythema,
is or will be treated with a treatment that may cause erythema,
is or will be treated with a treatment that prevents erythema,
is suffering from erythema,
is or will be treated with a treatment that may treat erythema, or
is or will be treated with a treatment that ameliorates the appearance of erythema.
36. The method of embodiment 34 or 35, wherein the subject is a cancer patient who is or will be treated with radiation.
37. The method of embodiment 36, wherein the subject is a breast cancer or head and neck cancer patient.
38. The method of any of embodiments 1 to 12, wherein the light reflectance is measured prior to irradiation and at one or more time-points following irradiation, wherein the gradient between two or more erythema values is calculated, and wherein said gradient is correlated to the risk of a subject to develop erythema caused by irradiation, or to the intensity of erythema that the subject develops due to irradiation, or inversely correlated to the time until the subject develops erythema caused by irradiation.
39. The method of embodiment 38, wherein the risk of a subject to develop erythema caused by irradiation, the intensity of erythema that the subject develops due to irradiation, or the time until the subject develops erythema caused by irradiation is assessed or predicted based on the baseline erythema value and on the gradient between two or more erythema values.
40. The method of embodiment 1 to 12, wherein the opacity of a cosmetic product is tested.
41. A method for analyzing meat comprising the steps of
measuring the light reflectance of an area of the meat or the entire meat slice,
obtaining the L* value and the a* value of said measurement according to the L*a*b* color space, and
calculating the redness value according to the formula $$(L^*_{max}-L^*) \times a^*.$$

42. The method of any previous embodiment, wherein the method is conducted by using a mobile device.
43. A computer-based method for assessing erythema of a subject comprising the steps of
measuring the light reflectance of a skin or mucosal or conjunctive area of the subject;
obtaining the L* value and the a* value of said measurement according to the L*a*b* color space; and
calculating the erythema value according to the formula $$(L^*_{max}-L^*) \times a^*.$$

44. The method of any previous embodiment for assessing the risk of a subject to develop erythema caused by irradiation comprising the steps of
measuring the light reflectance of a skin or mucosal area of the subject prior to irradiation,
obtaining the L* value and the a* value of said measurement according to the L*a*b* color space,
calculating the baseline erythema value according to the formula $$(L^*_{max}-L^*) \times a^*, \text{ and}$$

correlating the baseline erythema value to the risk of the subject to develop erythema caused by irradiation.

45. The method of any previous embodiment for predicting the intensity of erythema that a subject develops due to irradiation comprising the steps of
measuring the light reflectance of a skin or mucosal area of the subject prior to irradiation,
obtaining the L* value and the a* value of said measurement according to the L*a*b* color space, and
calculating the baseline erythema value according to the formula $$(L^*_{max}-L^*) \times a^*, \text{ and}$$

correlating the baseline erythema value to the intensity of erythema that the subject develops due to irradiation.

46. The method of any previous embodiment for predicting the time until a subject develops erythema caused by irradiation comprising the steps of
measuring the light reflectance of a skin or mucosal area of the subject prior to irradiation,
obtaining the L* value and the a* value of said measurement according to the L*a*b* color space,
calculating the baseline erythema value according to the formula $$(L^*_{max}-L^*) \times a^*, \text{ and}$$

inversely correlating the baseline erythema value to the time until the subject develops erythema caused by irradiation.

47. The method of any previous embodiment for use in analyzing a pharmaceutical or cosmetic preparation or an allergen for its ability to cause erythema.

48. The method of any previous embodiment for use in analyzing a pharmaceutical or cosmetic preparation for its ability to ameliorate the appearance of erythema.

49. A computer-based method for analyzing skin color of a subject comprising
measuring the light reflectance of a skin or mucosal or conjunctive area of the subject; and
obtaining the L* value and the a* value of said measurement according to the L*a*b* color space; and
calculating the redness value according to the formula $$(L^*_{max}-L^*) \times a^*; \text{ and}$$

obtaining the L* value and the b* value of said measurement according to the L*a*b color space; and
calculating the yellowness value according to the formula $$(L^*_{max}-L^*) \times b^*.$$

50. The method of any previous embodiment for use in documenting or analyzing wounds or wound healing of a subject.

51. The method of any of the preceding embodiments wherein the erythema value is correlated to the intensity of erythema and/or the gradient between two or more erythema values is correlated to the development of erythema.

52. The method of any of the preceding embodiments wherein an increase between two or more erythema values indicates progression of erythema, wherein a decrease between two or more erythema values indicates regression of erythema, and/or wherein no gradient between two or more erythema values indicates stable skin or mucosal condition.

53. The method of any of the preceding embodiments, wherein the light reflectance is measured in a color space other than the L*a*b* color space, and the L* value and the a* value and the b* value according to the L*a*b* color space are obtained by converting the light reflectance values of said measurement into the corresponding values of the L*a*b* color space.

54. The method of any of the preceding embodiments, wherein the erythema value is compared to a reference erythema value.

55. The method of any of the preceding embodiments, wherein the light reflectance of a skin or mucosal area of a subject is measured by obtaining an image of said area.

56. The method of any of the preceding embodiments for analyzing meat comprising the steps of
measuring the light reflectance of an area of the meat or the entire meat slice,
obtaining the L* value and the a* value of said measurement according to the L*a*b* color space, and
calculating the redness value according to the formula $$(L^*_{max}-L^*) \times a^*.$$

57. The method of any of the preceding embodiments for use in analyzing lentigo solaris or lentigo simplex or lentigo maligna or lentigo aestiva of a subject.

58. The method of any of the preceding embodiments wherein an equivalent technique is applied for calculating the yellowness value and any other reference yellowness value comprising the steps of
measuring the light reflectance of a skin or mucosal or conjunctive area of the subject, using a mobile device; and
obtaining the L* value and the b* value of said measurement according to the L*a*b color space; and
calculating the yellowness value according to the formula $$(L^*_{max}-L^*) \times b^*.$$

59. The method of any of the preceding embodiments for use in documenting and analyzing hematoma grading and hematoma development of the skin or mucosa or conjunctiva of a subject over time.

60. The method of any of the preceding embodiments for use in documenting and analyzing icterus grading and icterus development of the skin or mucosa or conjunctiva of a subject over time.

61. The method of any of the preceding embodiments for use in documenting and analyzing the degree of cyanosis and cyanosis development of the skin or mucosa of a subject over time.

62. The method of any preceding embodiment wherein the mobile device is linked to a clinical service system.

63. The method of any preceding embodiment wherein the mobile device is a tablet or smartphone.

64. The method of any preceding embodiment wherein the mobile device is a wearable computer with an optical head-mounted display.

65. The method of any preceding embodiment wherein the mobile device is linked to a cancer irradiation machine.

66. The method of any of the preceding embodiments wherein the L* and a* value of each pixel of the image is obtained and the redness value for each pixel of the image is calculated.

67. The method of any of the preceding embodiments wherein the L* and b* value of each pixel of the image is obtained and the yellowness value for each pixel of the image is calculated.

68. The method of any of the preceding embodiments wherein a mean color value based on single pixel values is calculated.
69. The method of any of the preceding embodiments wherein a mean color value for each measured segment area is calculated.
70. The method of any of the preceding embodiments wherein the measured area is a gross area comprising one or more segment areas and wherein any of the calculated values is calculated for each segment area.
71. The method of any of the preceding embodiments further comprising the simultaneous measurement of a normalization marker containing chromatic code elements for automated marker recognition and lightning correction of calculated color values.
72. The method of any of the preceding embodiments wherein the normalization marker is designed as sticker or adhesive plaster or poster.
73. The method of any of the preceding embodiments wherein the normalization of a measured erythema value is carried out according to the formula $(L^*_{max}-L^*) \times a^*/(a^*_{max} \times L^*_{max})$.

74. The method of any of the preceding embodiments wherein the normalization of a measured greenness value is carried out according to the formula $(L^*_{max}-L^*) \times a^*/(a^*_{min} \times L^*_{max})$.

75. The method of any of the preceding embodiments wherein normalization of a measured yellowness value is carried out according to the formula $(L^*_{max}-L^*) \times b^*/(b^*_{max} \times L^*_{max})$.

76. The method of any of the preceding embodiments wherein normalization of a measured blueness value is carried out according to the formula $(L^*_{max}-L^*) \times b^*/(b^*_{min} \times L^*_{max})$.

77. The method of any of the preceding embodiments further comprising the step of detecting a barcode or a quick response code or a near field tag of the subject to automatize the allocation process between a subject and the obtained color values of the subject
78. The method of any of the preceding embodiments for use in a clinical monitoring and medical service system.
79. The method of any of the preceding embodiments, wherein the measuring step(s) and/or the obtaining step(s) and/or the calculating step(s) or any combinations thereof, especially all steps, are performed using a mobile device, such as a cell phone or smart phone or tablet.
80. The method of any of the preceding embodiments, further comprising obtaining the measured light reflectance, preferably by transmission over a network.
81. The method of embodiment 38, wherein the light reflectance is not measured but obtained otherwise.
82. The method of any of the preceding embodiments, wherein the obtaining step(s) and/or the calculating step(s), especially all of said steps, are performed using web-based or cloud-based processes.

EXAMPLES

Example 1: Clinical Phase 1b Study Using the Methods of the Invention

A clinical phase Ib testing with liposomally formulated recombinant human superoxide dismutase (APN201) delivered positive results in all endpoints analyzed. The pilot study was conducted in a double blind, placebo-controlled fashion and included 20 female breast cancer patients that received radiation therapy (25-28 Rx-fractions; total dose 50.0 Gy-50.4 Gy) after breast-preserving surgery. In this study, daily topical application of APN201 (rhSOD; 1.6 mg/mL) could be proven to be safe and well tolerated with no serious or drug related adverse events reported. Furthermore APN201 showed first signs towards efficacy with regard to pain, intensity of erythema and time to occurrence of grade 2 dermatitis (epitheliolysis).

Patient Population 20 patients with histologically confirmed early-stage breast cancer, who underwent prior breast-conserving surgery, were included. Further eligibility requirements were: age 18 years or older, Karnofsky performance status≥80% and Bra cup size≥D. Patients were excluded if they had bilateral or inflammatory breast cancer, lymphangiosis carcinomatosa, medically significant dermatologic conditions affecting the irradiated area, if the use of other agents with the aim of preventing and/or treating radiation dermatitis was planned, if they took concomitant medications which might exacerbate radiation dermatitis, and if they had a history of previous breast radiation therapy. All patients received whole-breast irradiation using standard opposed medial and lateral tangent fields to a total dose of 50.0-50.4 Gy in 25-28 irradiation (Rx) fractions. 19 patients completed the study and were analyzed for signs of efficacy.

Treatment Plan and Clinical Evaluations

For daily topical drug application of APN201/Placebo a split body design was applied by dividing the irradiated region vertically into two symmetric areas. This was carried out in a double blind fashion, starting with fraction one until the end of whole-breast irradiation (Rx fraction 25-28). The gel was applied as a thin film on the breast≥10 minutes before the radiation therapy (1 mL/100 cm² of the radiation field size). Furthermore, each day after radiation therapy, both parts of the irradiation area were consecutively covered with Bepanthen® moisturizing foam spray. Radiation dermatitis was assessed daily, based on the CTCAE v4.03 classification system beginning at baseline before the start of radiotherapy. In order to explore if the objective measurement reflects the clinical assessments of radiodermatitis, both spectrophotometric measurements and digital images of the treatment fields were taken initially at screening and daily from fraction 6 to fraction 25 or 28. The spectrophotometric measurements and digital images were taken on said days prior to the application of the study medication. Digital photographs were taken with the Canon Digital Cam Canon Powershot G12 under stable light conditions and standardized device settings. A color calibration card comprising black, white, three different gray shades, red, green, blue, and yellow has been used for image calibration to improve the comparability of different images. However, the color calibration card was not present in all images. The software that has been used selected the most intensive red value of the image as maximal red value and normalized each other value to said maximal red value. Accordingly, if the card was present in the image, the red color of the card has been selected, if not, the most intense red of the image has been used as maximal red value (e.g. patient's skin, clothing etc). For spectrophotometric measurements, the spectrometer CM-700d (Konica Minolta) was used by applying a measurement diaphragm (Ø 8 mm (MAV)), with activated auto-calibration. Single spot measurement was carried out in three standardized regions in the medial and lateral area according to the split body design. The thereby gained data set comprised 2862 single point measurements. Each measurement comprises the complete L*a*b* color space, as approved by the French Commission Internationale de l'Éclairage (CIE). For objective analysis of efficacy we separated the parameters L*, a* and b* for each individual patient (01-20) and mean values were calculated for each fractions (01-28) and measurement regions (plazebo/verum).

Formulation and Composition

APN201 is produced and filled according to cGMP. The drug substance (rhSOD) is encapsulated in a proprietary liposomal formulation and mixed in a hydrophilic gel (1.6 mg rhSOD per mL) which consists of 1% Carbopol 981NF matrix (pH 7.4). Na-Methyl-Parabene is added as preservative in line with the use of multi dose containers. The placebo consists of the same concentration of the gel-forming matrix (Carbopol 981NF) like APN201 but contains empty liposomes.

Biostatistics and Results

Figure 3:
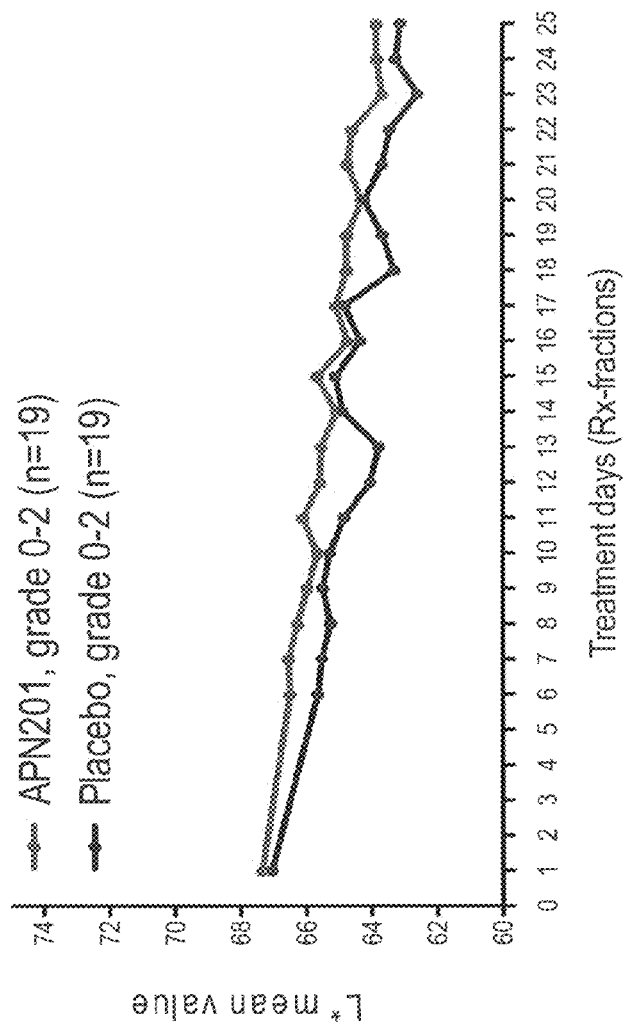
FIG. 3: L*a*b* parameters and their change over treatment time.
Figure 3:
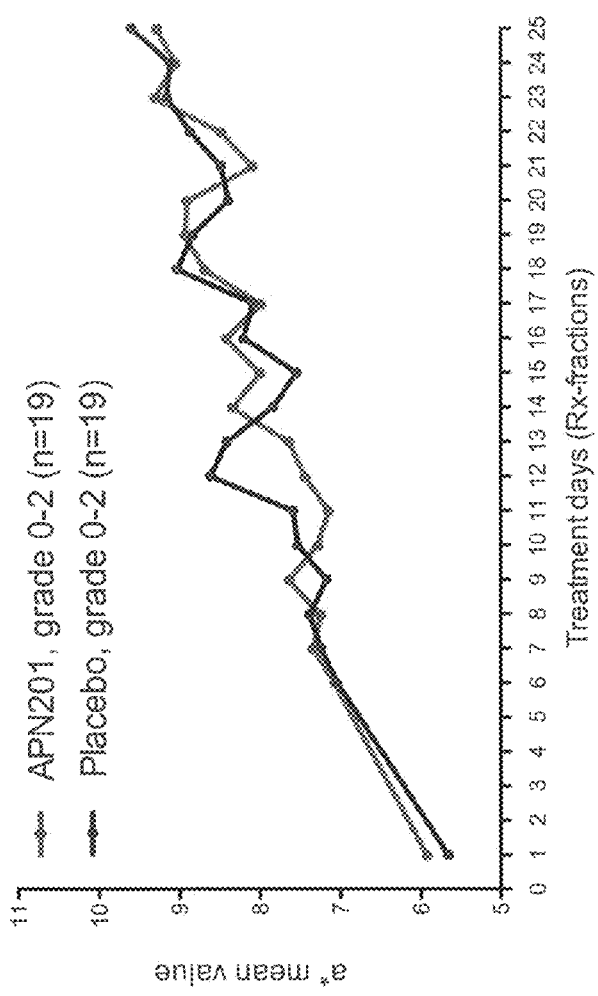
Figure 3:
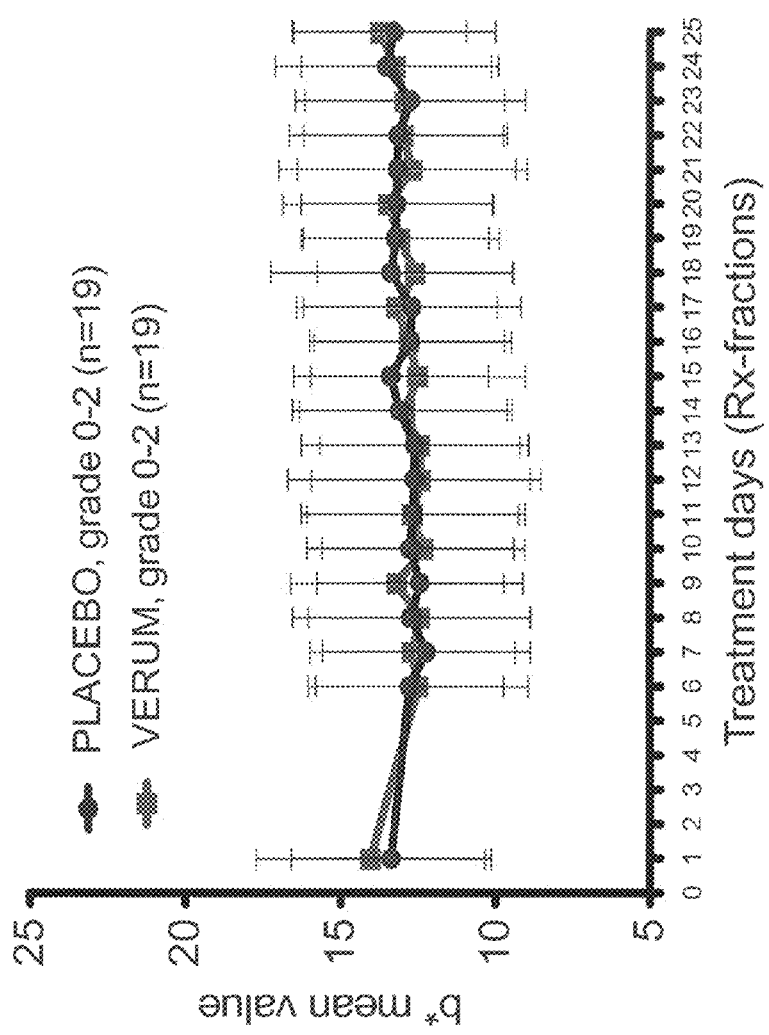
Figure 4:
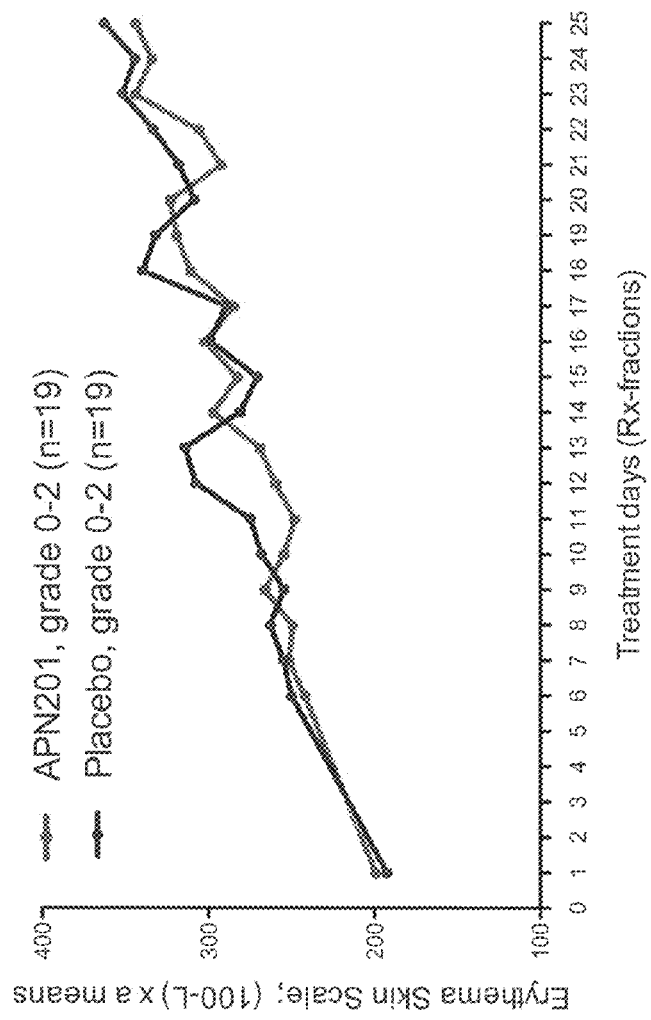
FIG. 4: Erythema values over treatment time (A) and correlation to the subjectively assessed radiodermatitis grade (B).
Figure 4:
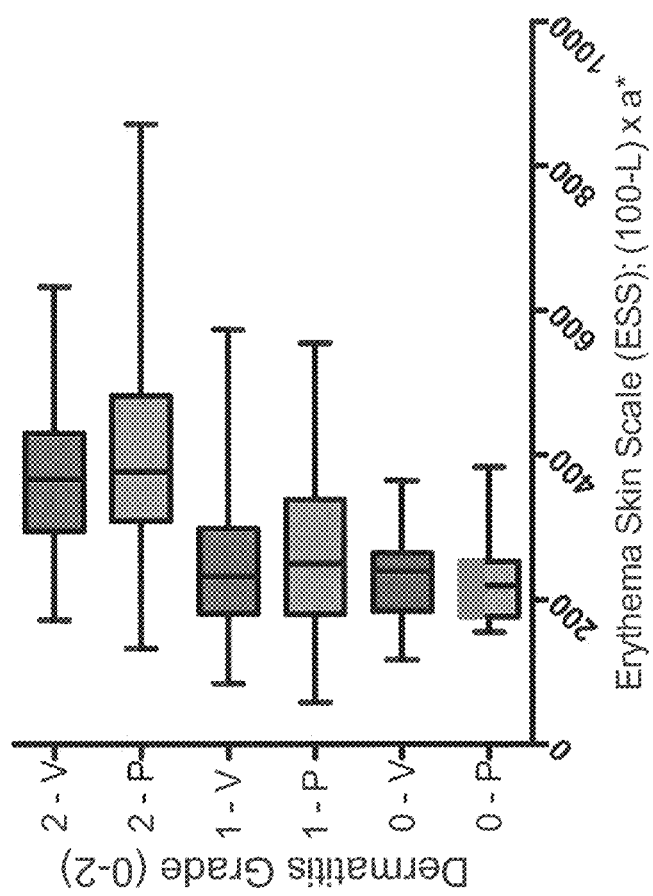
Figure 5:
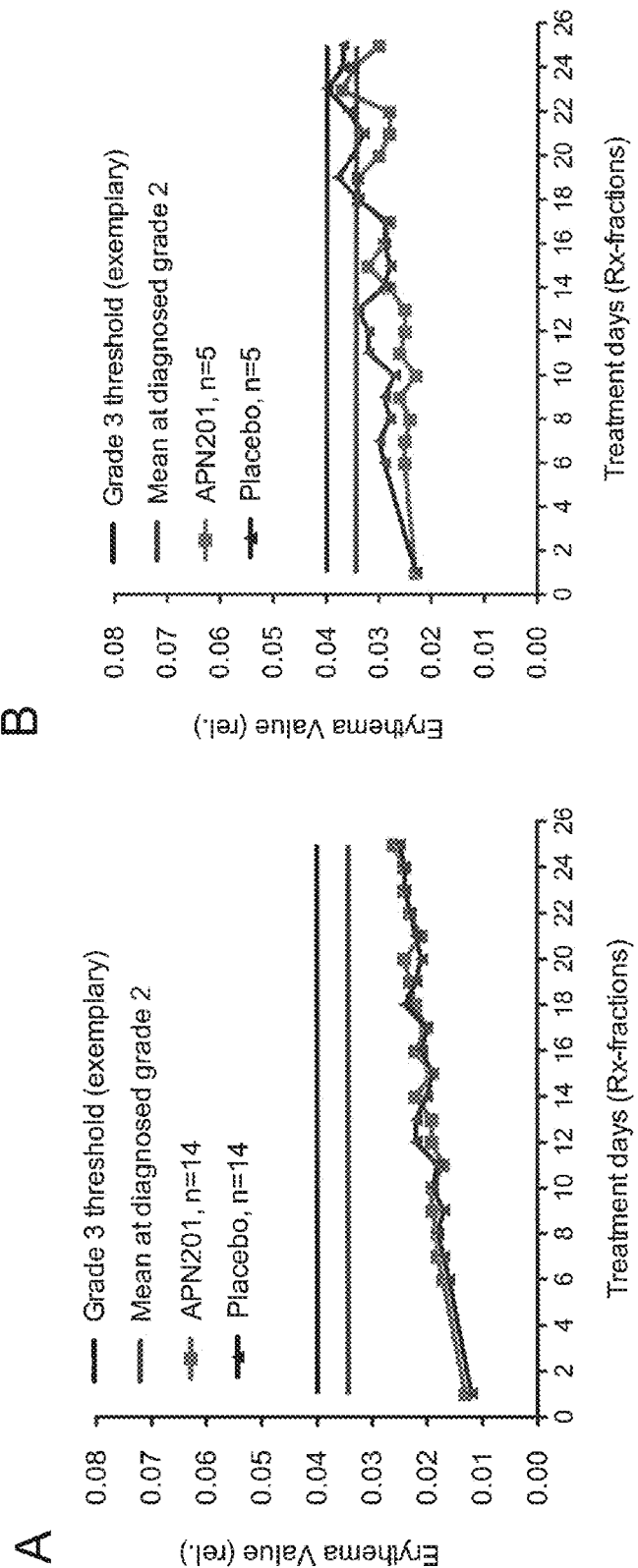
FIG. 5: Erythema values over treatment time, separated for the patient population of a grade 2 (A) and grade 0-1 (B)

For all variables assessed, conducted statistical tests are descriptive. Presented data were summarized with respect to demographic and baseline characteristics, safety- and efficacy observations/measurements. Single spot spectrophotometry delivered consecutive L*a*b* values for each patient (n=19) according to fractions (01-25). The parameters L*, a* and b* were analyzed separately and compared between Placebo and Verum treated skin areas (FIG. 3). Whereas the means for L* and a* correlated well with the subjective assessment of radiodermatitis over study time, no correlation was found with respect to the b* value (FIG. 3). We combined L* and a* by algorithm (100−L*)×a* which gains a novel objective parameter, the "Erythema Value" (EV) (FIG. 4). Final analysis of the time until grade ≥2 development in APN201/Placebo treated skin areas delivered first signs for APN201 efficacy (FIG. 5).

Results 20 patients were enrolled and randomly assigned to receive APN201 and placebo in the course of fractionated radiotherapy. 50.0-50.4 Gy in 25-28 fractions (5×1.8-2 Gy/week).

All patients were Caucasian female with a median age of 58 years (range, 40-72). In 10 patients the carcinoma was located in the right breast, in 10 patients in the left. The most common skin type according to the Fitzpatrick scale was skin type 3 in 65%, followed by skin type 2 in 20% of the population. One patient had diabetes mellitus type 2 and another had a contact dermatitis to band-aids. One patient discontinued treatment because of her request, thus the intention to treat (ITT) population included 19 patients.

All efficacy variables were evaluated on the ITT data set. This data set included all patients who had received at least one application of the study medication and provided efficacy data. Only one patient was excluded for efficacy analysis due to a in compliance after visit for fraction 5. Thus the ITT population included 19 patients.

Initial spectrophotometric analysis of the ITT (n=19) delivered comparable mean values for both split body areas with respect to the investigated parameters, L*, a*, and b*. We observed a trend for a decreasing mean L* and increasing mean a* value over treatment time, unveiling a negative correlation between both objective parameters. This means, the higher the a* value, the more intense is the skin reddening and the lower the L* value the more darker becomes the skin upon irradiation treatment. Both factors correlate with the subjectively assessment of the CTC classification of dermatitis grading 0-2. In contrast, for the b* value, neither a significant change over time, nor a correlation with observed skin reactions could be identified (FIG. 3).

Based on this result we decided to combine the relevant parameters L* and a* by developing the algorithm (100−L*)×a* which resulted in an even more distinct match. The corresponding Box-Blot analysis of this novel parameter in correlation with the clinically assessed grade of radiation dermatitis (grade 0-2) shows a significant increase of the erythema value (EV) mean with higher grading. For the ITT population a EV mean of 435.9 was calculated at the time point of initial diagnose of grade 2 dermatitis which could not be reached until the end of therapy for investigations on the whole population due to the low incident rate of observed grade 2 (5 of 19 patients; 26.3%). No difference in the trend between placebo and verum treated areas could be observed over treatment time in this context. Thus, our applied method provides a novel objective parameter, the erythema value, which allows the objective assessment of erythema and hence connected skin toxicities (FIG. 4).

Furthermore, analysis of the time until grade ≥2 development in APN201/placebo treated skin areas delivered first signs for APN201 efficacy. The mean time (number of irradiation fractions) to grade 2 irritation was 20.5 fractions (range 18-24) with placebo and 23.0 fractions (range, 22-24) with APN201.

Surprisingly the stratification between grade 0-1 and grade 2 patients unveiled a clear difference in the mean EV and observed curve trends between these subgroups (FIG. 5). A nearly 2 fold higher start value in the EV could be observed for patients who developed grade 2 (EV 290) when compared to those with developed grade 0-1 (EV 150). In FIG. 5, the erythema values have been normalized to the theoretical maximal possible value. Said maximal value has been determined based on the assumption that in this example, the maximal L*value is 100, and the maximal a*value is 127, thus, the product of both is set to be the theoretical maximal possible value. All erythema values measured are normalized to said value.

The threshold erythema value for the grade 3 erythema is one exemplary value which has been determined subjectively of another patient not included into the study. The value has been measured at the day the patient was first diagnosed with the grade 3 subjectively by a physician, which was at the day of fraction 26. The patient had the same disease and treatment as the study patients.

In our study no correlation between the radiation field size ($cm^2$), or the Fitzpatrick-Scale (1-2 vs. 3-4) and the CTC grade 2 was observed. The EV value at baseline revealed to be the only statistical significant parameter (p=0.015) being associated to the development of CTC grade 2. Furthermore, a direct correlation of the EV value prior to the irradiation and the estimated risk (≥75% at EV≥300) for CTC grade 2 development could be observed.

Discussion

Based on our observations we suppose the introduction of the novel Erythema Value (EV) parameter which prospectively allows to identify patients with a higher risk for the development of radiation induced skin toxicity of CTC grade ≥2. Measuring the patient's individual EV at the start of irradiation might be of high clinical relevance in order to consider a potential prophylactic treatment with an antioxidant, such as the topical application of APN201 carried out in our study. Secondly the EV should be considered as prospective screening parameter to impede dilution of study data by patients at a lower risk of developing radiodermatitis.

Example 2: Overlapping Color Gradients From Black to White and Red

To prove the applicability of our proposed erythema value for remote analysis of obtained images of a subject we generated a redness gradient starting from the darkest red color to the brightest red color by in silico method using a color depth of 8 bit per color channel (R/G/B). This was achieved by increasing the value of the primary R in the RGB color space from 0 to 255 (8 bit) and then kept constant. On the increasing side of R, the primaries G and B both have always the value 0, on the constant side of R, G and B both have increasing values starting from 0 to 255 by step-size 1, see FIG. 6B. The resulting values were converted into the L*a*b* color space and displayed in FIG. 6A. The fourth series in FIG. 6 shows the corresponding erythema values calculated by the formula ((255−L*)×a*), divided by 255 to get comparable values in the range from 0 to 255. FIG. 7 shows the above described redness gradient including all values of the RGB and L*a*b* color space.

Figure 8B:
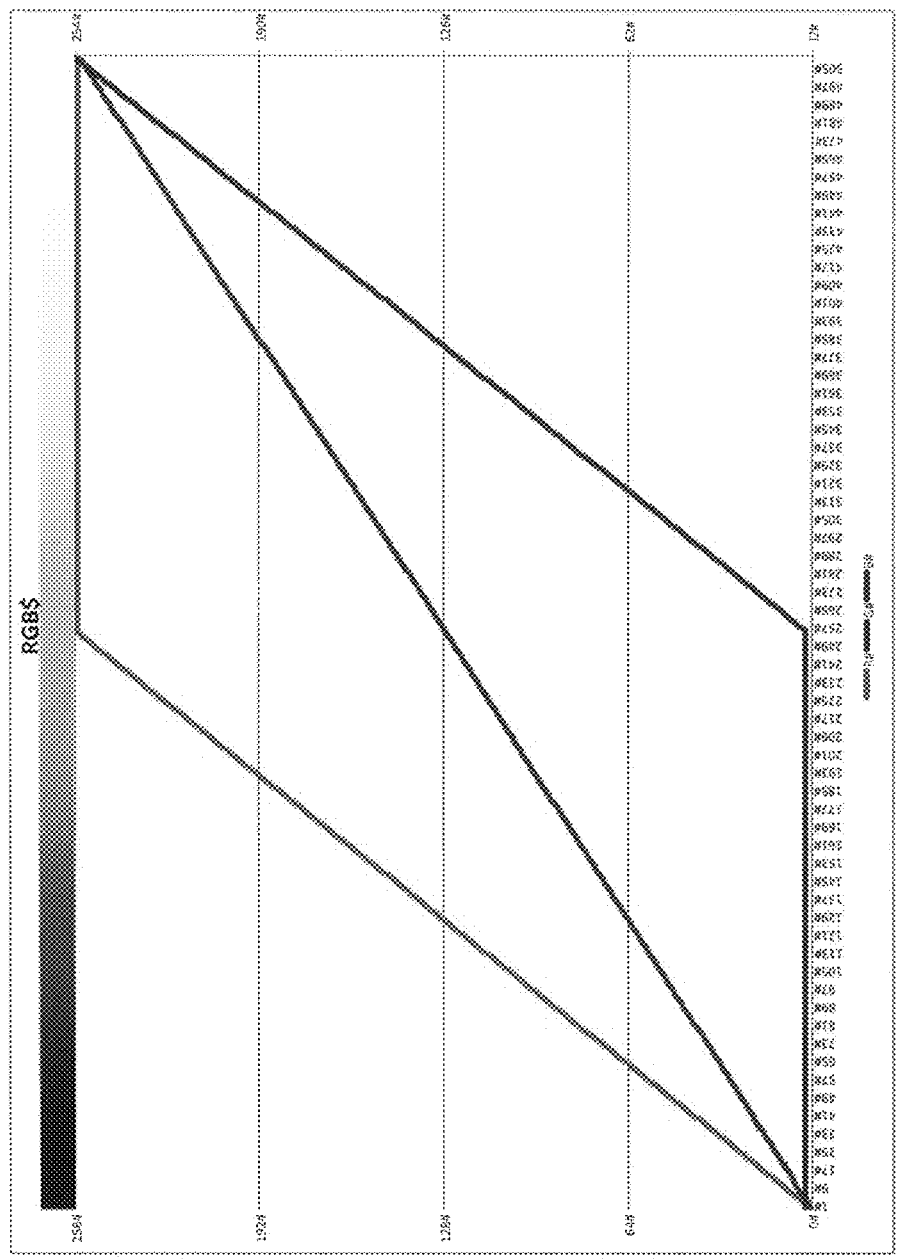

Furthermore a methodical equivalently derived technique was used to test the applicability of our invention for assessing a yellowness value of a skin or mucosa or conjunctive area of a subject, e.g. for objective and time resolved assessment of icterus disease. We generated a yellowness gradient starting from dark yellow (reflecting the color of the yellowish bilirubin pigment observed in a severe grade of icterus) to the brightest yellow color by in silico method using a color depth of 8 bit per color channel (R/G/B). This was achieved by increasing the value of the primary R in the RGB color space from 0 to 255 (8 bit) and then kept constant. On the increasing side of R, the primary B has always the value 0. On the constant side of R, B has increasing values starting from 0 to 255 by step-size 1. The primary G increases uniformly from 0-255 starting from 0 at the increasing side of R; see FIG. 8B. The resulting values were converted into the L*a*b* color space and displayed in FIG. 8A. The fourth series in FIG. 8 shows the corresponding erythema values calculated by the formula ((255−L*)×b*), divided by 255 to get comparable values in the range from 0 to 255. FIG. 9 shows the above described yellowness value gradient including all values of the RGB and L*a*b* color space.

Discussion

In accordance with the visual perception of skin reddening by the human eye our method delivers a broad nearly linear range of the calculated erythema value, proving the technical feasibility of our developed method. Consequently the corresponding methodical steps comprising of obtaining the L* value and the a* value of a measurement according to the L*a*b* color space, and calculating the skin redness value according to the formula $(L^*_{max}-L^*) \times a^*$ were technically converted by generation of a software tool integrating in a cloud based erythema assessment and documentation platform. The software tool is further capable to link to any mobile software application for measuring the light reflectance of a skin or mucosal or conjunctive area of the subject.

Furthermore as a result a therefrom derived computational method was claimed for obtaining the L* and the b* value and calculating the yellowness value of a subject according to the formula $(L^*_{max}-L^*) \times a^*$ which may allow to further extend the invention for any other observed color value of a subject, e.g yellowish pigmentation in case of icterus or bluish pigmentation in case of cyanosis or hematoma of a skin or mucosa or conjunctive area of a subject.

Example 3

Using a Software App Integrating the Invented Methods to Analyse Erythema Values of Naevus Lenticularis Areas in a Phase I Trial (A) and Time Dependent Changes of Analyzed Erythema Values (B)

To test the capabilities of our software app which integrates the provided methods of our invention, we obtained images of skin areas of 14 different subjects (m/f) which were generated by earlier described standardized imaging procedures accompanying to a clinical phase I trial. The trial aimed on to objectively assess the efficacy of a pharmaceutical substance for its assumed capability to attenuate the intensity of Lentigo solaris due to bleaching of Naevus lenticularis areas. Therefore a set of 20 single neavi were assessed in 12 individual subjects over a total treatment period of 4 week. Erythema analysis started from taken images at the before the onset of topical skin treatment (visit 1) and were finished on the last day (visit 4) 4 week post start of topical treatment. The used software app comprises several tools allowing standardized image generation and automated assignment of generated imaging data to a subject by recognizing a specific QR code which may be assigned to a subject or to a analyzed area (Naevus) of a subject. By using our app on a software platform of a mobile device (iPhone) gained images were encrypted and uploaded into a cloud based online platform. Said software app can directly link to the web based (cloud based) image analysis and monitoring platform further allowing remote erythema assessment and monitoring of a measured area of a subject. The areas of interest (Neavi or reference skin) were marked using a selection tool integrated in our image documentation and assessment platform. Finally single erythema values of different areas of interest were calculated by the invented computational method according to the formula $(L^*_{max}-L^*) \times a^*$ and calculated values were normalized automatically according to the formula $(L^*_{max}-L^*) \times a^* / (a^*_{max} \times L^*_{max})$ gaining relative erythema values. Such relative erythema values may range from 0 for minimum to 1 for maximum.

Discussion

As given by the exemplary result in FIG. 10A the application of our developed method integrated in a mobile software application enables remote and objective assessment of erythema values in normal appearing skin areas (reference) versus skin areas marked by lentigo solaris. In accordance with the subjective visual perception of consulted dermatologic experts to interpret taken images surprisingly our invented method could further confirm that topical pharmaceutical treatment of lentigo solaris neavi did not lead to a decrease in the mean intensity of lentigo solaris in our subjects, such could here be proven by time dependent analysis of the skin reddening (erythema) value; see FIG. 10B.

While the above embodiments and exemplary analysis results have been disclosed as the best mode presently contemplated by the inventor it has to be noticed, that these provided examples and given exemplary analysis results should not be interpreted as limiting, due to the reason that professional skilled people within the field, once provided with the present method, can substantially extend the scope of potential applications as exemplary given in above specific embodiments.

The invention claimed is:

1. A computer-based method for assessing erythema of a subject comprising the steps of
measuring, by a digital camera or a spectrophotometer, a light reflectance of a skin or mucosal or conjunctive area of the subject to obtain a measurement, wherein the measuring is performed after the subject has been treated with at least one of a pharmaceutical preparation, a cosmetic preparation, an allergen, and an irradiation therapy; and
obtaining, by a computer, a L* value and a a* value of said measurement according to the L*a*b* color space;
calculating, by the computer, an erythema value according to the formula $(L^*_{max} - L^*) \times a^*$; and outputting at least one of an image and data representing the erythema value to at least one computer imaging and/or mobile imaging device.

2. The method of claim 1 for use in analyzing the pharmaceutical preparation or the cosmetic preparation or the allergen for an ability of the pharmaceutical preparation or the cosmetic preparation or the allergen to cause an erythema or for use in analyzing the pharmaceutical preparation or the cosmetic preparation for an ability of the pharmaceutical preparation or the cosmetic preparation to ameliorate an erythema.

3. The method of claim 1 further comprising
obtaining, by the computer, the L* value and a b* value of said measurement according to the L*a*b color space; and
calculating, by the computer, a yellowness value according to the formula $(L^*_{max} - L^*) \times b^*$.

4. The method of claim 1, wherein the erythema value is correlated to an intensity of an erythema.

5. The method of claim 1, wherein the light reflectance is measured in a color space other than the L*a*b* color space, and the L* value and the a* value and a b* value according to the L*a*b* color space are obtained by converting the light reflectance values of said measurement into the corresponding values of the L*a*b* color space.

6. The method claim 1, wherein the erythema value is compared to a reference erythema value.

7. The method of claim 1, wherein the measuring step and/or the obtaining step and/or the calculating step or any combinations thereof are performed using a mobile device, wherein the mobile device comprises at least one of the digital camera, the spectrophotometer, and the computer.

8. The method of claim 1 further comprising simultaneously measuring, by the camera or spectrophotometer, a normalization marker containing chromatic code elements for automated marker recognition to obtain a normalization measurement and performing, by the computer, a lightning correction of the measurement based on the normalization measurement.

9. The method of claim 1 further comprising normalizing, by the computer, the erythema value by dividing the erythema value by $(a^*_{max} \times L^*_{max})$.

10. The method of claim 1 further comprising the step of detecting a barcode or a quick response code or a near field tag of the subject to automate an allocation process between the subject and the erythema value of the subject.

11. The method of claim 1, further comprising obtaining the measured light reflectance.

12. The method of claim 3, further comprising normalizing the yellowness value by dividing the yellowness value by (b*max×L*max).

13. A computer-based method for obtaining an erythema value of a subject comprising the steps of
measuring, by a digital camera or a spectrophotometer, a light reflectance of a skin or mucosal or conjunctive area of the subject to obtain a measurement, wherein the subject has a condition selected from the group consisting of an erythema, a skin wound, a mucosal wound, a conjunctive wound, a lentigo solaris, a lentigo simplex, a lentigo maligna, a lentigo aestiva, a hematoma, an icterus and a cyanosis, and wherein the skin or mucosal or conjunctive area is affected by the condition;
obtaining, by a computer, a L* value and a a* value of said measurement according to the L*a*b* color space;
calculating, by the computer, the erythema value according to the formula $(L^*max - L^*) \times a^*$; and outputting at least one of an image and data representing the erythema value to at least one computer imaging and/or mobile imaging device.

14. A computer-based method for assessing a risk of a subject to develop erythema caused by an irradiation therapy or for predicting an intensity of erythema that a subject develops due to an irradiation therapy or for predicting a time until a subject develops erythema caused by an irradiation therapy comprising the steps of
measuring, by a digital camera or a spectrophotometer, a light reflectance of a skin or mucosal or conjunctive area of the subject to obtain a measurement, wherein the subject has a cancer and has been designated to undergo the irradiation therapy, and wherein the skin or mucosal or conjunctive area has been irradiated in the irradiation therapy;
obtaining, by a computer, a L* value and a a* value of said measurement according to the L*a*b* color space;
calculating, by the computer, an erythema value according to the formula $(L^*max - L^*) \times a^*$;

comparing, by the computer, the erythema value to at least one reference erythema value such that the risk of the subject to develop erythema caused by the irradiation therapy is assessed or such that the intensity of erythema that the subject develops due to the irradiation therapy is predicted or such that the time until the subject develops erythema caused by the irradiation therapy is predicted; and
outputting at least one of an image and data representing the erythema value to at least one computer imaging and/or mobile imaging device.

* * * * *